(12) United States Patent  
Palma et al.

(10) Patent No.: US 11,891,652 B2
(45) Date of Patent: Feb. 6, 2024

(54) BIOSENSOR DEVICE AND ASSEMBLY METHODS

(71) Applicant: Queen Mary University of London, London (GB)

(72) Inventors: Matteo Palma, London (GB); Xinzhao Xu, London (GB); Pierrick Clement, London (GB)

(73) Assignee: QUEEN MARY UNIVERSITY OF LONDON, London (GB)

( * ) Notice: Subject to any disclaimer, the term of this patent is extended or adjusted under 35 U.S.C. 154(b) by 647 days.

(21) Appl. No.: 16/766,029

(22) PCT Filed: Nov. 23, 2018

(86) PCT No.: PCT/GB2018/053401
§ 371 (c)(1),
(2) Date: May 21, 2020

(87) PCT Pub. No.: WO2019/102217
PCT Pub. Date: May 31, 2019

(65) Prior Publication Data
US 2021/0071238 A1 Mar. 11, 2021

(30) Foreign Application Priority Data
Nov. 24, 2017 (GB) .................... 1719555

(51) Int. Cl.
C12Q 1/6825 (2018.01)
G01N 33/543 (2006.01)
(Continued)

(52) U.S. Cl.
CPC ............ *C12Q 1/6825* (2013.01); *B82Y 35/00* (2013.01); *B82Y 40/00* (2013.01);
(Continued)

(58) Field of Classification Search
CPC .............. C12Q 1/6825; C12Q 2500/00; C12Q 2560/00; B82Y 35/00; B82Y 40/00;
(Continued)

(56) References Cited

U.S. PATENT DOCUMENTS 7,854,826 B2 12/2010 So et al.
9,267,127 B2 2/2016 Liu et al.
(Continued)

FOREIGN PATENT DOCUMENTS

CN 106586952 4/2017
KR 20040075620 8/2004
(Continued)

OTHER PUBLICATIONS

Martinez et al. ("Label-Free DNA Biosensors Based on Functionalized Carbon Nanotube Field Effect Transistors," Nano Letters, vol. 9, No. 2, pp. 530-536, published Jan. 6, 2009). (Year: 2009).*
(Continued)

*Primary Examiner* — Shafiqul Haq
*Assistant Examiner* — Nam P Nguyen
(74) *Attorney, Agent, or Firm* — Casimir Jones SC; Lisa Mueller

(57) ABSTRACT

The invention relates to a method of assembling a biosensor device comprising two or more biosensor units, wherein each unit comprises one or more biosensors comprising one or more carbon nanotubes (CNTs) coated with nucleic acid and one or more sensor molecules coupled to the nucleic acid, wherein each one of the one or more sensor molecules is capable of binding to a target molecule in a sample. Each biosensor unit is capable of detecting a different target molecule in a sample, and each unit comprises one or more biosensors each capable of detecting the same target mol-
(Continued)

ecule. The invention further relates to biosensor devices and methods for detecting target molecules in a sample using the same.

29 Claims, 47 Drawing Sheets

Specification includes a Sequence Listing.

(51) Int. Cl.
B82Y 35/00 (2011.01)
B82Y 40/00 (2011.01)
(52) U.S. Cl.
CPC ..... *C12Q 2500/00* (2013.01); *C12Q 2560/00* (2013.01); *G01N 2333/005* (2013.01); *G01N 2333/195* (2013.01); *G01N 2333/37* (2013.01); *G01N 2458/00* (2013.01)
(58) Field of Classification Search
CPC ....... G01N 2333/005; G01N 2333/195; G01N 2333/37; G01N 2458/00; G01N 33/743; G01N 2333/5755; G01N 33/5438; H10K 85/225; H10K 85/761
See application file for complete search history.

(56) References Cited

U.S. PATENT DOCUMENTS

| | | |
|---|---|---|
| 2004/0200734 A1 | 10/2004 | Co et al. |
| 2004/0235016 A1 | 11/2004 | Hamers et al. |
| 2006/0040381 A1 | 2/2006 | Zhao et al. |
| 2007/0132043 A1 | 6/2007 | Bradley et al. |
| 2008/0094078 A1 | 4/2008 | So et al. |
| 2011/0065588 A1 | 3/2011 | Su et al. |
| 2014/0162893 A1* | 6/2014 | Cash ................ G01N 33/5438 506/16 |
| 2016/0244747 A1 | 8/2016 | Liu et al. |

FOREIGN PATENT DOCUMENTS

| | | |
|---|---|---|
| KR | 20170041375 | 4/2017 |
| WO | WO 2007/102629 | 9/2007 |
| WO | WO 2011/056936 | 5/2011 |
| WO | WO 2012/131403 A1 | 10/2012 |

OTHER PUBLICATIONS

Wang et al. "Preparation of chain-end clickable recombinant protein and its bio-orthogonal modification," Bioorganic Chemistry, vol. 65, pp. 159-166, published Mar. 2, 2016 (Year: 2016).*
Andrews et al., "Cells, biomarkers, and post-traumatic stress disorder: evidence for peripheral involvement in a central disease." J Neurochem. Jan. 2012; 120(1):26-36.
Ao et al., "Differentiating Left- and Right-Handed Carbon Nanotubes by DNA." J Am Chem Soc. Dec. 28, 2016;138(51):16677-16685.
Ao et al., "DNA-controlled partition of carbon nanotubes in polymer aqueous two-phase systems." J Am Chem Soc. Jul. 23, 2014;136(29):10383-92.
Body Fluid, Wikipedia, [retrieved on Oct. 6, 2020] Retrieved from the Internet <URL: https://en.wikipedia.org/wiki/Body_fluid>.
Choi et al., "Dissecting single-molecule signal transduction in carbon nanotube circuits with protein engineering." Nano Lett. Feb. 13, 2013;13(2):625-31.
Choi et al., "Single-molecule lysozyme dynamics monitored by an electronic circuit." Science. Jan. 20, 2012;335(6066):319-24.
Custom DNA oligos, [online] Integrated DNA Technologies, [retrieved on Oct. 6, 2020] Retrieved form the Internet: <URL: https://www.idtdna.com/pages/products/dna-rna/custom-dna-oligos>.
Gatti et al., "Cortisol assays and diagnostic laboratory procedures in human biological fluids." Clin Biochem. Aug. 2009;42(12):1205-17.
Guo, "Single-molecule electrical biosensors based on single-walled carbon nanotubes." Adv Mater. Jul. 5, 2013;25(25):3397-408.
Hamaguchi et al., "Aptamer beacons for the direct detection of proteins." Anal Biochem. Jul. 15, 2001;294(2):126-31.
Innocentive Challenges, [online] [Retrieved Oct. 6, 2020] Retrieved from the Internet: <URL: https://www.innocentive.com/ar/challenge/9933932>.
Kojima et al., "Protein Sensor Using Carbon Nanotube Field Effect Transistor." Jap. J. App. Physics. 2005, 44(4):1596-1598.
Landry et al., "Single-molecule detection of protein efflux from microorganisms using fluorescent single-walled carbon nanotube sensor arrays." Nat Nanotechnol. May 2017;12(4):368-377.
Lapchack et al., "Dehydroepiandrosterone sulfate is neuroprotective in a reversible spinal cord ischemia model: possible involvement of GABA(A) receptors." Stroke. Aug. 2000; 31(8):1953-6.
Li et al., "Selective deposition and alignment of single-walled carbon nanotubes assisted by dielectrophoresis: from thin films to individual nanotubes." *Nanoscale Res Lett.* Apr. 17, 2010;5(6):1072-8.
Liu et al., "Single-molecule detection of proteins using aptamer-functionalized molecular electronic devices." Angew Chem Int Ed Engl. Mar. 7, 2011;50(11):2496-502.
Martin et al., "Tunable stringency aptamer selection and gold nanoparticle assay for detection of cortisol." Anal Bioanal Chem. Jul. 2014; 406(19):4637-47.
Mendonsa et al., "In vitro selection of aptamers with affinity for neuropeptide Y using capillary electrophoresis." J Am Chem Soc. Jul. 6, 2005;127(26):9382-3.
Ordinario et al., "Sequence specific detection of restriction enzymes at DNA-modified carbon nanotube field effect transistors." Anal Chem. Sep. 2, 2014; 86(17):8628-33.
Palma et al., "Controlled formation of carbon nanotube junctions via linker-induced assembly in aqueous solution." J Am Chem Soc. Jun. 12, 2013;135(23):8440-3.
Pan et al., "A new approach to functionalize multi-walled carbon nanotubes by the use of functional polymers." Polymer 2006, 47:4300-4309.
Park et al., "Effects of Sidewall Functionalization on Conducting Properties of Single Wall Carbon Nantubes." Nano Lett. 2006, 6(5): 916-919.
Pugliese et al., "Processive Incorporation of Deoxynucleoside Triphosphate Analogs by Single-Molecule DNA Polymerase I (Klenow Fragment) Nanocircuits." J Am Chem Soc. Aug. 5, 2015; 137(30):9587-94.
SapientSensors Products, [online] [Retrieved Oct. 6, 2020] Retrieved from the Internet: <URL: http://www.sapientsensors.com/products/>.
Schnorr et al.," Wiring-up catalytically active metals in solution with sulfonated carbon Nanotubes." J. Mater. Chem. 2011, 21:4768-4770.
Silvy et al., "CoMoCAT® Single-wall Carbon Nanotubes." SouthWest Nano Technologies, [retrieved on Oct. 6, 2020] Retrieved from the Internet <URL: http://www.sigmaaldrich.com/technical-documents/articles/materials-science/nanomaterials/comocat-carbon-nanotubes.html>.
Sims et al., "Electronic Measurements of Single-Molecule Catalysis by CAMPDependent Protein Kinase A." J. Am. Chem. Soc. 2013, 135:7861-7868.
So et al., "Single-Walled Carbon Nanotube Biosensors Using Aptamers as Molecular Recognition Elements." J. Am. Chem. Soc. 2005, 127:11906-11907.
Sorgenfrei et al., "Label-free single-molecule detection of DNA-hybridization kinetics with a carbon nanotube field-effect transistor." Nature Nanotechnology 2011, 6:126-132.
Vijayaraghavan, "Bottom-up assembly of nano-carbon devices by dielectrophoresis." Phys. Status Solidi B 2013, 250:2505-2517.
Weizmann et al., "DNA-CNT Nanowire Networks for DNA Detection." J Am Chem Soc. Mar. 16, 2011; 133(10): 3238-3241.
Xu et al., "Reconfigurable Carbon Nanotube Multiplexed Sensing Device." Nano Letters 2018 18(7): 4130-4135.

(56) References Cited

OTHER PUBLICATIONS

Yang et al., "Optimizing Cross-reactivity with Evolutionary Search for Sensors." J. Am. Chem. Soc. 2012, 134:1642-1647.
Zhang et al., "Readily Reusable Electrochemical DNA Hybridization Biosensor Based on the Interaction of DNA with Single-Walled Carbon Nanotubes." Anal. Chem. 2009, 81:6006-6012.
Zheng et al., "DNA-assisted dispersion and separation of carbon nanotubes." Nat. Mater. 2003, 2: 338-342.
Zhu et al., "Solution-Processable Carbon Nanoelectrodes for Single-Molecule Investigations." J. Am. Chem. Soc. 2016, 138: 2905-2908.

* cited by examiner

Only cortisol

SEQUENCE LISTING

<160> NUMBER OF SEQ ID NOS: 8

<210> SEQ ID NO 1
<211> LENGTH: 79
<212> TYPE: DNA
<213> ORGANISM: Artificial Sequence
<220> FEATURE:
<223> OTHER INFORMATION: Sequence for Neuropeptide Y detection

<400> SEQUENCE: 1
agcagcacag aggtcagatg caaaccacag cctgagtggt tagcgtatgt catttacgga    60
cctatgcgtg ctaccgtga                                                 79

<210> SEQ ID NO 2
<211> LENGTH: 95
<212> TYPE: DNA
<213> ORGANISM: Artificial Sequence
<220> FEATURE:
<223> OTHER INFORMATION: Sequence for cortisol detection

<400> SEQUENCE: 2
gttgttgttg ggaatggatc cacatccatg gatgggcaat gcggggtgga gaatggttgc    60
cgcacttcgg cttcactgca gacttgacga agctt                               95

<210> SEQ ID NO 3
<211> LENGTH: 44
<212> TYPE: DNA
<213> ORGANISM: Artificial Sequence
<220> FEATURE:
<223> OTHER INFORMATION: Sequence for DHEAS detection

<400> SEQUENCE: 3
ctgctctcgg gacgtggatt ttccgcatac gaagttgtcc cgag                     44

<210> SEQ ID NO 4
<211> LENGTH: 85
<212> TYPE: DNA
<213> ORGANISM: Artificial Sequence
<220> FEATURE:
<223> OTHER INFORMATION: Cortisol aptamer
<220> FEATURE:
<221> NAME/KEY: misc_feature
<222> LOCATION: (1)..(1)
<223> OTHER INFORMATION: may be conjugated to azide

<400> SEQUENCE: 4
ggaatggatc cacatccatg gatgggcaat gcggggtgga gaatggttgc cgcacttcgg    60
cttcactgca gacttgacga agctt                                          85

<210> SEQ ID NO 5
<211> LENGTH: 80
<212> TYPE: DNA
<213> ORGANISM: Artificial Sequence
<220> FEATURE:
<223> OTHER INFORMATION: Neuropeptide Y aptamer
<220> FEATURE:
<221> NAME/KEY: misc_feature
<222> LOCATION: (1)..(1)
<223> OTHER INFORMATION: may be conjugated to azide

<400> SEQUENCE: 5
agcagcacag aggtcagatg caaaccacag cctgagtggt tagcgtatgt catttacgga    60
cctatgcgtg ctaccgtgaa                                                80

```
<210> SEQ ID NO 6
<211> LENGTH: 44
<212> TYPE: DNA
<213> ORGANISM: Artificial Sequence
<220> FEATURE:
<223> OTHER INFORMATION: DHEAS aptamer
<220> FEATURE:
<221> NAME/KEY: misc_feature
<222> LOCATION: (1)..(1)
<223> OTHER INFORMATION: may be conjugated to azide

<400> SEQUENCE: 6
ctgctctcgg gacgtggatt ttccgcatac gaagttgtcc cgag          44

<210> SEQ ID NO 7
<211> LENGTH: 85
<212> TYPE: DNA
<213> ORGANISM: Artificial Sequence
<220> FEATURE:
<223> OTHER INFORMATION: Sequence of the DNA complementary to cortisol
      aptamer

<400> SEQUENCE: 7
aagcttcgtc aagtctgcag tgaagccgaa gtgcggcaac cattctccac cccgcattgc      60
ccatccatgg atgtggatcc attcc                                            85

<210> SEQ ID NO 8
<211> LENGTH: 85
<212> TYPE: DNA
<213> ORGANISM: Artificial Sequence
<220> FEATURE:
<223> OTHER INFORMATION: Sequence of the non-complementary DNA used in
      non-complementary control experiment (Figure 19) and in Example 15

<400> SEQUENCE: 8
gattcagcaa ttaagctcta agcgatccgc aacactgacc tcttatcaaa aggagcaatt      60
aaaggtactc tctaatcctg acggg                                            85
```

BIOSENSOR DEVICE AND ASSEMBLY METHODS

CROSS-REFERENCE TO RELATED APPLICATIONS

This application is a national phase application under 35 U.S.C. § 371 of PCT International Application No. PCT/GB2018/053401, filed Nov. 23, 2018, which claims the benefit of Great Britain Application No. 1719555.3, filed Nov. 24, 2017, each of which are herein incorporated by reference.

FIELD OF THE INVENTION

The invention relates to a method of assembling a biosensor device comprising two or more biosensor units, wherein each unit comprises one or more biosensors comprising one or more carbon nanotubes. Each biosensor unit is capable of detecting a different target molecule in a sample, and each unit comprises one or more biosensors each capable of detecting the same target molecule. The invention further relates to biosensor devices and methods for detecting target molecules in a sample using the same.

BACKGROUND OF THE INVENTION

There is an ongoing emphasis on the importance of developing medical technologies to meet the increasing demands of a growing ageing population having an extended lifespan. As such, there is an increasing necessity for the early diagnosis of cancers and other diseases and disorders. Alongside this, there is an increasing need for the monitoring of disease states. In particular, there is an increasing need for point-of-care and companion medical devices that enable diagnosis and monitoring of diseases and disorders. Such devices should be cost-effective to manufacture and should be capable of being used easily and rapidly.

In addition, there is a need for devices which are capable of diagnosing and monitoring multiple conditions simultaneously, for example from blood, serum, plasma, saliva, urine, mucous, vomit, faeces, or sweat samples obtained from an individual. Such devices could detect and identify the presence of components derived from biological samples, such as proteins, amino acids, organic/inorganic compounds for the diagnosis and monitoring of diseases and disorders.

During the last decade, technologies involving carbon nanotubes, and in particular single walled carbon nanotubes (SWCNTs), have undergone a rapid expansion. SWCNTs have been applied for use in biological sensing devices. However, despite the substantial progress in SWCNT-based electronics from both fundamental and technological standpoints, considerable challenges remain. Principal among these are the time and cost involved in the growing of the SWCNTs, e.g. via chemical vapour deposition, and the need for a facile and scalable technology for the establishment of bio-electrical detection capability of individual SWCNTs.

Target biomolecules in close proximity to SWCNTs causes alternation of electronic properties via various mechanisms which makes SWCNTs particularly useful in electrical-based detection methods (e.g. Weizmann et al. *J. Am. Chem Soc.* 2011, 133, 3238; Sims et al. *J. Am. Chem. Soc.* 2013, 135, 7861-7868). Additionally, the use of SWCNTs ensures appropriate size compatibility with biological analytes (Guo et al. *Adv. Mater.* 2013, 25, 3397-408.; Schnorr et al. *J. Mater. Chem.* 2010, 21, 4768.). Further to this, use of nucleic acid aptamers as sensor molecules on SWCNT electrical platforms is advantageous due to (i) aptamers' high affinity and specificity (comparable with those of antibodies); (ii) little or nobatch-to-batch variation in their production (unlike antibodies); and (iii) the easiness in their design and engineering (e.g. Hamaguchi et al. *M. Anal. Biochem.* 2001, 294, 126-131. Nevertheless, the fabrication of these sensing platforms is still costly and time-consuming, typically involving numerous fabrication steps, from chemical vapor deposition of the CNTs, to lithographic patterning. Moreover, and most importantly, the SWCNT-aptamer biosensing devices so far presented do not allow for multisensing capability nor low-cost processability (ideally from solution).

Solution-based assembly methods would represent a powerful approach to the manufacturing of SWCNT-based biosensors by providing simplified and easier procedures which could be implemented quicker and cheaper compared to current methods. Additionally, this would allow more versatile sensors to be produced which could detect multiple analytes simultaneously. Solution-based methods also enabled devices to be reconfigured and reused via cleaning procedures. However, such solution based methods have thus far not been described. Thus whilst advances in micro/nanofabrication technologies and the discovery and development of abundant nanoscale materials such as SWCNTs have opened up new possibilities for developing novel bioelectronic sensors which hold great potential, current strategies for the fabrication of biosensing devices do not allow for combined ultrahigh sensitivity, low-cost processability, and simultaneous detection of multiple biotargets.

SUMMARY OF THE INVENTION

The inventors have presented a strategy for the facile fabrication of reconfigurable and solution processable nanoscale multiplexed biosensors, based on SWCNTs. DNA-wrapped (hence water-soluble) SWCNT (Zheng et al. *Nat. Mater.* 2003, 2, 338-342) functionalized with specific nucleotide sequences are employed as selective recognition elements. Distinct SWCNT-aptamer hybrids are immobilized on the same chip from solution onto prepatterned electrodes via dielectrophoresis (DEP). This enables fabrication of a multisensing platform for the simultaneous electrical detection of different biomarkers.

As a proof-of-concept, the inventors have used the devices disclosed herein for both the selective detection of ss-DNA (i.e., hybridization events) and multiplexed sensing of cortisol, (Gatti et al. *Clin. Biochem.* 2009, 42, 1205-1217; Martin et al. *N. Anal. Bioanal. Chem.* 2014, 406, 4637-464), neuropeptide Y (NPY) (Andrews et al. *J. Neurochem.* 2012, 120, 26-36.; Mendonsa et al. *J. Am. Chem. Soc.* 2005, 127, 9382-9383), and dehydroepiandrosterone-sulfate (DHEAS) (Lapchak et al. *Stroke,* 2000, 31, 1953-1957.; Yang et al. *J. Am. Chem. Soc.* 2012, 134, 1642-1647). The biomarkers selected play roles in various physiological processes such as energy metabolism, blood pressure regulation, cognitive function, post-traumatic stress disorder, and traumatic brain injury (Gatti et al. *Clin. Biochem.* 2009, 42, 1205-1217; Andrews et al. *J. Neurochem.* 2012, 120, 26-36). The devices disclosed herein can perform real-time detection of these hormones at their physiologically relevant concentrations, from picomolar to micromolar; additionally, the devices disclosed herein are reconfigurable and reusable characteristic via a cleaning procedure.

Accordingly the present invention provides a method of assembling a biosensor device comprising two or more biosensor units, wherein each unit is capable of detecting a different target molecule in a sample, and wherein each unit comprises one or more biosensors each capable of detecting the same target molecule, the method comprising:

(i) performing a first assembly cycle comprising:
   A. providing a population of first carbon nanotubes (CNTs) coated with nucleic acid molecules, wherein nucleic acid molecules are functionalised with functional groups suitable for coupling first sensor molecules to nucleic acid molecules, wherein each first sensor molecule is capable of binding to a first target molecule;
   B. providing a substrate comprising a plurality of electrode pairs;
   C. immobilising one or more coated CNTs between separate electrode pairs, wherein each CNT forms an electrical connection between electrodes of a pair;
   D. coupling one or more first sensor molecules to the nucleic acid of each coated CNT, wherein each first sensor molecule is capable of binding to a first target molecule;
   E. washing the substrate to remove non-immobilised coated CNTs; and
(ii) performing a second assembly cycle comprising repeating steps (A) to (E), wherein in repeat step (A) the population of first CNTs is replaced with a population of second CNTs, and wherein functional groups are suitable for coupling second sensor molecules to nucleic acid molecules; and wherein in repeat step (D) the one or more first sensor molecules are replaced with one or more second sensor molecules, wherein each second sensor molecule is capable of binding to a second target molecule.

The assembly methods of the invention are further defined in more detail herein.

The invention also provides a biosensor device comprising two or more biosensor units, each unit comprising one or more biosensors; wherein each biosensor comprises one or more CNTs coated with nucleic acid and one or more sensor molecules coupled to the nucleic acid, wherein each one of the one or more sensor molecules is capable of binding to a target molecule in a sample, and wherein the one or more CNTs of each biosensor are immobilised between electrodes of an electrode pair on a substrate to form an electrical connection between electrodes; wherein sensor molecules of each biosensor of a unit detect the same target molecule, and wherein each unit detects a different target molecule.

Devices of the invention are further defined in more detail herein.

The invention further provides a method of detecting two, three or more different target molecules in a sample, the method comprising providing a biosensor device of the invention, or providing a biosensor device obtainable by any one of the assembly methods of the invention described herein, contacting the device with a sample, separately measuring an electrical response of biosensor units, and determining the presence, absence or quantity of a target molecule in the sample based on the electrical response measurement.

The detection methods of the invention are further defined in more detail herein.

The invention additionally provides a kit comprising a substrate comprising a plurality of pre-patterned electrode pairs and two or more solutions; wherein the first solution comprises a population of first carbon nanotubes (CNTs) coated with nucleic acid molecules, wherein one or more first sensor molecules have been coupled to the nucleic acid of coated first CNTs, wherein each first sensor molecule is capable of binding to a first target molecule, wherein the second solution comprises a population of second carbon nanotubes (CNTs) coated with nucleic acid molecules, wherein one or more second sensor molecules have been coupled to the nucleic acid of coated second CNTs, wherein each second sensor molecule is capable of binding to a second target molecule.

Kits of the invention are further defined in more detail herein.

Each aspect of the invention as defined above is further particularised in the appended claims.

BRIEF DESCRIPTION OF THE FIGURES

FIG. 2 shows the assembly of a biosensor device comprising three units, each unit comprises one biosensor, each biosensor comprises one CNT functionalised with sensor molecules (e.g. aptamers), each CNT is functionalised with the same species of sensor molecule to detect the same target molecule, and the species of sensor molecules differ as between each biosensor so that the resulting biosensor device is capable of detecting three different sensor molecules, in this case cortisol, neuropeptide Y and dehydroepiandrosterone sulphate (DHEAS).

FIGS. 12 A, B and C show that only the cortisol biosensor unit of the device responds when cortisol only is applied to the biosensor device. FIGS. 12 D, E and F show that only the cortisol and NPY biosensor units of the device respond when cortisol and NPY only are applied to the biosensor device. FIGS. 12 G, H and I show that all three biosensor units respond when cortisol, NPY and DHEAS are simultaneously applied to the biosensor device. FIG. 12 shows that biosensor units can be re-set/reversed to their initial state by removing the target molecule bound to the sensor molecule via the addition of 8M of urea solution. ($V_{sd}$=100 mV): the + sign indicates the addition/presence of the analyte of interest; the "cleaning step" indicates the addition of 8M of urea in order to regenerate the sensor after each detection; "after cleaning" indicates the measurements performed after this step.

DETAILED DESCRIPTION OF THE INVENTION

The present invention provides a method for the fabrication of solution-processable nanoscale biosensors based on semi-conducting individual carbon nanotubes (CNTs) via a bottom-up assembly strategy. DNA-wrapped (hence water-soluble) CNTs are immobilised from solution between two pre-patterned electrodes e.g. via dielectrophoresis (DEP). The assembly between electrodes is induced by an AC voltage bias applied to the electrodes. The CNTs are functionalised with specific biomolecules (e.g. nucleotide sequences or proteins) to be employed as selective recognition elements for target molecules (analytes) of interest. For example, by tethering a specific aptamer on the DNA that is wrapped around the CNTs, it is possible to conserve the electronic properties of the CNTs which can be further utilized to electrically sense target molecules of interest once the CNTs are immobilised in a device configuration.

The invention additionally provides biosensor devices comprising two or more biosensor units, such as biosensor devices as manufactured according to the assembly methods of the invention as described herein.

The invention further provides detection methods using biosensor devices of the invention as described herein.

The invention also provides kits comprising components suitable for manufacturing biosensor devices of the invention, including via the assembly methods of the invention as described herein.

Aspects of the present invention are defined further herein, and are described in more detail as follows.

Device Structure

Biosensor devices of the invention are assembled to comprise two or more biosensor units.

Each unit is capable of detecting a different target molecule in a sample. Target molecules for detection may be selected as desired.

Merely by way of example, a biosensor device of the invention may be assembled to comprise three biosensor units, one unit capable of detecting cortisol, another unit capable of detecting neuropeptide Y (NPY) and a yet further unit capable of detecting dehydroepiandrosterone sulphate (DHEAS).

Each biosensor unit is capable of detecting the same target molecule, and each unit is capable of detecting a different target molecule compared to the other units of the device.

Figure 5:
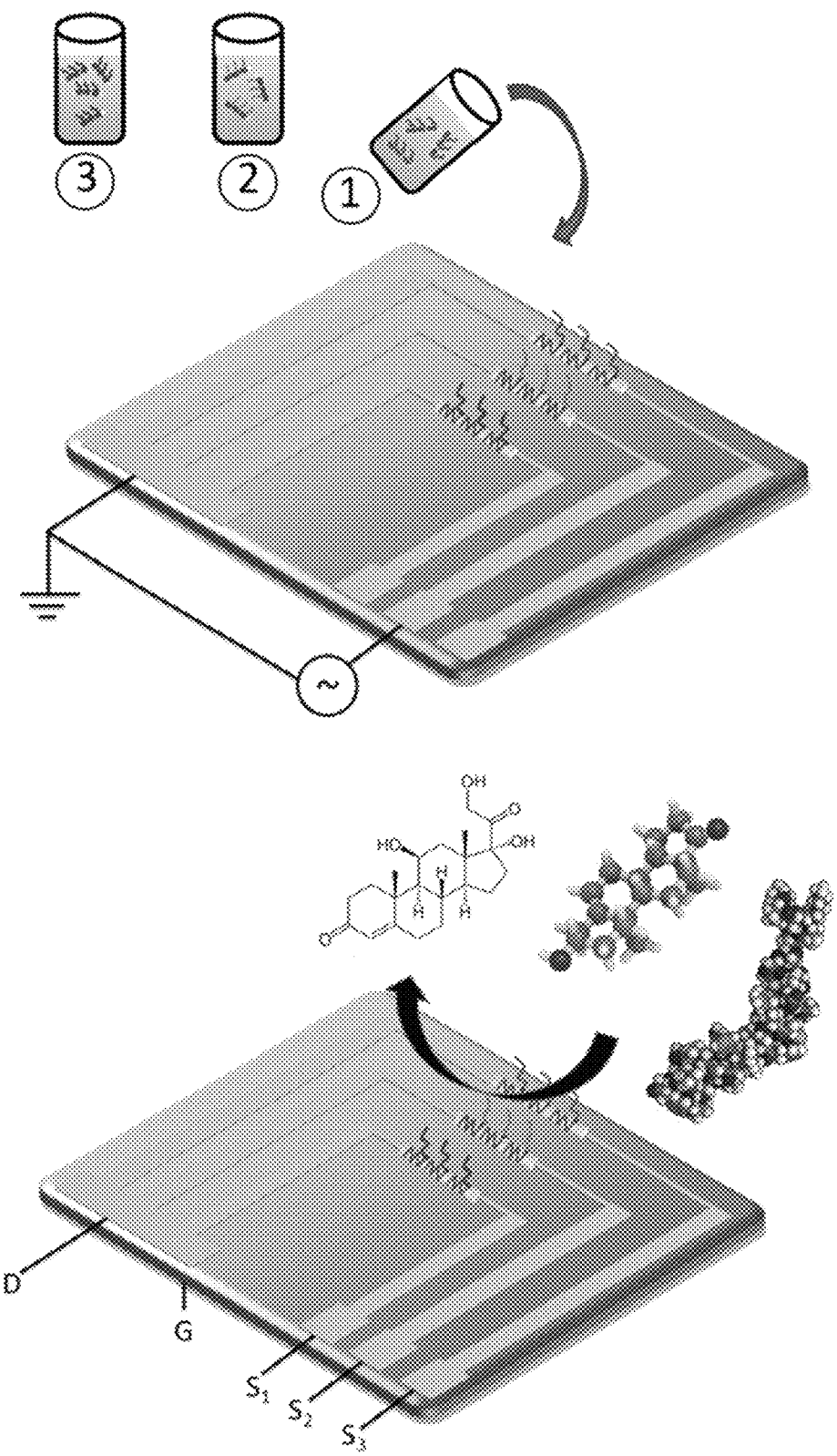
FIG. 5 shows (top) schematic of successive immobilisation via DEP of functionalised SWCNTs, and (bottom) electronic configuration as field effect transistor (FET) showing the source (S), the drain (D) and the gate (G).

Each unit of a device comprises one or more biosensors. Each biosensor comprises at least one CNT, typically more than one CNT, as described in more detail herein, immobilised across electrodes of a pair of electrodes to form an electrical connection between the electrodes of the pair. The CNT(s) of each biosensor may comprise one or more sensor molecules coupled to a CNT as described herein and capable of detecting the same target molecule. Each CNT of a biosensor typically comprises multiple sensor molecules coupled to each CNT. Each unit of a device typically comprises multiple biosensors. FIG. 5 shows one example structure of a biosensor device of the invention. In this example the device is shown to comprise three units. Each unit is capable of detecting a different target molecule (lower panel). In this example each unit comprises a single biosensor comprising a single CNT coupled across electrodes of an electrode pair. Typically however, biosensor units of devices of the invention will comprise more than one biosensor. Furthermore, biosensors of each unit will comprise one or more CNT immobilised across electrodes of a pair, typically between 5 and 10 CNTs or more are immobilised across electrodes of a pair, such as 11, 12, 13, 14, 15, 16, 17, 18, 19 or 20 or more CNTs.

Each sensor molecule coupled to a CNT of a biosensor may be the same species of molecule, e.g. aptamers all having the same sequence. Furthermore, and as described further herein, distinct aptamers, distinct proteins, and/or distinct small molecules or any combination thereof, specific for the same target can be used for increased confidence in diagnosis and/or monitoring of a target molecule/analyte. Thus sensor molecules coupled to a CNT of a biosensor may comprise different species of molecules.

Carbon Nanotubes (CNTs)

Biosensor devices of the invention utilise carbon nanotubes (CNTs) for detection purposes.

CNTs possess outstanding properties such as high mechanical strength, flexibility, and high electrical and thermal conductivity. These properties enable nano-scale miniaturisation of high-speed and high-power electrical circuits. CNTs are therefore attractive materials for various applications in many industries such as electronics, bioengineering, environmental energy, materials, pharmaceuticals, and so forth. Recently, much research has been focused on developing new applications in the field of medicine and biotechnology.

CNTs have a cylindrical structure with walls of carbon atoms formed of a single atom thick sheet termed graphene. The carbon atoms are arranged in a hexagonal honeycomb lattice. A CNT can be a single walled CNT (SWCNT) comprising a single seamless graphene cylinder. Alternatively, a CNT can be arranged as a multi-walled CNT (MWCNT). MWCNTs may comprise several separate SWCNTs of decreasing cross-sectional diameter arranged within each other, or alternatively a single sheet of graphene rolled around itself.

The configuration and orientation of the honeycomb structure of SWCNTs can vary. The variation is apparent if a SWCNT is notionally created by rolling a single sheet of graphene into a seamless cylinder. The honeycomb lattice arrangement may be mapped along two vector indices termed n and m. The "rolling" of the graphene sheet relative to these vector indices can dictate the structural arrangement of the repeated hexagonal units within the SWCNT lattice. In this manner, SWCNT lattices may be arranged in a "zig-zag" or "armchair" orientation. Other types of "chiral" arrangements are possible. Important functional properties of SWCNTs can be dictated by the chirality of the honeycomb lattice arrangement. Most significantly, the electrical conductivity of SWCNTs can vary, exhibiting metallic or semiconducting properties depending upon the values of n and m in the lattice.

The present invention provides a solution-phase method for manufacturing different biosensor units within the same biosensor device. Each biosensor unit may comprise one or more biosensors. Each biosensor of a biosensor unit comprises one or more CNTs coupled to one or more sensor molecules. As will be described in more detail herein, biosensors of the invention are formed by immobilising CNTs across junctions separating electrode pairs, preferably using DEP techniques. This is achieved by selectively electrically addressing specific electrode pairs. The method enables pre-determined first CNTs to be selectively immobilised to create a first biosensor unit capable of detecting a first target molecule or analyte. The method then enables pre-determined second CNTs to be selectively immobilised to create a second biosensor unit capable of detecting a second target molecule or analyte. Further biosensor units can be created sequentially in the same way. Because the method allows the sequential immobilisation of pre-determined CNTs, it is possible to pre-select the chirality of the CNT which will be used to create a given biosensor. It is consequently possible to pre-select the electrical conductivity properties of the CNT which will be used to create a given biosensor. The ability to select the electrical conductivity properties of the CNT in combination with the choice of the specific sensor molecule which is coupled to the CNT allows each biosensor unit to be optimised for the detection of the specific target molecule or analyte relevant to that particular biosensor unit. Thus the methods of the invention offer a high degree of flexibility allowing the creation of versatile biosensor devices which not only can detect different analytes simultaneously but can also do so in an optimised manner, providing for increased sensitivity in detection.

Preferred embodiments of the invention involve biosensor devices comprising SWCNTs, preferably having 7,6 chirality.

SWCNTs may be purchased commercially. One example of a commercial product is "CoMoCAT® Single-wall Carbon Nanotubes" available from Sigma Aldrich.

http://www.sigmaaldrich.com/technical-documents/articles/materials-science/nanomaterials/comocat-carbon-nanotubes.html Preferably, the CNTs to be used in a sensor disclosed herein are single-walled with a diameter of about 8 Å. CNTs with a diameter of greater than 1 nm can also be used. This will allow for the presence of more sensor molecules per CNT, and may further increase the sensitivity of the device.

Separation of CNTs by length can be achieved via methods such as size-exclusion chromatography so as to achieve populations of CNTs of substantially uniform length. For the present methods, average lengths of of CNTs may be approximately about 100 nm to about 200 nm, preferably about 150 nm.

Nucleic Acid Coating of CNTs

In the present methods and biosensor devices of the invention, CNTs are coated with nucleic acid. This serves two purposes. Firstly, the nucleic acid allows CNTs to be solubilised. Secondly, the nucleic acid provides functional groups which allow sensor molecules to be coupled to the CNT.

Typically, dry powdered CNTs are first added to a suitable solvent. It is possible to solubilise CNTs by first adding dry powdered CNTs to the solvent and then adding nucleic acid molecules to the solvent.

Preferably, dry powdered CNTs are added to the solvent wherein the solvent already comprises pre-dissolved nucleic acid. Upon addition of dry powdered CNTs to the nucleic acid-containing solution the CNTs become coated with nucleic acid.

The solvent may be any suitable solvent which may facilitate solubilisation of CNTs and nucleic acids. Preferably the solvent is deionised (DI) water. Alternatively, the solvent may be an aqueous-based buffer solution.

CNTs and nucleic acids interact in solution to form a charged hybrid structure. Without wishing to be bound by theory, the following mechanism of action has been proposed for hybrid formation between CNTs and nucleic acids such as DNA. Nucleobases such as guanine, cytosine, adenine, thymine and uracil contain aromatic groups that are believed to π-stack with the side walls of CNTs. Single-walled CNTs confine and orientate DNA molecules by acting as a scaffold resulting in helical wrapping of DNA around the surface of CNTs. The hydrophillic sugar-phosphate backbone is exposed to the solvent and thereby promotes solubilisation of the CNT, resulting in its dispersion and separation.

The nucleic acid may be any nucleic acid suitable for coating CNTs. The nucleic acid may be single stranded or double stranded, preferably single stranded. The nucleic acid is preferably DNA. The nucleic acid molecules may be provided in a length sufficient for coating at least a portion of the CNT. The nucleic acid molecules may be provided in a length sufficient for coating the full length of the CNT, or substantially the full length of the CNT. Preferably, the full length or substantially the full length of the CNT is coated. A single nucleic acid molecule or multiple nucleic acid molecules may coat a portion or the full length of the SWCNT or substantially the full length of the SWCNT.

Examples of a nucleic acid solution which may be used to coat CNTs is an aqueous solution comprising DNA (TCG)$_4$TC in single stranded form and/or an aqueous solution comprising DNA (GTT)$_3$G-NH$_2$ in single stranded form e.g. in 0.1 M NaCl available for purchase as oligonucleotides from standard suppliers, such as Integrated DNA Technologies (e.g. see https://www.idtdna.com/pages/products/dna-rna/custom-dna-oligos). In principle, any suitable CNT-wrapping nucleic acid may be used provided that the nucleic acid may be provided with a functional group suitable for coupling a sensor molecule, or provided that functional groups can be generated upon the nucleic acid.

CNTs may be dissolved into an aqueous nucleic acid solution to a concentration of e.g. 1 mg/mL.

To facilitate solubilisation of CNTs, CNT nucleic acid mixtures may be sonicated. For example, mixtures may be sonicated in an ice-water bath for e.g. 2 hours. After sonication, the mixture may be separated to remove insoluble material. For example, the mixture may be divided into suitably sized aliquots and centrifuged, e.g. for 90 minutes at 17,000 g, to pellet insoluble material and leaving solubilised nucleic acid-CNT solution supernatents.

In typical exemplary methods wherein CNTs are solubilised to a concentration of 1 mg mL$^{-1}$, the final mass concentration following sonication and centrifugation may be approximately 0.5 mg mL$^{-1}$.

In the methods described herein the fabricated biosensor devices comprise two or more biosensor units wherein each unit comprises one or more biosensors. Each biosensor of a biosensor unit comprises one or more CNTs coupled to one or more sensor molecules. CNTs of a biosensor unit may be pre-selected to have a specific chirality, and thus pre-selected to have specific electrical conductivity properties. Thus CNTs of a first biosensor unit may comprise one specific chirality and CNTs of a second biosensor unit may comprise a different chirality and so on. Each biosensor may comprise multiple CNTs immobilised across electrodes of a pair, wherein the CNTs comprise a mixture of different chiralities.

Nucleic acid wrapped CNTs of different chiralities may be prepared separately in different solution batches for later use in assembling biosensor units of the device. Alternatively, CNTs of different chiralities may be added to the same aqueous nucleic acid solution. Following coating with nucleic acid, CNTs of different chiralities in the same aqueous nucleic acid solution may be separated into single chirality species to obtain a solution of CNTs with the same electrical conductivity properties. Separation may be for example achieved via a polymer aqueous two-phase separation method (Ao et al., *J. Am. Chem. Soc.* 2014, 136, 10383-10392; Ao et al. *J. Am. Chem. Soc.* 2016, 138, 16677-16685).

Functionalisation of CNTs

In the present methods and biosensor devices of the invention, nucleic acids preferably harbor a sequence comprising a functional group to be used for the coupling of a sensor molecule, e.g. an aptamer or a protein. Non-covalent binding of nucleic acids such as DNA to CNTs represents a non-destructive way of functionalising CNTs, as opposed to covalent functionalisation achieved via chemical-based methods (see Pan et al. (2006) Polymer 47 4300).

One method of functionalising DNA is to provide the DNA with a free amino group. The free amino group can react, via an amidation reaction, with an N-hydroxysuccinimide (NHS) functionalised bicyclononyne (BCN). An azide terminated sensor molecule such as an aptamer can then be covalently attached, e.g. via a copper-free click chemistry to the BCN-functionalised DNA-wrapped CNTs.

Functionalisation of CNTs and attachment of sensor molecules can be carried out in solution prior to the deposition of the CNTs e.g. via DEP on the pre-patterned electrodes as described below. Alternatively, it is possible to first coat CNTs with nucleic acids, cast the coated CNTs via DEP on the metal electrode pairs, and then perform the functionalisation and attachment reactions in-situ (on surface) to tether the sensor molecule to CNTs.

In the methods and devices of the present invention DNA used to coat CNTs, preferably SWCNTs, is typically a (GTT)$_3$G-NH$_2$ coated on SWCNTs having 7,6 chirality. The free amino group of (GTT)$_3$G-NH$_2$ may be used as the functional group for coupling sensor molecules.

Data in the Inventors' laboratory has provided evidence of the applicability of this approach demonstrating the electrical detection of DNA hybridisation and dehybridisation events on individual CNTs in device configurations. Control experiments have been performed using non-complementary DNA sequences but no significant current variation was observed. Most importantly, as a proof-of-concept, the Inventors functionalised SWCNTs with cortisol and neuropeptide-Y selective aptamers, and employed devices for the detection of those hormones, that are correlated to several stress and neuro-trauma conditions. This allowed the detection in real-time physiological relevant concentrations of cortisol (from a few hundred nM down to 10 nM) and neuropeptide Y (down to 100 pM) in nanoscale devices. Furthermore, detection of multiple target molecules have been demonstrated using a single biosensor device of the invention, as set out in the Examples. Data are set out in the Examples below.

Sensor Molecules

In the present methods and biosensor devices of the invention, target molecules are detected using sensor molecules. A sensor molecule is any molecule capable of detecting a target molecule/analyte in a sample.

A preferred molecule to be used in a sensor disclosed herein is an aptamer. Aptamers may be peptide or oligonucleotide aptamers. Preferred aptamers are oligonucleotide aptamers. Oligonucleotide aptamers are single stranded DNA (ssDNA) or single stranged RNA (ssRNA) molecules that can bind to a wide variety of entities, such as proteins, metal ions, chemicals, small organic molecules, and cells. Aptamers are well known in the field as alternatives to antibodies in terms of their high affinity, high selectivity, and high specificity for targets. Furthermore, aptamers have the advantage of high specificity, small size, relative ease of synthesis and relative low cost.

In addition, aptamers can be reused by washing with high salt (e.g. Urea or Guanidine Hydrochloride) which leads to conformational changes that result in the release of any bound targets. As such, a sensor, wherein the biomolecule is an aptamer, can be repeatedly reused following high-salt washes.

Examples of aptamers which may be used in a biosensor disclosed herein include, but are not limited to, aptamers that are specific to neuropeptide Y, aptamers that are specific to cortisol and aptamers that are specific to DHEAS: respectively 5'-AGC AGC ACA GAG GTC AGA TGC AAA CCA CAG CCT GAG TGG TTA GCG TAT GTC ATT TAC GGA CCT ATG CGT GCT ACC GTG A-3' for Neuropeptide-Y detection; 5'-GTT GTT GTT GGGA ATG GAT CCA CAT CCA TGG ATG GGC AAT GCG GGG TGG AGA ATG GTT GCC GCA CTT CGG CTT CAC TGC AGA CTT GAC GAA GCT T-3' for Cortisol detection; and 5'-CTG CTC TCG GGA CGT GGA TTT TCC GCA TAC GAAGTT GTC CCG AG-3' for DHEAS detection.

Such aptamers can be used for diagnosis and/or monitoring of conditions states such as neurotrauma, and stress.

Any aptamer specific to analytes known as indicators/predictors of physiological/pathological conditions can also be used for the assembly of biosensor devices for the diagnosis and/or monitoring of the associated conditions. A combination of aptamers can be used on a biosensor device for the detection of multiple conditions. Moreover, it is possible to produce patient-specific/bespoke biochips with a combination of different aptamers for the diagnosis and/or monitoring of conditions.

Other biomolecules that can be used in a sensor disclosed herein in place of or in addition to aptamers include but are not limited to proteins such as enzymes and antibodies, other nucleic acid-based molecules such as peptide nucleic acid (PNA), antibodies, enzymes and small molecules and/or complexes comprising any combination of such sensor molecules. A combination of aptamer and protein can also be used in a sensor disclosed herein for the detection and/or monitoring of differing conditions. For example, glucose oxidase can be used in a sensor disclosed herein for the detection of glucose to aid diagnosis and/or the monitoring of diabetes.

Furthermore, distinct aptamers, distinct proteins, and/or distinct small molecules or any combination thereof, specific for the same target can be used for increased confidence in diagnosis and/or monitoring of a target molecule/analyte.

Target Molecules

Target molecules/analytes to be detected include but are not limited one or more selected from the group consisting of proteins (e.g. hormones, enzymes, cytokines, neuropeptides, cancer antigens, antigens derived from a microorganism such as a bacterium, a virus or a fungus), cytotoxins such as lipopolysaccharides, peptides, amino acids, nucleotides, chemicals, drugs, vitamins, organic compounds, inorganic compounds, antibodies. The target molecule can be a biomarker, preferably a biomarker associated with a physiological condition. The target molecule can be a biomarker associated with a disease state, a fever or an infection.

The analytes to be detected include but are not limited to neuropeptide Y, cortisol, DHEAS and/or glucose or any combination thereof.

A biosensor unit of a device of the invention is capable of detecting a specific target molecule with a high degree of sensitivity. A biosensor unit is capable of detecting a target molecule at a concentration of 300 pM or less, 250 pM or less, 200 pM or less, 150 pM or less, 100 pM or less, 90 pM or less, 80 pM or less, 70 pM or less, 60 pM or less, 50 pM or less, 40 pM or less, 30 pM or less, 20 pM or less or 10 pM or less. Preferably a biosensor unit is capable of detecting a target molecule at a concentration of 100 pM, or less than 100 pM.

Coupling of Sensor Molecules to CNTs

The coupling of specific nucleotides on chemical vapor deposition (CVD)-grown CNTs in FET configurations for electrical biosensing/detecting purposes has been been implemented with different chemistries by So et al. (*JACS*, 2005, 127 (34), 11906-11907), S. Sorgenfrei et al. (*Nat Nano* 2011, 6, 126), Ordinario et al. (*Anal. Chem.*, 2014, 86 17, 8628-8633), and by Liu et al. (*Angew. Chem. Int. Ed. Engl.*, 2011, 50 (11), 2496-502) on electron-beam cut CNTs. Additionally Weiss and co-workers attached proteins on CNT transistors for protein monitoring (Chot et al. *Science* 2012, 335, 319, and Pugliese et al. (*JACS* 2015, 137, 9587-9594). Moreover, Landry et al. employed a DNA wrapping procedure to optically detect protein efflux from microorganisms (*Nat Nano* 2017, 12, 368-377).

Various molecular linkers may be used in the biosensor devices disclosed herein for the coupling of sensor molecules to CNTs. Different molecular linkers can be chosen to vary the length of the coupling to CNTs and/or geometry (e.g. multi-terminal or circular) of the CNT assembly as required.

Such molecular linkers include but are not limited to hexamethylenediamine (HMD), and polyproplenimine tetramine dendrimers, poly(aminidoamine) (PAMAM) dendrimers with an ethylenedimaine core. Examples of phenyl ring-containing molecular linkers that can be used in sensors are p-phenylenediamine (PPD), and benzidine, 4,4-diamino-p-terphenyl (terphenyl).

Sensor molecules may be conjugated to azide or any other compound or molecule that can be used in "click chemistry" techniques or coupling reactions (including via supramolecular approaches, e.g. via base-pair intercalation). This enables biomolecules such as aptamers, and proteins etc. to be tethered to nucleic acid by amidation reaction of the functional group of the biomolecule with the coupling group present in the nucleic acid.

In alternative methods, the nucleic acid can be functionalised with other linker moieties, including proteins and protein:protein complexes. For example, nucleic acids can be functionalised/conjugated with biotin, and biomolecules conjugated to streptavidin. Biomolecules can then be coupled to nucleic acid via high affinity interactions (biotin:streptavidin interactions). Modified versions of biotin and avidin can also be employed to reverse binding. For example, Desthiobiotin, a biotin analogue can be used which can be easily displaced by biotin. As such, devices can be readily reused with different biomolecules. Other equivalent moieties/complexes are envisaged.

Target molecules may comprise nucleic acid binding domains, e.g. created by genetic fusion or chemical coupling. Target molecules may then bind to nucleic acid via the nucleic acid binding domain. Thus in such an embodiment the nucleic acid is inherently functionalised via its specific nucleotide sequence.

Substrates Comprising Electrodes

The substrate on which CNTs, preferably SWCNTs, are to be immobilised may be any suitable substrate.

Preferably, the substrate on which CNTs, preferably SWCNTs, are to be immobilised comprises a $SiO_2$ surface, or a flexible substrate such as paper, poly-(ethylene terephthalate), polycarbonate, polyethylene, Naphthalate and polyimide In a most preferred embodiment of the invention, the substrate is a $SiO_2$ surface functionalised with a polyethylene glycol (PEG) silane (typically 400-600 MW).

In preferred embodiments of the invention, the substrate comprises pre-patterned electrodes, preferably wherein the electrodes are metallic electrodes, more preferably wherein the electrodes are metal electrodes e.g. gold (Au) electrodes.

It is also possible to manufacture electrodes on surfaces de novo by using procedures known in the art, such as lithographic and etching techniques to create electrodes for use in the methods and devices described herein.

Prior to CNT immobilisation, electrodes of a pair should be provided so that their terminal ends are separated to form a gap. CNTs are then immobilised such that the one or more CNTs bridge the gap and thus form an electrical connection between electrodes of a pair or more.

Substrates can be structured such that the biosensor device is configured as a field effect transistor (FET) and provided with source (S), drain (D) and gate (G) terminals. An example of this is depicted in FIG. 5 (lower panel).

In biosensor devices of the invention comprising multiple biosensors per unit, drain terminals of each biosensor of a given unit may be connected in common. Similarly, source terminals of each biosensor of a given unit may be connected in common. In this configuration it is possible to address each biosensor unit simultaneously.

In biosensor devices of the invention the drain terminals of each biosensor of the device and/or the drain terminals of each biosensor unit of the device may be connected in common (e.g. as depicted in FIG. 5, lower panel). In biosensor devices of the invention the source terminals of each biosensor of the device and/or the source terminals of each biosensor unit of the device may separated (e.g. as depicted in FIG. 5, lower panel). The gate electrode is connected to the conductive doped silicon layer.

Biosensor devices of the invention may be manufactured in accordance with the assembly methods disclosed herein. Such methods include the sequential immobilisation of first CNTs for the detection of a first target molecule followed by immobilisation of second CNTs for the detection of a second target molecule, optionally followed by one or more cycles of immobilising further CNTs for the detection of further target molecules. Between assembly cycles the substrate is washed to remove non-immobilised CNTs prior to the next cycle of immobilisation. Any suitable wash buffer may be used, typically DI water is used. The wash buffer should be a mild buffer in that it maintains sensor molecules coupled to nucleic-acid coated CNTs.

Immobilisation of Nucleic Acid Wrapped CNTs at Electrode Junctions

The invention relates to biosensor devices wherein CNTs, preferably SWCNTs, are immobilised between two electrodes of a pair such that each CNT forms an electrical contact between electrodes of a pair.

In preferred embodiments of the invention, CNTs, preferably SWCNTs, are immobilised on substrates by dielectrophoresis (DEP).

DEP protocols have been described by Li et. al., (*Nanoscale Res. Lett.*, 2010, 5, 1072) and Vijayaraghavan (*Phys. Status Solidi B*, 2013, 250, 2505).

As described herein, nucleic acid-coated CNTs may be immobilised by DEP between two electrodes, such as pre-patterned metallic electrodes, e.g. on a silicon dioxide ($SiO_2$) surface functionalised with a polyethylene glycol silane. Alternatively, it is possible to first coat CNTs with nucleic acid, and then immobilise CNTs via DEP on electrode pairs, and then perform coupling reactions in-situ (on surface) to couple sensor molecules to the nucleic acid coated CNTs.

The assembly (immobilisation) of CNTs between electrodes of a pair of electrodes may be induced via DEP by an alternative voltage bias applied to the electrodes. By separately addressing different electrodes pairs, it is possible to immobilise n aptamer-functionalised CNTs, preferably SWCNTs, on n types of different electrodes pairs via DEP.

The organization of DNA-coated CNTs from solution to surfaces in parallel 2D device configurations with different sensor molecules, such a aptamers, on the same biosensor device, allows for the fabrication of multifunctional, high-throughput biosensor devices with parallel multi-purpose sensing capability. The electronic biosensor devices prepared in this fashion can withstand and respond to various environmental changes depending on the different sensor molecules employed.

Upon recognition of a target molecule, its specific cognate sensor molecule may change conformation and may induce a change in electrical response of the CNT of the device.

Order of Assembly of Devices

Biosensor devices of the invention may be assembled by a variety of methods comprising different orders of steps. Any suitable order of steps is envisaged.

Biosensor devices of the invention may be assembled by methods comprising:
  (i) performing a first assembly cycle comprising:
    A. providing a population of first carbon nanotubes (CNTs) coated with nucleic acid molecules, wherein nucleic acid molecules are functionalised with functional groups suitable for coupling first sensor molecules to nucleic acid molecules, wherein each first sensor molecule is capable of binding to a first target molecule;
    B. providing a substrate comprising a plurality of electrode pairs;
    C. immobilising one or more coated CNTs between separate electrode pairs, wherein each CNT forms an electrical connection between electrodes of a pair;
    D. coupling one or more first sensor molecules to the nucleic acid of each coated CNT, wherein each first sensor molecule is capable of binding to a first target molecule;
    E. washing the substrate to remove non-immobilised coated CNTs; and
  (ii) performing a second assembly cycle comprising repeating steps (A) to (E), wherein in repeat step (A) the population of first CNTs is replaced with a population of second CNTs, and wherein functional groups are suitable for coupling second sensor molecules to nucleic acid molecules; and wherein in repeat step (D) the one or more first sensor molecules are replaced with one or more second sensor molecules, wherein each second sensor molecule is capable of binding to a second target molecule.

Such a method may further comprise performing one or more further assembly cycles to assemble a biosensor device comprising three or more biosensor units; wherein each further assembly cycle comprises repeating steps (A) to (E), wherein in each repeat step (A) the population of first or second CNTs is replaced with a further population of CNTs, and wherein functional groups are suitable for coupling further sensor molecules to nucleic acid molecules; and wherein in each repeat step (D) the first or second sensor molecules are replaced with further sensor molecules, wherein in each further assembly cycle each one of the further sensor molecules is capable of binding to a further and different target molecule.

In any of these methods in any step (A) the nucleic acid molecules can be functionalised with functional groups before or after the population of first, second or further CNTs are coated with nucleic acid molecules.

In any assembly cycle of any of these methods, step (D) of coupling one or more sensor molecules to nucleic acid of each coated CNT can be performed after step (A) and before step (C).

Any of these assembly methods may be performed in accordance with any further steps described herein.

In any assembly cycle of any of the methods, the steps of coating the CNTs and coupling one or more sensor molecules to nucleic acid of each coated CNT can be performed as a prior step. Thus the methods of the invention also relate to additional assembly methods comprising:

(i) performing a first assembly cycle comprising:
  A. providing a population of first carbon nanotubes (CNTs) coated with nucleic acid molecules, wherein one or more first sensor molecules have been coupled to the nucleic acid of coated first CNTs, wherein each first sensor molecule is capable of binding to a first target molecule;
  B. providing a substrate comprising a plurality of electrode pairs;
  C. immobilising one or more coated and coupled CNTs between separate electrode pairs, wherein each CNT forms an electrical connection between electrodes of a pair;
  D. washing the substrate to remove non-immobilised coated CNTs; and
(ii) performing a second assembly cycle comprising repeating steps (A) to (D), wherein in repeat step (A) the population of first CNTs is replaced with a population of second CNTs which have been coated with nucleic acid molecules to which second sensor molecules have been coupled, wherein each second sensor molecule is capable of binding to a second target molecule.

Any of these additional assembly methods may further comprise performing one or more further assembly cycles to assemble a biosensor device comprising three or more biosensor units; wherein each further assembly cycle comprises repeating steps (A) to (D), wherein in each repeat step (A) the population of first or second CNTs is replaced with a further population of CNTs which have been coated with nucleic acid molecules to which further sensor molecules have been coupled, wherein each further sensor molecule is capable of binding to a further and different target molecule.

Any of these additional assembly methods may be performed in accordance with any further steps described herein.

Electrical Operation of Biosensor Units

Biosensor devices of the invention are capable of detecting target molecules in a sample when a target molecule of the sample is contacted with a sensor molecule of a biosensor of the device.

Typically, the change in conformation or other property of the sensor molecule upon interaction with target molecule will affect the electric response of the CNTs in the device.

Preferably, the current (I) of the device is measured at particular gate voltages. Changes in the current before and after application of the sample may be observed if the target molecule is present in the sample and contacts the sensor molecule. For each target molecule to be detected, the specific biosensor unit of the device will be calibrated before sample application, e.g. by drop-casting solutions of the specific target molecule at specific concentrations onto biosensors such as described in the Examples (e.g. FIG. 11). Gate voltages will be optimized and calibrated in this way for a given target molecule and for each device in order to take into account various parameters, such as the number of biosensors per unit, the number of CNTs immobilised across each pair of electrodes of a biosensor, the number of sensor molecules coupled to each CNT of a biosensor, the electrical effect on the CNT(s) (and thus biosensor) of the molecular interaction between target molecule and sensor molecule and so on. Typically, the gate voltage will be between −10 volts to +10 volts.

Samples

The devices and methods of the invention are capable of detecting analytes in any suitable sample.

Often, samples may be samples taken from an individual. For example, a sample may be a sample of a biological fluid taken from an individual, such as including but not limited to blood, serum, plasma, saliva, urine, mucous, vomit, faeces, and/or sweat. Other examples of biological fluids can be found here https://en.wikipedia.org/wiki/Body_fluid.

EXAMPLES

The following Examples are provided to illustrate the invention but not to limit the invention. In the following Examples, all values may be considered approximate, and the methods may be altered to achieve the same results within the context of routine experimental variation and optimisation.

Example 1: Preparation of DNA Wrapped Single Walled Carbon Nanotubes in Solution DNA wrapped Single Walled Carbon Nanotubes (SWCNTs) dispersed in deionized (DI) water may typically be prepared in accordance with the following methods. Additional methods are provided in Palma et al., (*J. Am. Chem. Soc.* 2013, 135, 8440-8443).

1 mg of SWCNTs (HiPco nanotube, Carbon Nanotechnologies) was suspended in 1 ml aqueous DNA (Integrated DNA Technologies) solution (e.g. 1 mg ml$^{-1}$ ssDNA solution e.g. $(TCG)_4TC$, or $GTT_3G-NH_2$, 0.1 M NaCl), and in some experiments an appropriate pH buffer). The mixture was kept in an ice-water bath and sonicated (Sonics, VC130 PB) for 90 min at a power level of 3 W. After sonication, the samples were divided into 0.1 ml aliquots, and centrifuged (Eppendorf 5415C) for 90 min at 16,000 g to remove insoluble material, leaving DNA-dispersed nanotube solutions at a mass concentration in the range of 0.2 to 0.4 mg ml$^{-1}$. Segments of defined length (average length of 147.7±92.8 nm) may be obtained by size exclusion chromatography, e.g. at a final nanotube concentration of 40 μg/mL. All concentrations may be determined by the integration of absorbance in the E11 optical transition as a concentration proxy.

Example 2: Coupling of Sensor Molecules to Functionalised Wrapped SWCNTs

SWCNTs can be functionalised with sensor molecules by coupling sensor molecules to functionalised SWCNTs in accordance with the following methods.

As described herein sensor molecules may comprise any molecule capable of detecting a target molecule in the context of a biosensor device of the present invention. Exemplary sensor molecules as described herein are aptamers. It will be appreciated that other methods may be used to couple different sensor molecules to functionalised SWCNTs.

Aptamers may be coupled to SWCNTs by performing the following exemplary basic scheme (see also Example 3):

(A) modify DNA (e.g. $GTT_3G-NH_2$) coated SWCNTs with BCN-NHS to obtain $GTT_3G$-BCN (amidation reaction);
(B) wrap SWCNTs, e.g. 7,6 SWCNTs, with the obtained $GTT_3G$-BCN; and
(C) functionalise wrapped SWCNT with different aptamers separately (e.g. via click chemistry reactions).

As described herein, the methods may be performed differently. For example, SWCNTs may be first wrapped with DNA and then functionalised.

Figure 1:
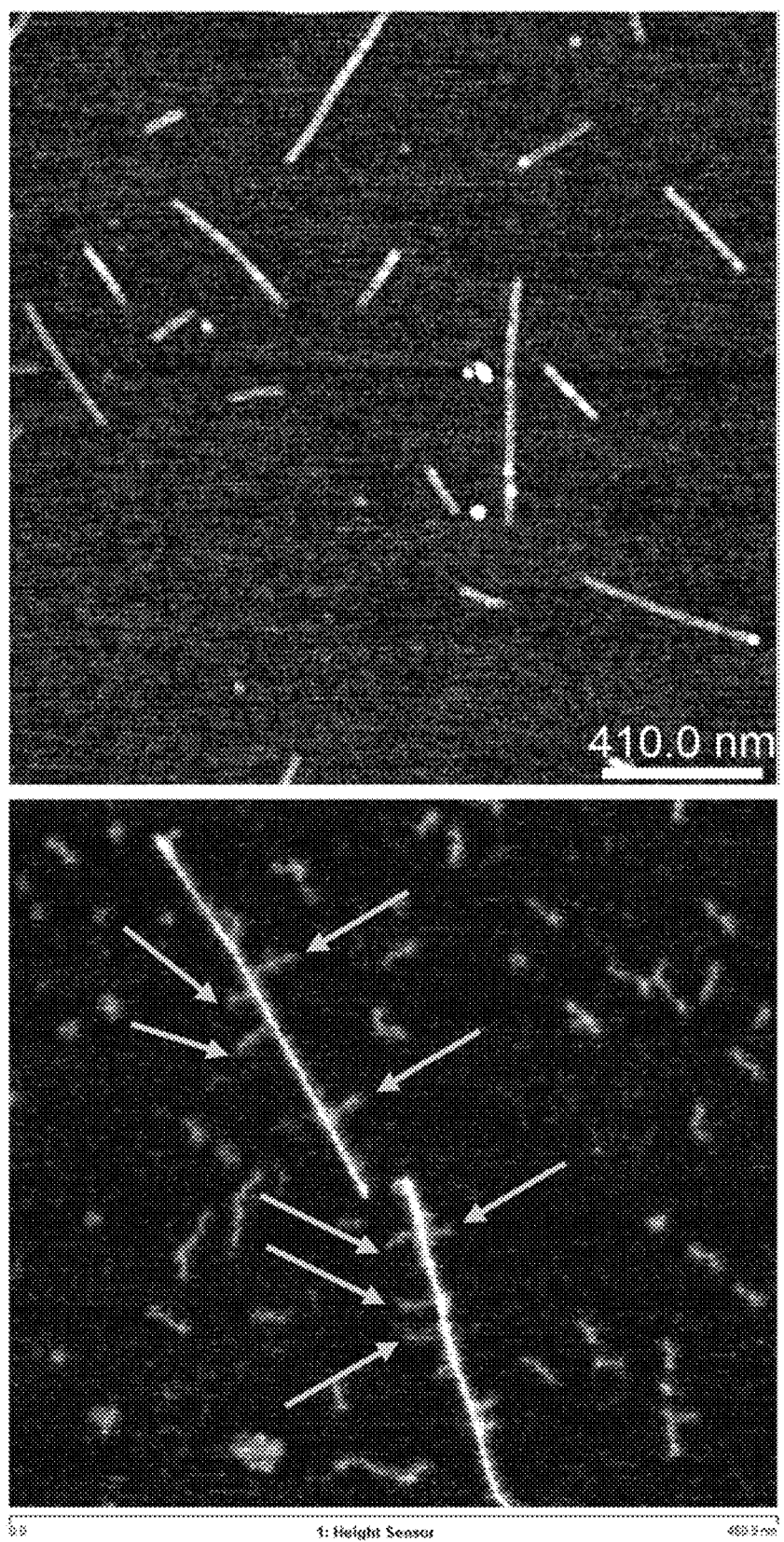
FIG. 1 shows atomic force microscopy (AFM) images of SWCNTs functionalised with aptamers before (top) and after (bottom) DNA hybridisation (shown with arrows).

To verify the successful functionalisation of SWCNTs with aptamers in solution, complementary DNA sequences may be used. After hybridisation of complementary DNA sequences to aptamers, the presence of double stranded DNA may be observed by atomic force microscopy (AFM). As shown in FIG. 1 (bottom panel), after DNA hybridisation it can be distinctly observed that there are protrusions from SWCNTs. It is estimated that about 3-5 aptamers are linked to SWCNTs per 100 nm of nanotube.

Figure 2:
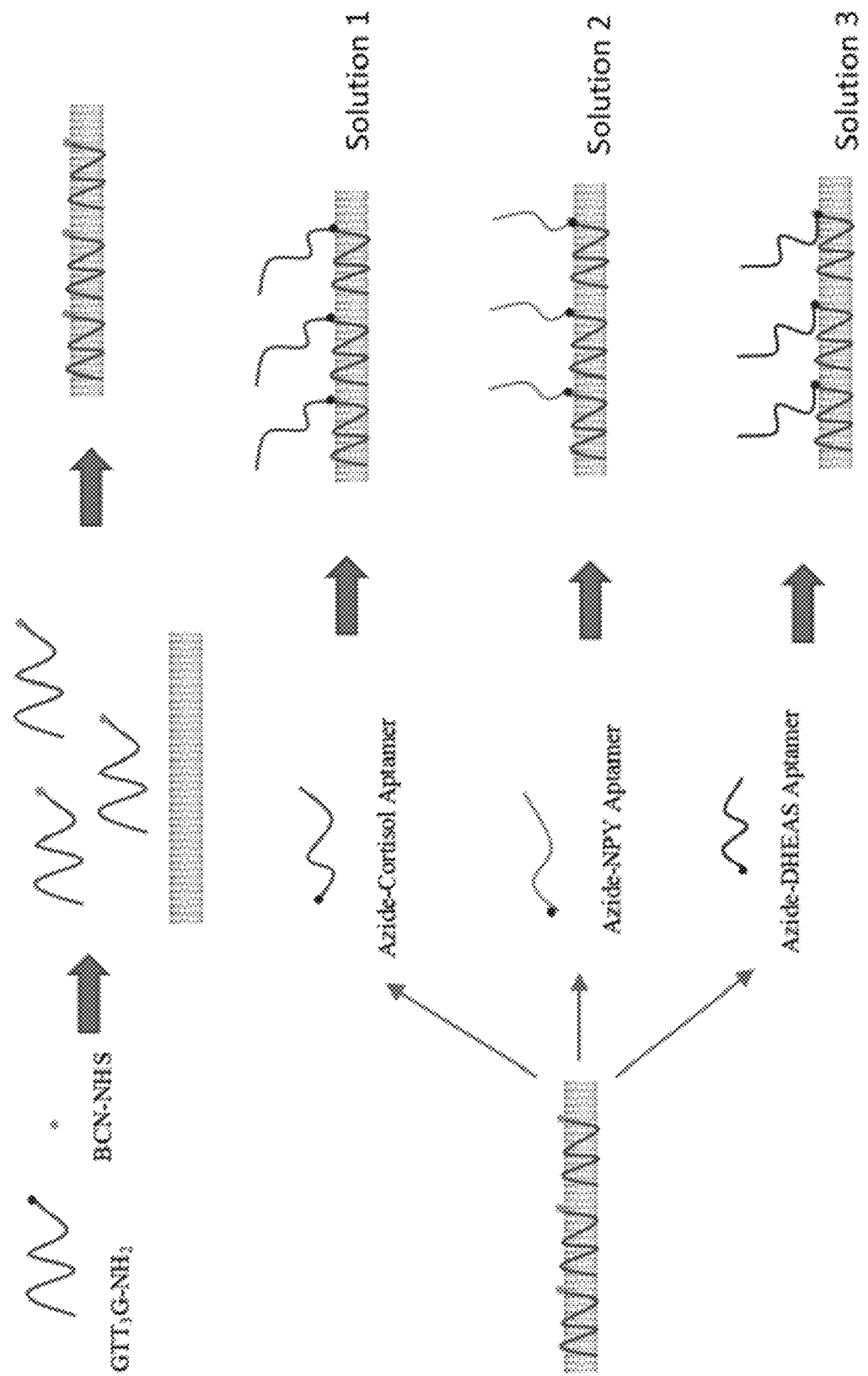
FIG. 2 shows an exemplary schematic of the functionalisation of SWCNTs with three different aptamers in solution.

An example schematic for the separate functionalisation of SWCNTs with three different aptamers in solution is shown in FIG. 2.

Example 3: Illustrative Fabrication Scheme for Biosensor Devices

A biosensor device according to the invention may be prepared using the following exemplary non-limiting methods.

(1) Coat CNTs, such as SWCNTs, with ssDNA such as $(GTT)_3G-NH_2$. In this case the nucleic is provided with a functional group—the terminal amino group.
(2) Perform an amidation reaction between the amino group on the CNT (provided by the DNA wrap) and bicyclononyne N-hydroxysuccinimide (BCN-NHS) (10 mM, 100 μL) in diphosphate dibase buffer (100 mM), overnight.
(3) Perform a "click chemistry" reaction between BCN and azide-modified sensor molecule (e.g. azide-modified cortisol binding aptamer, azide-modified neuropeptide-Y binding aptamer or azide-modified dehydroepiandrosterone sulphate (DHEAS) binding aptamer) in DPBS buffer, overnight.
(4) Functionalise a $SiO_2$ chip containing pre-patterned electrodes with a suitable coating such as polyethylene glycol silane.
(5) Immobilise the CNTs between the pre-patterned (e.g. Au) electrodes, preferably via DEP.
(6) A detection cycle may optionally be performed by drop casting on the chip a solution containing one or more target molecules for detection.

By electrically addressing different electrodes pairs, it is possible to immobilise n aptamer-functionalised SWCNTs on n kinds of different electrodes pairs via DEP.

For example, devices capable of detecting multiple analytes at specific concentrations can be assembled, e.g. devices capable of detecting cortisol, neuropeptide-Y and DHEAS.

To recover from the binding event, the sample can be immersed in a recovery solution, e.g. a solution of 6 M of guanidine hydrochloride or 8M of Urea in 50 mM Tris-HCl buffer pH=7.4.

The organization of the DNA-SWCNTs from solution to surfaces in parallel 2D device configurations with different aptamers on the same chip, allows for the fabrication of multifunctional, high-throughput bio-electronic devices with parallel multi-purpose sensing capability.

Notably, an alternative strategy is to perform steps (2) and (3), i.e. the functionalisation of the CNT with biorecognition elements, in-situ once the CNTs are already immobilised on surface, therefore after step (5) and before step (6).

Example 4: Study of the Electrical Response of Aptamer-Coupled SWCNTs

The electrical response of sensor molecules coupled to SWCNTs was studied, in this case using SWCNTs coupled to cortisol-binding aptamers.

Figure 6:
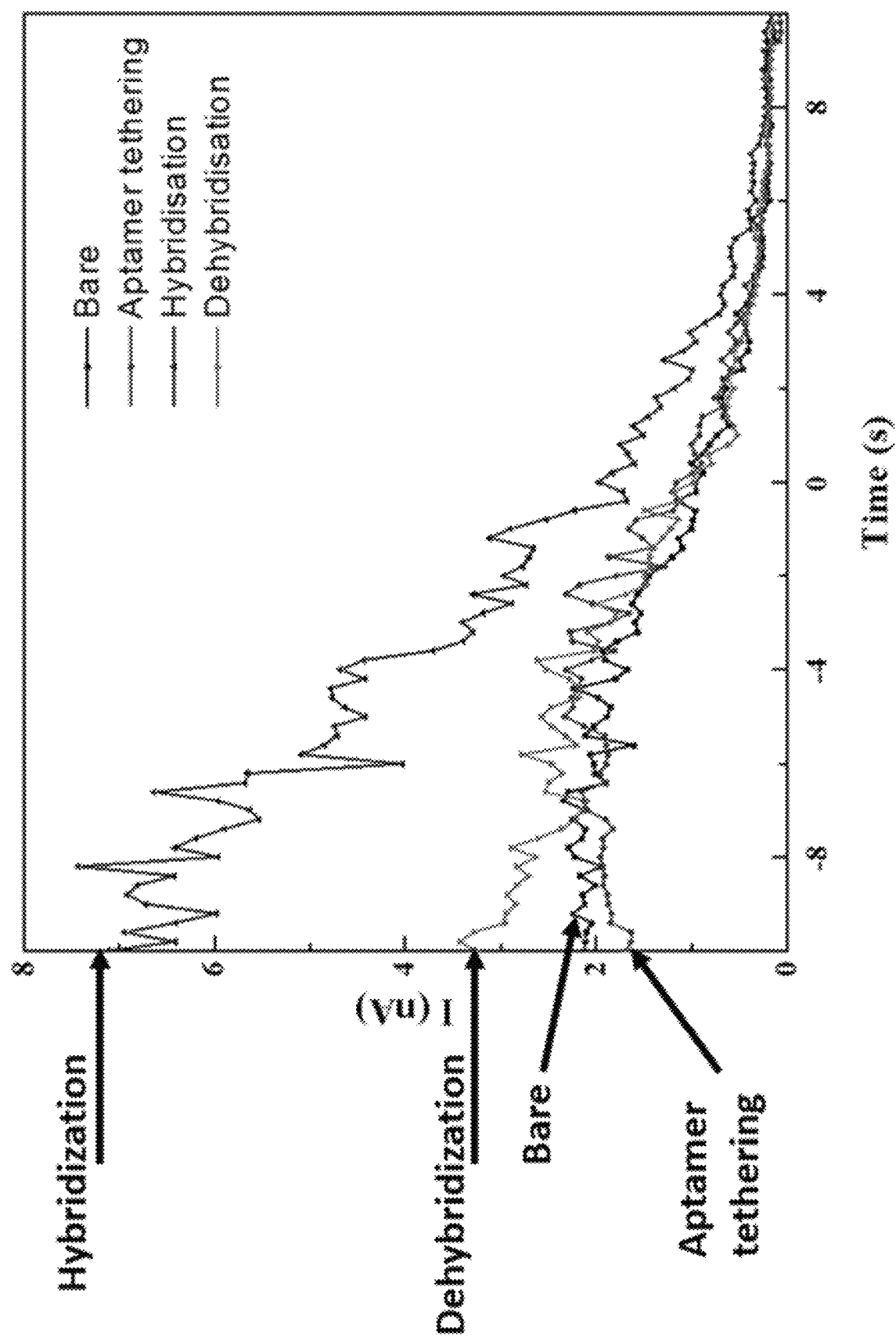
FIG. 6 shows hybridisation sensing using a biosensor device comprising cortisol binding aptamers.

As proof-of-concept, FIG. 6 shows traces corresponding to hybridisation sensing with an exemplary cortisol binding aptamer. FIG. 6 shows that the functionalisation of the SWCNT via chemical reaction with the cortisol binding aptamer does not affect its conductivity. In the presence of the complementary DNA for the cortisol binding aptamer, hybridisation occurs and an increase of the conductivity of the SWCNT is observed (upper trace). Rinsing the sample with 50% formamide/DI water solution leads to dehybridisation of the complementary DNA for the cortisol binding aptamer leading to a decrease in the conductivity of the SWCNT back to initial levels.

Example 5: Study of the Reversibility of the Electrical Response of Aptamer-Coupled SWCNTs The reversibility of detection of target molecules using biosensors of the invention was studied.

For these experiments, biosensors were assembled to detect the target molecule neuropeptide Y (NPY) using sensor molecules which in this case were NPY-binding aptamers. Biosensors were assembled as described herein.

Figure 7A:
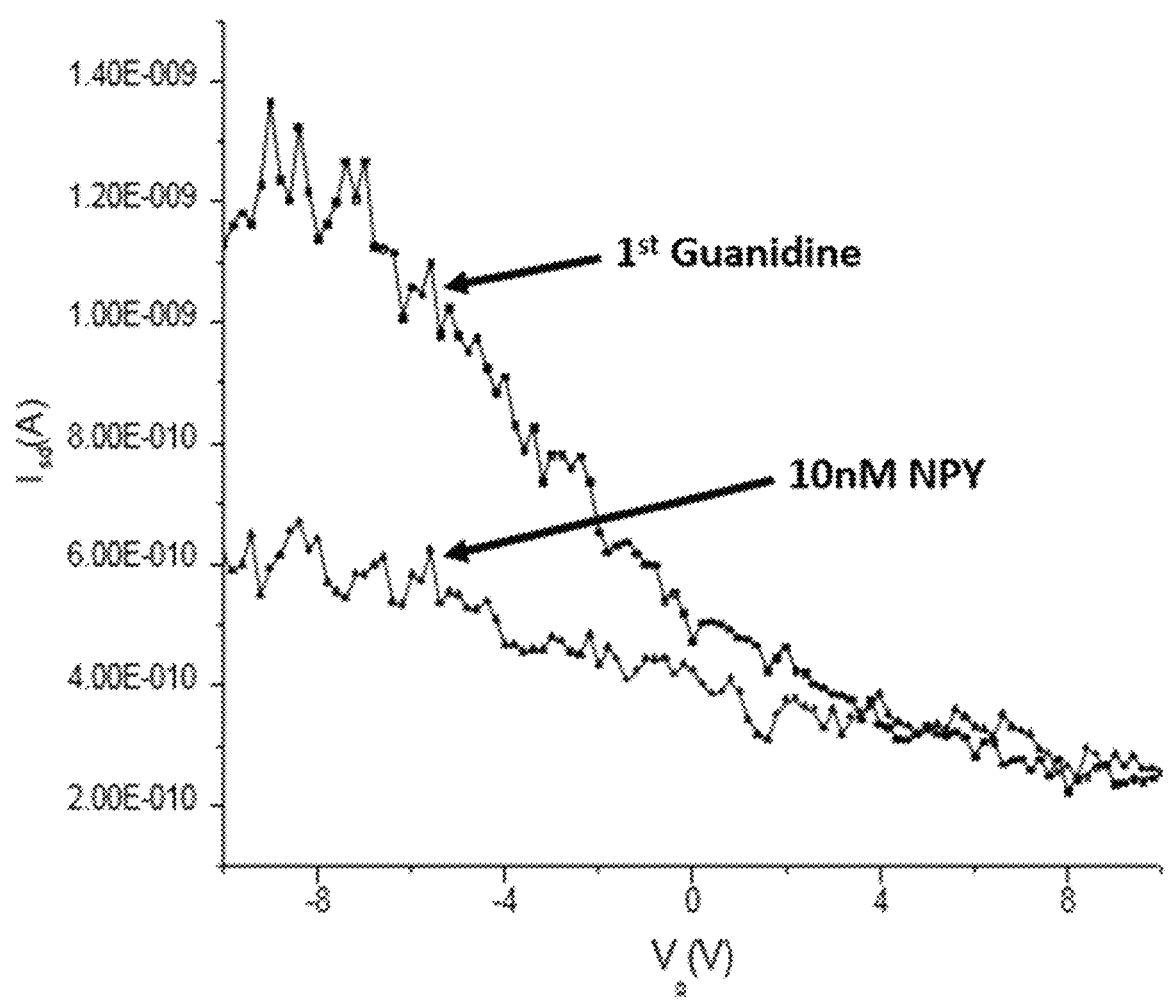
FIG. 7 shows the reversible detection of neuropeptide Y (NPY) using a biosensor device comprising NPY binding aptamers. Three different concentrations of NPY are used, 10 nM (FIG. 7A), 100 nM (FIG. 7B) and 100 pM (FIG. 7A).
Figure 7B:
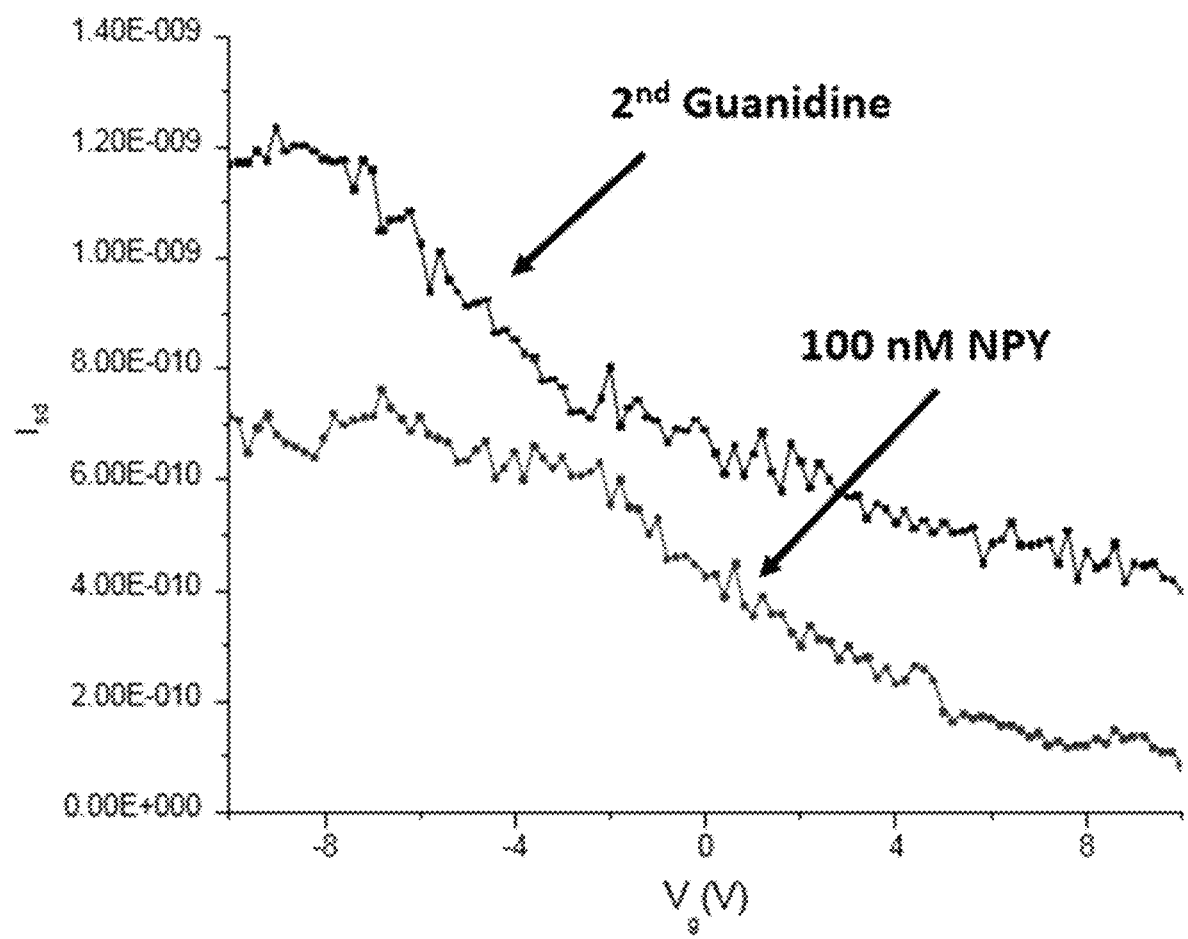
Figure 7C:
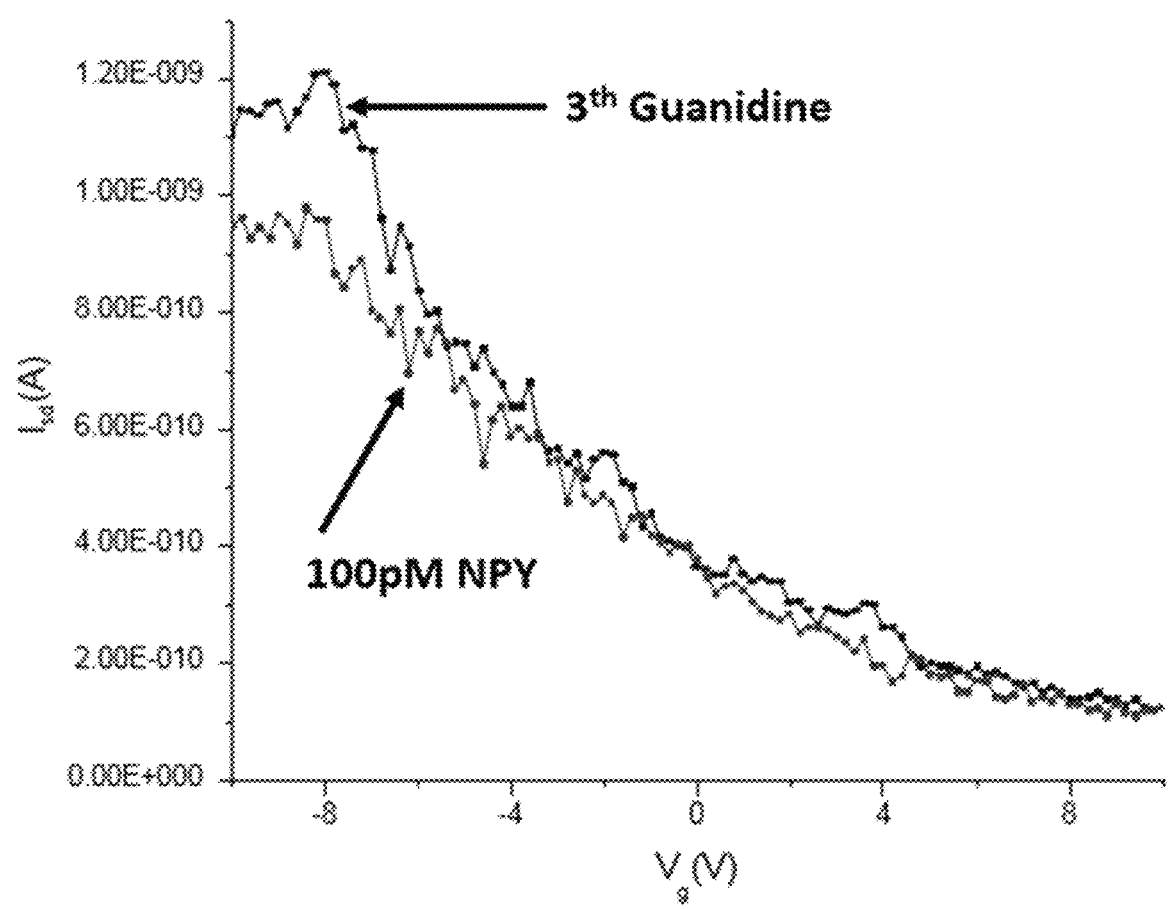

Three concentrations of NPY were measured. To recover from the binding event, the sample was immersed in a recovery solution which in this example was a solution of 6M of guanidine hydrochloride or 8M of Urea in 50 mM Tris-HCl buffer pH=7.4. The results are shown in FIGS. 7 (A), (B) and (C).

The binding of NPY results in the detectable decrease of the conductivity of the SWCNT as shown by the difference between the NPY and guanidine traces. After each cleaning/recovery via guanidine treatment, the electrical response of the sensor is returned to the initial baseline.

Example 6: Study of the Selectivity of the Electrical Response of Aptamer-Coupled SWCNTs The selectivity of the detection of two different target molecules using exemplary biosensor devices of the invention was studied.

Three biosensor devices were studied. A first biosensor device comprised biosensors capable of detecting cortisol only (using a cortisol-binding aptamer). A second biosensor device comprised biosensors capable of detecting NPY only (using a NPY-binding aptamer). A third biosensor device comprised biosensors capable of detecting cortisol and NPY. The third device was assembled with two biosensor units, one unit capable of detecting cortisol (using a cortisol-binding aptamer) and the other unit capable of detecting NPY (using a NPY-binding aptamer).

Selectivity was studied by measuring the electrical response with different solutions, a cortisol only solution, an NPY only solution, and a cortisol and NPY mixed solution. In each case detection of the target molecule was achieved by a drop in conductivity upon binding of the target molecule to the sensor molecule (aptamer).

Figure 8A:
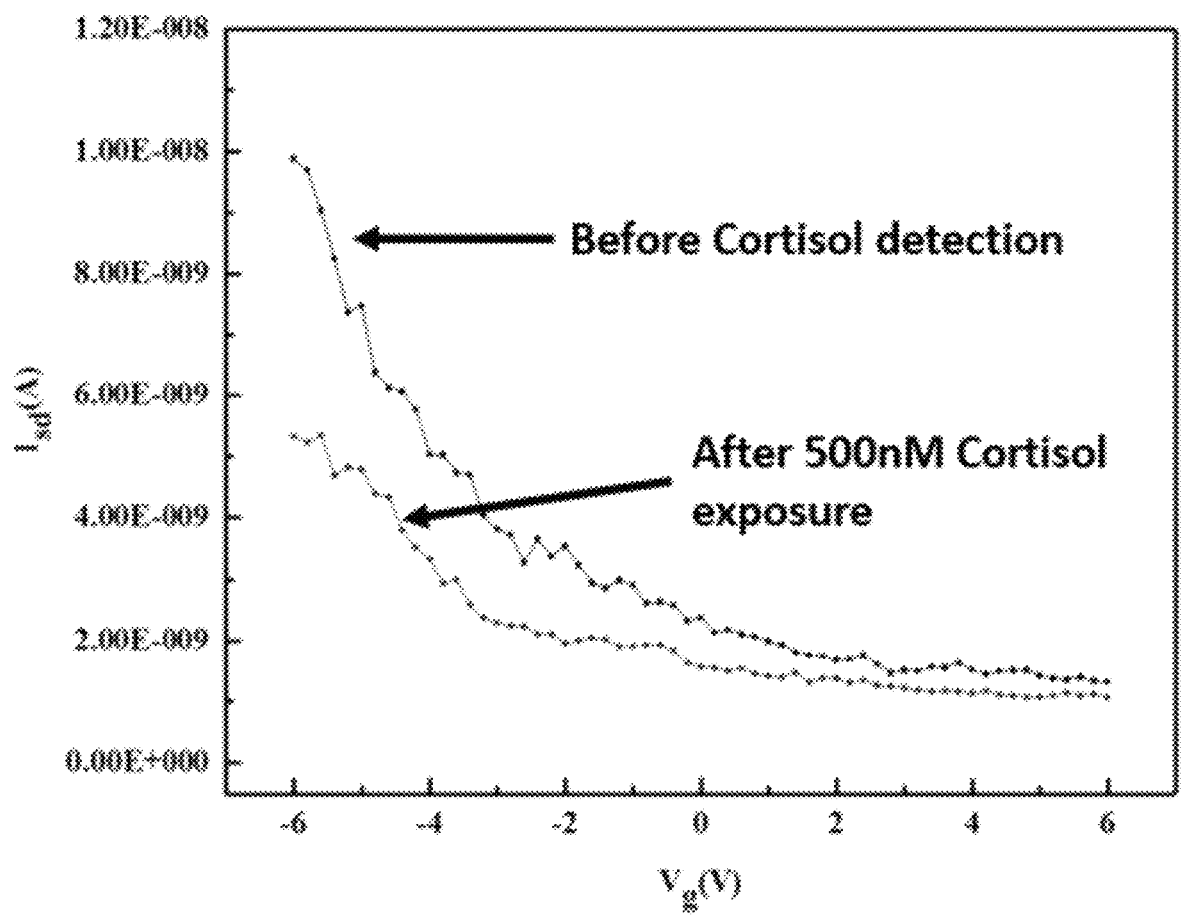
FIG. 8 shows the selective detection of cortisol using a biosensor device comprising cortisol binding aptamers. The Figure shows that the cortisol biosensor is capable of detecting cortisol (FIG. 8A) but is unresponsive to NPY (FIG. 8B). (Vsd=100 mV): the + sign indicates the addition/presence of the analyte of interest.
Figure 8B:
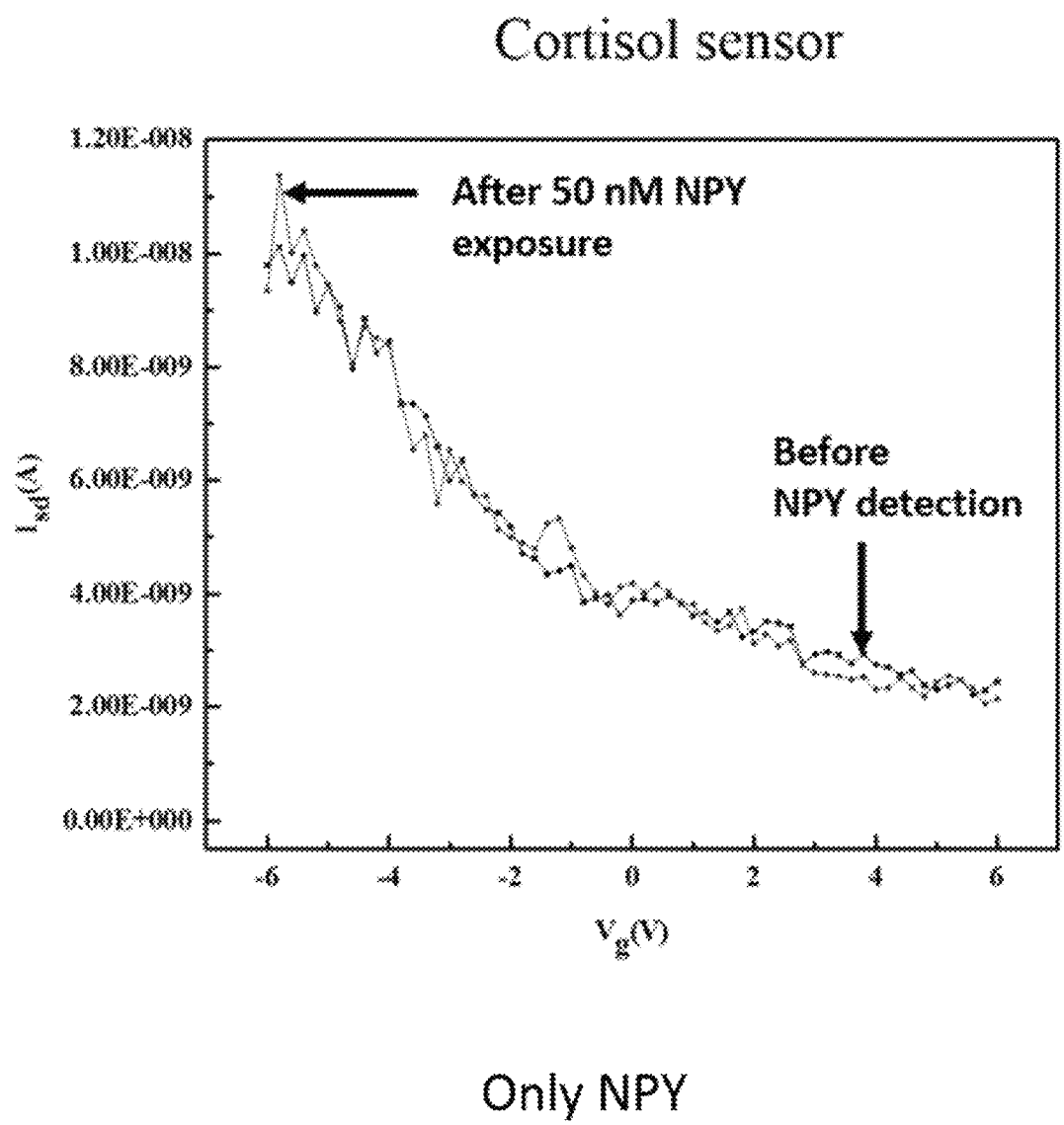

FIGS. 8 (A) and (B) show respectively that the cortisol-only biosensor device responded to cortisol but not to NPY.

Figure 9A:
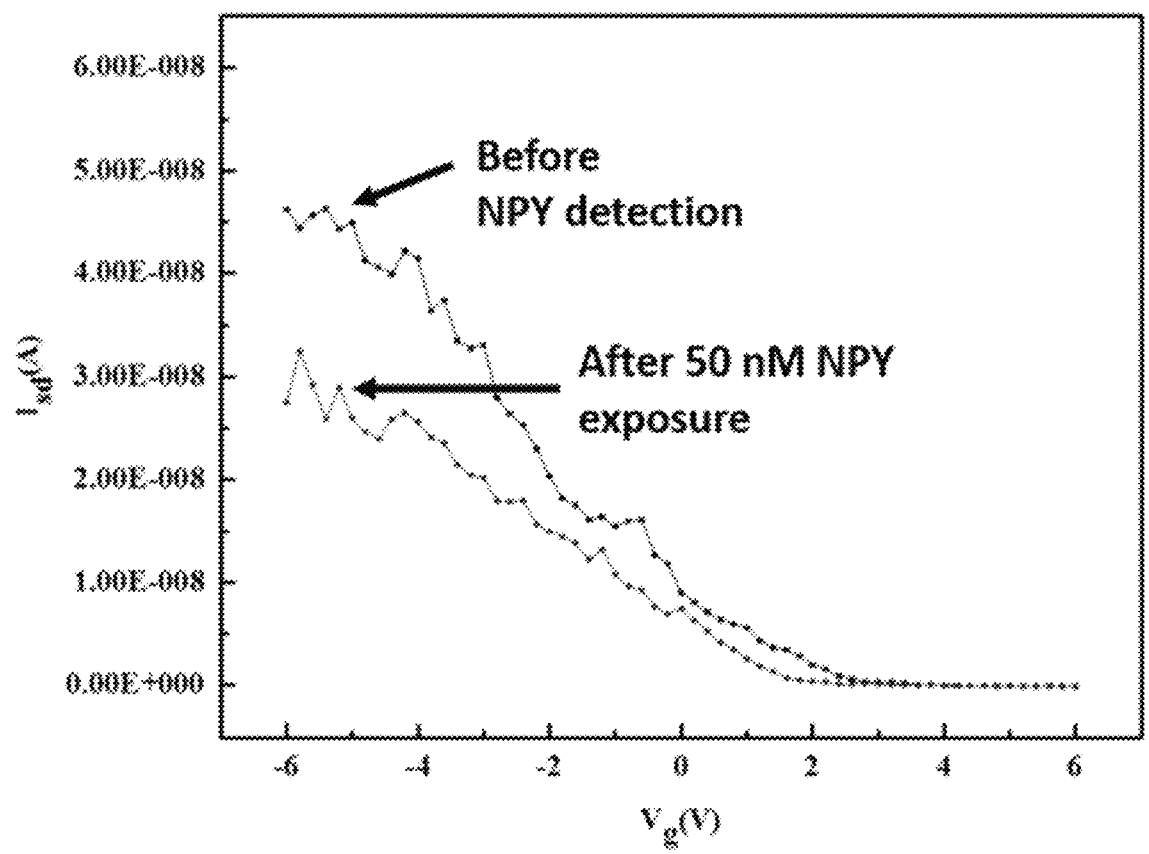
FIG. 9 shows the selective detection of NPY using a biosensor device comprising NPY binding aptamers. The Figure shows that the NPY biosensor is capable of detecting NPY (FIG. 9A) but is unresponsive to cortisol (FIG. 9B). (Vsd=100 mV): the + sign indicates the addition/presence of the analyte of interest.
Figure 9B:
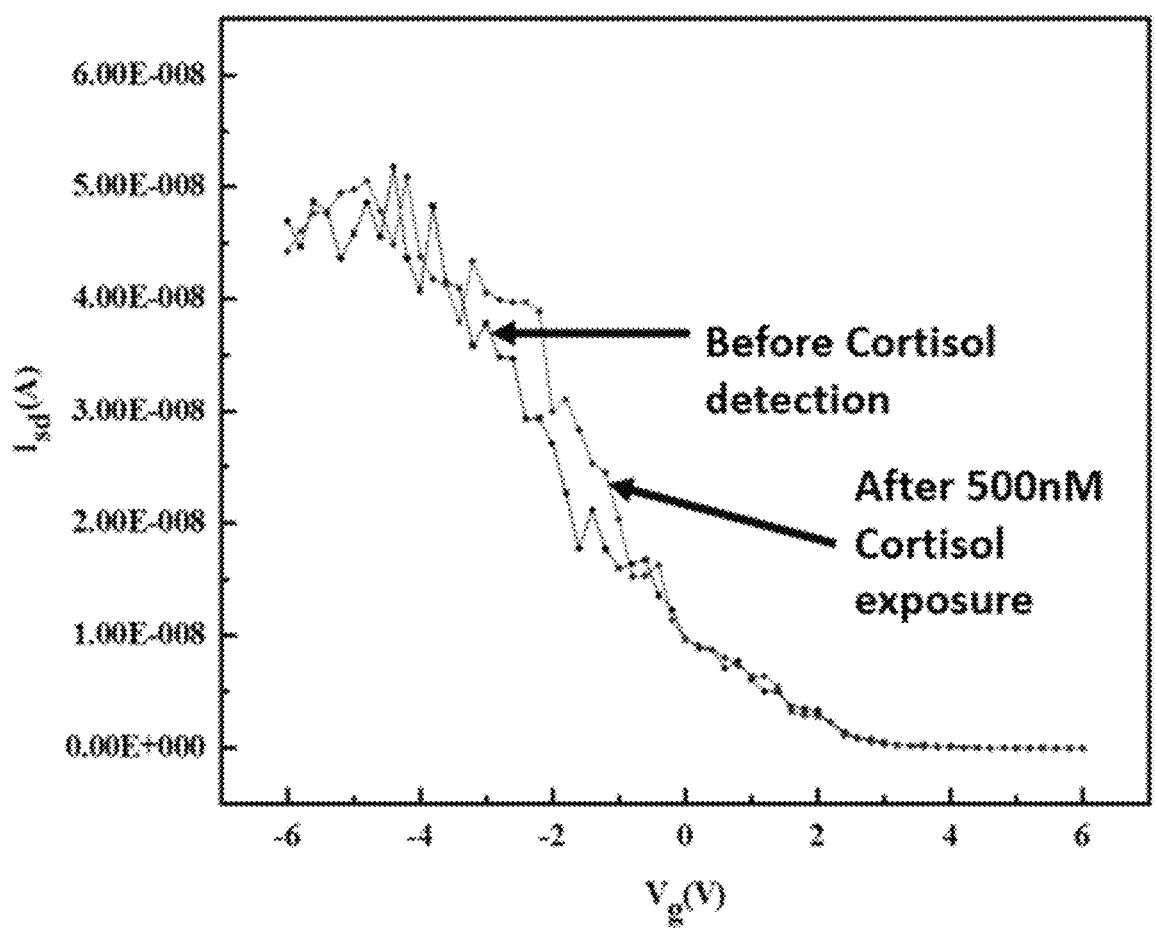

FIGS. 9 (A) and (B) show respectively that the NPY-only biosensor device responded to NPY but not to cortisol.

Figure 10A:
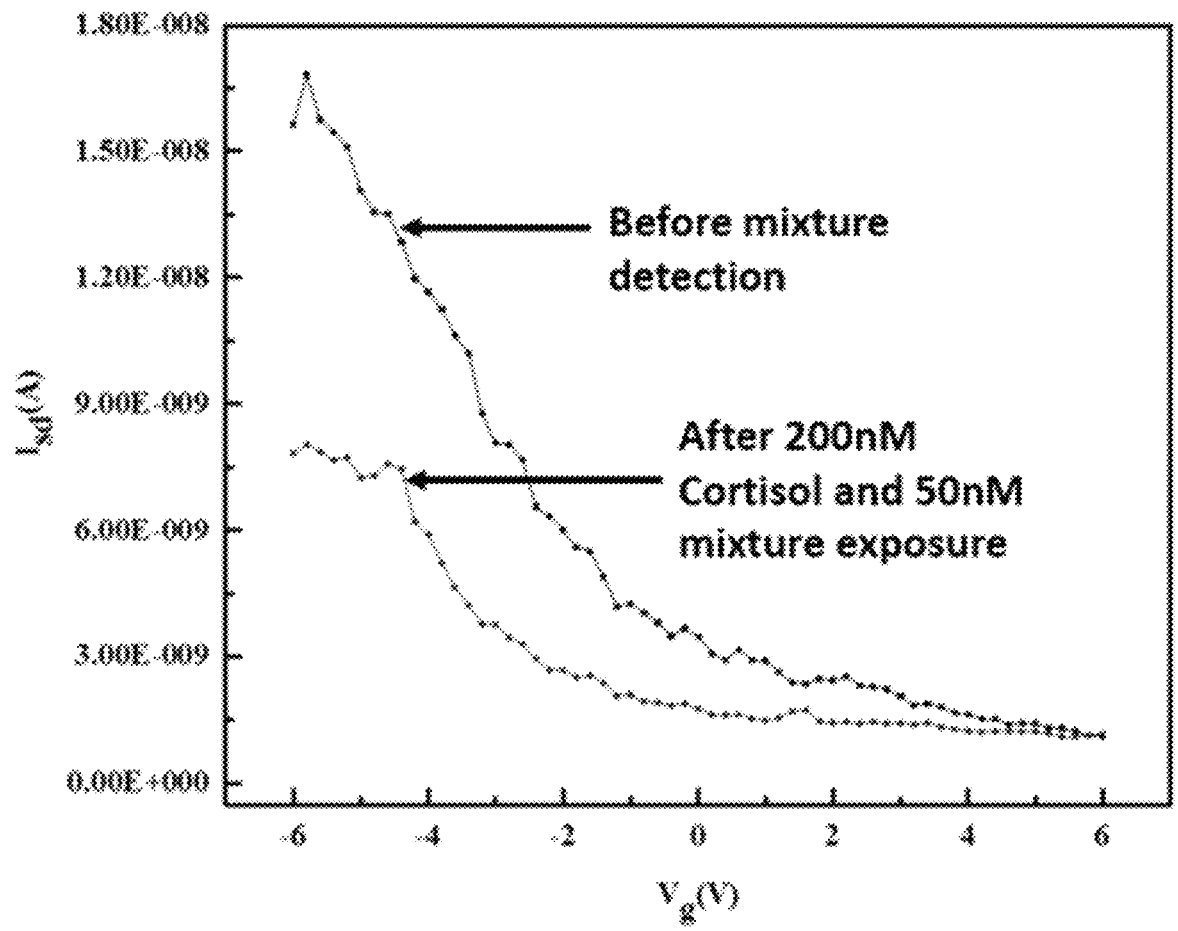
FIG. 10 shows the detection of NPY and cortisol using a biosensor device comprising a biosensor unit having biosensors comprising NPY binding aptamers and a biosensor unit having biosensors comprising cortisol binding aptamers. The Figure shows that the dual target molecule binding biosensor is capable of detecting cortisol (FIG. 10A) and NPY (FIG. 10B). (Vsd=100 mV): the + sign indicates the addition/presence of the analyte of interest.
Figure 10B:
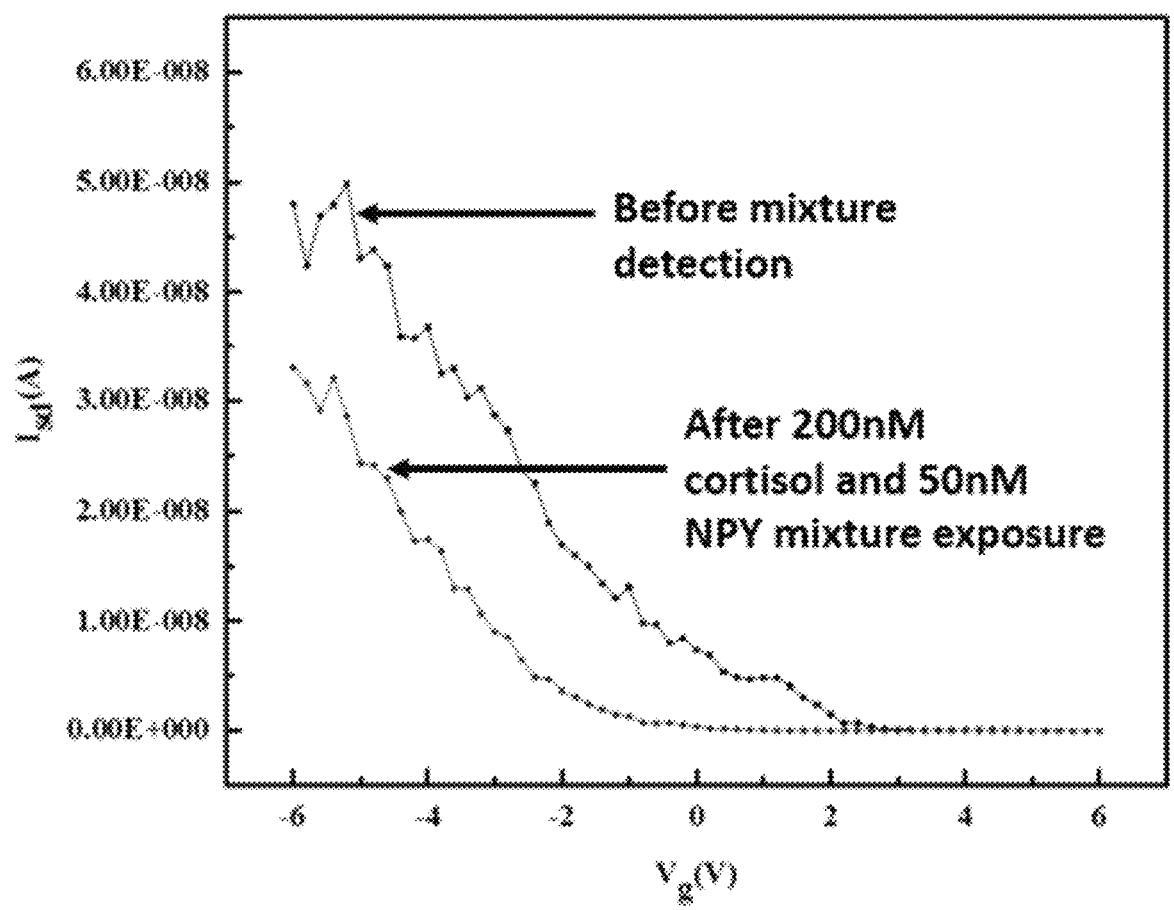

FIGS. 10 (A) and (B) show respectively that the cortisol/NPY dual-detection biosensor device responded to both cortisol and NPY.

Example 7: Separate Detection of Multiple Target Molecules Using a Single Biosensor Device A biosensor device capable of detecting three target molecule analytes on the same substrate was assembled in accordance with the methods described herein (i.e. a biosensor device having three biosensor units, each unit comprising biosensors capable of detecting a separate target molecule/analyte). The target molecules in this Example were cortisol, neuropeptide Y and DHEAS. In each case the sensor molecules were oligonucleotide aptamers capable of binding target molecules: respectively 5'-AGC AGC ACA GAG GTC AGA TGC AAA CCA CAG CCT GAG TGG TTA GCG TAT GTC ATT TAC GGA CCT ATG CGT GCT ACC GTG A-3' for neuropeptide-Y; 5'-GTT GTT GTT GGGA ATG GAT CCA CAT CCA TGG ATG GGC AAT GCG GGG TGG AGA ATG GTT GCC GCA CTT CGG CTT CAC TGC AGA CTT GAC GAA GCT T-3' for cortisol detection; and 5'-CTG CTC TCG GGA CGT GGA TTT TCC GCA TAC GAAGTT GTC CCG AG-3' for DHEAS.

Figure 11A:
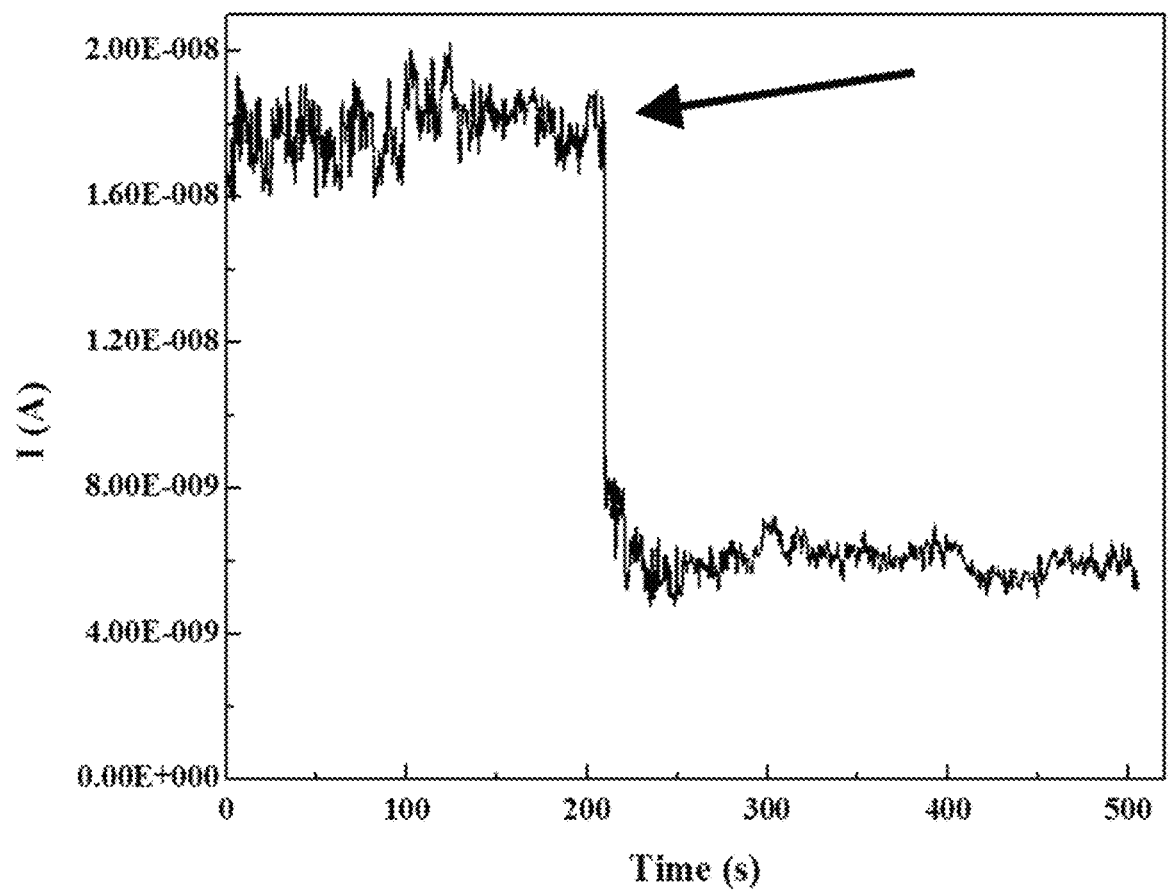
FIG. 11 shows the successive real time detection of three analytes on the same substrate, i.e. using a triple target molecule binding biosensor device capable of detecting cortisol (FIG. 11A), NPY (FIG. 11B) and DHEAS (FIG. 11C). The black arrows indicate when the target molecule/ analyte solution is drop cast.
Figure 11B:
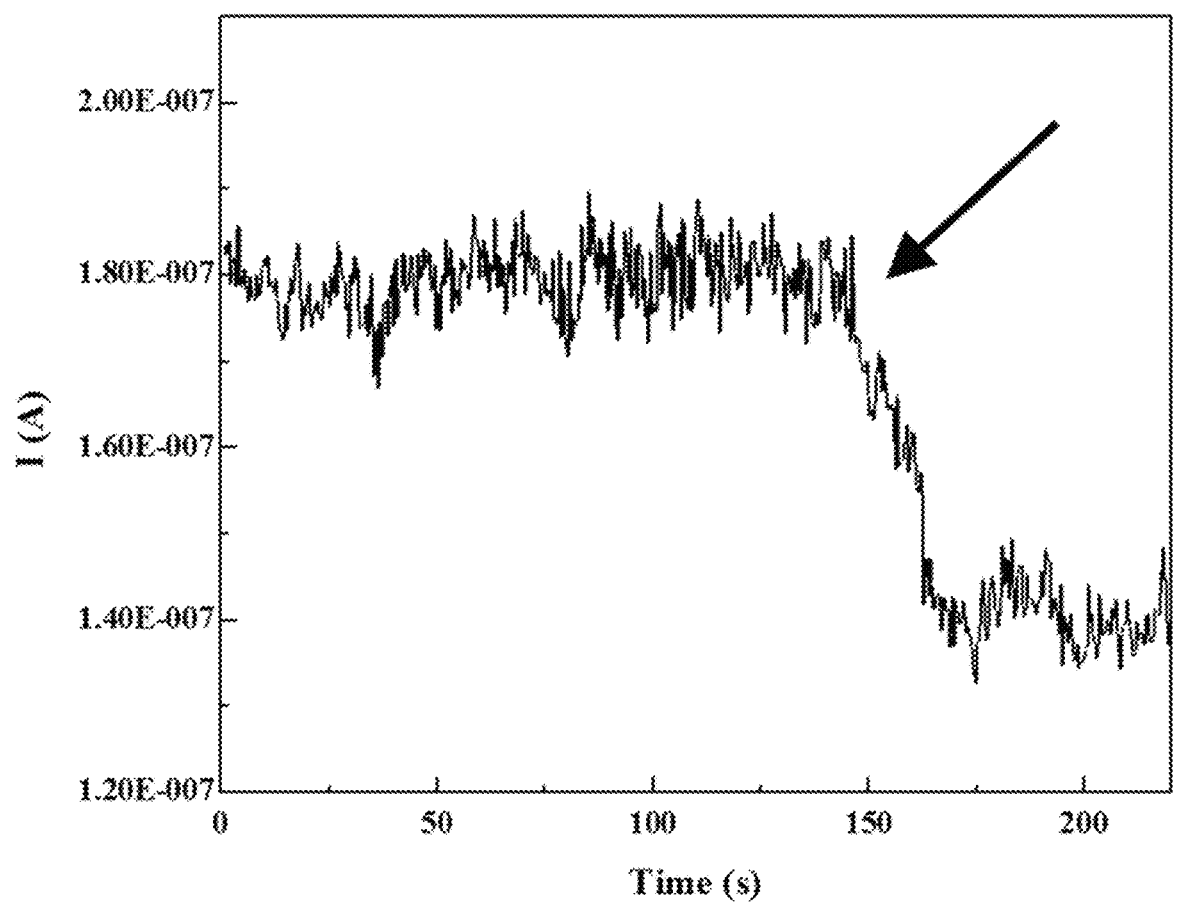
Figure 11C:
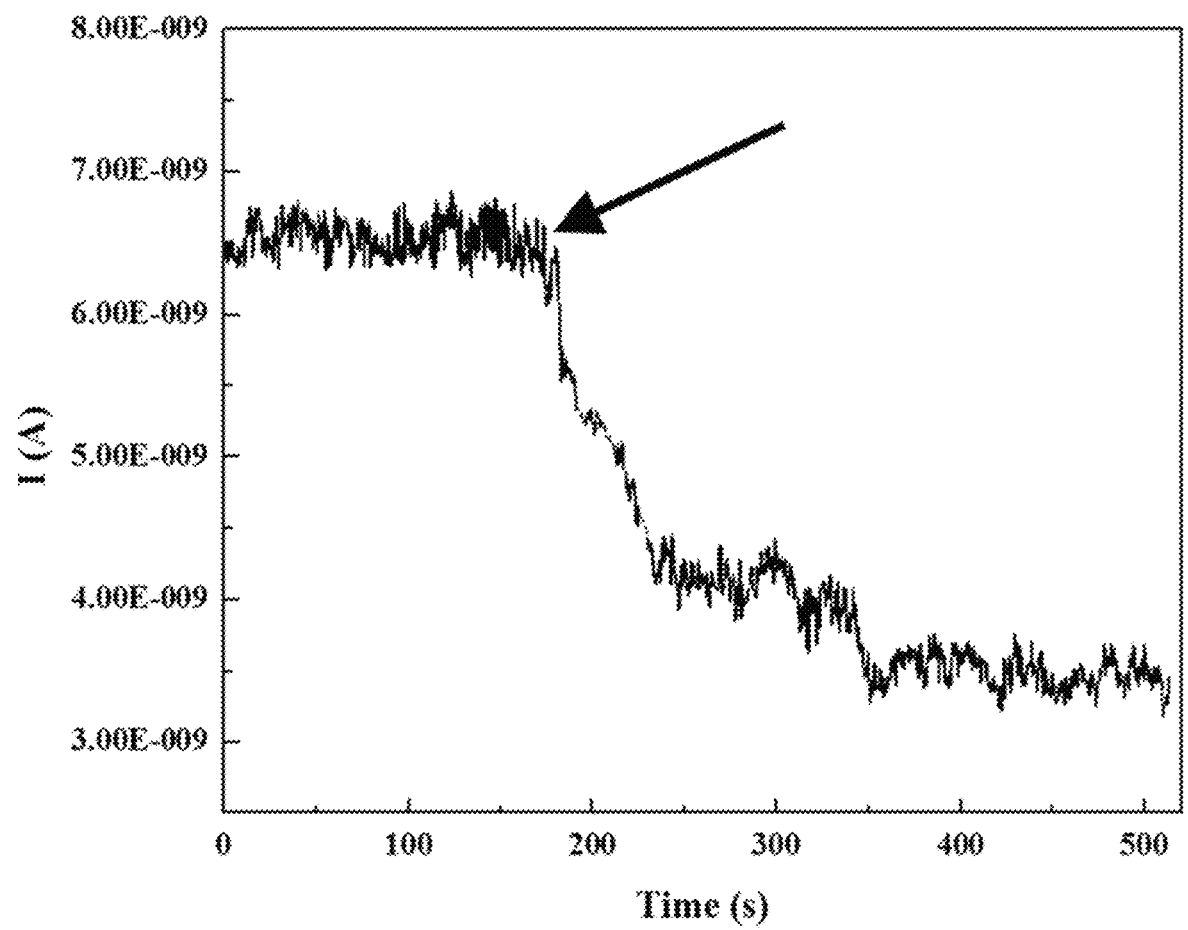

As shown in FIG. 11, successive real time detection of the three target molecules on the same substrate was demonstrated, i.e. using a triple target molecule binding biosensor device. The target molecule was detected as measured by a drop in the conductivity of the device upon binding of the target molecule to the sensor molecule (aptamer). The same device was shown to be capable of selectively detecting cortisol (FIG. 11A), NPY (FIG. 11B) and DHEAS (FIG. 11B). The black arrows indicate when the analyte solution is drop cast onto the device.

Additionally, FIG. 12 shows that upon selective binding of a specific analyte (target molecule) to its specific corresponding aptamer (sensor molecule) tethered to the SWCNT, a reduction can be observed in the current response of the biosensor unit corresponding to the specific analyte, without any crosstalk between the different biosensor units of the device which are selective for the detection of the other analytes, nor were any false-positive signals observed. Each distinct biosensor unit on the chip can be reversed to its initial state by removing the analyte bound to the aptamer via the addition of 8M of urea solution (cleaning step in FIG. 12).

For example, the data shown in FIG. 12 relate to a single biosensor device comprising three biosensor units, each capable of detecting cortisol, neuropeptide-Y (NPY) and DHEAS.

Figure 12A:
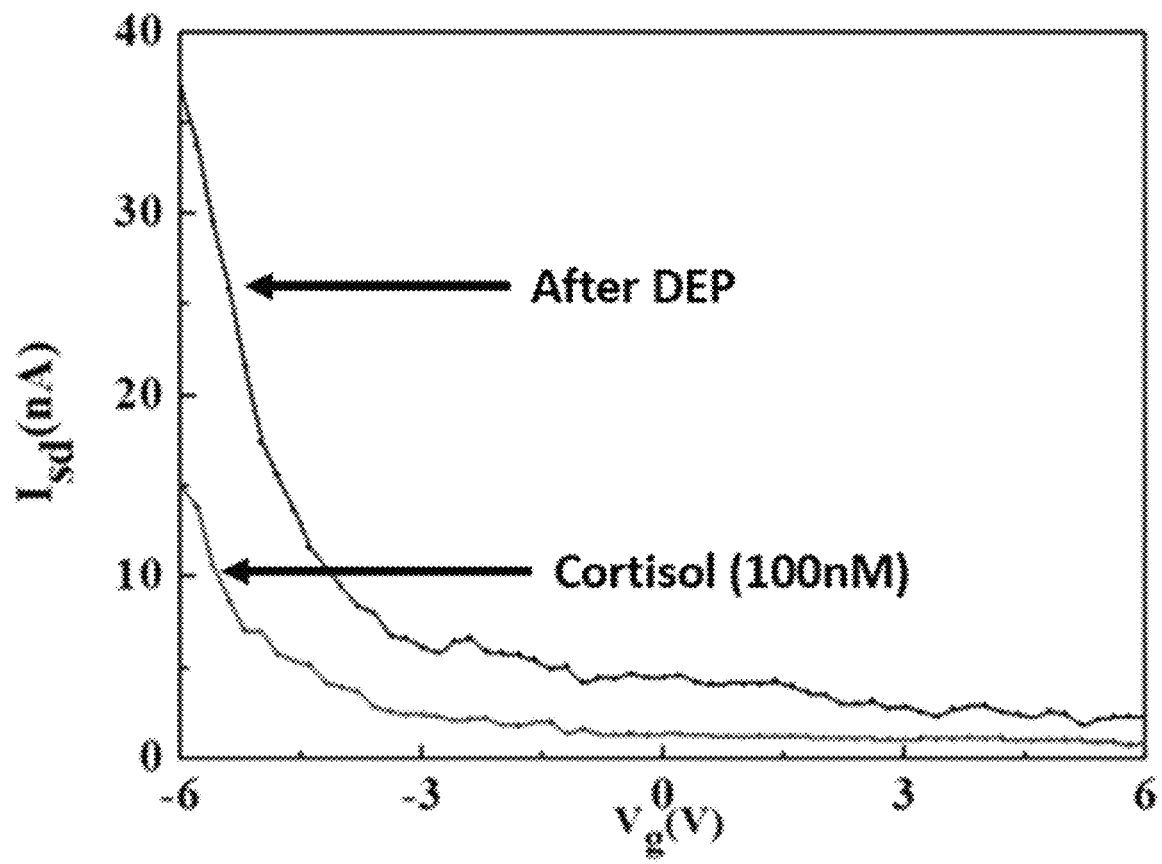
FIG. 12 shows the capability of detecting three analytes on the same substrate, i.e. using a triple target molecule-binding biosensor device capable of detecting cortisol, NPY and DHEAS.

FIGS. 12A, B and C show that the application to the device of cortisol only leads to a change in the current response of only the cortisol biosensor unit, and not the NPY or the DHEAS biosensor units, demonstrating specific and selective detection of a single sensor molecule (cortisol) using a biosensor device having multisensing capability. FIG. 12A shows that the cortisol biosensor unit can be re-set/reversed to its initial state by removing the cortisol bound to the aptamer via the addition of 8M of urea solution.

Figure 12B:
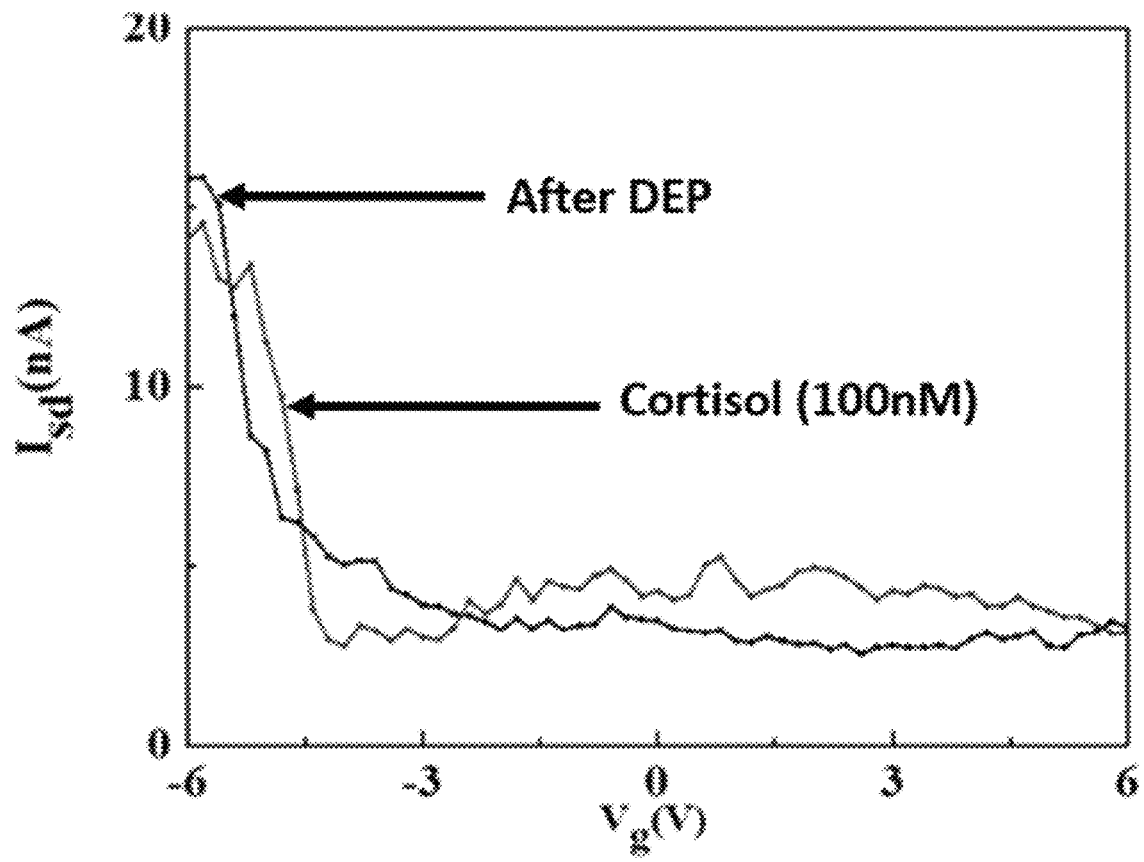
Figure 12C:
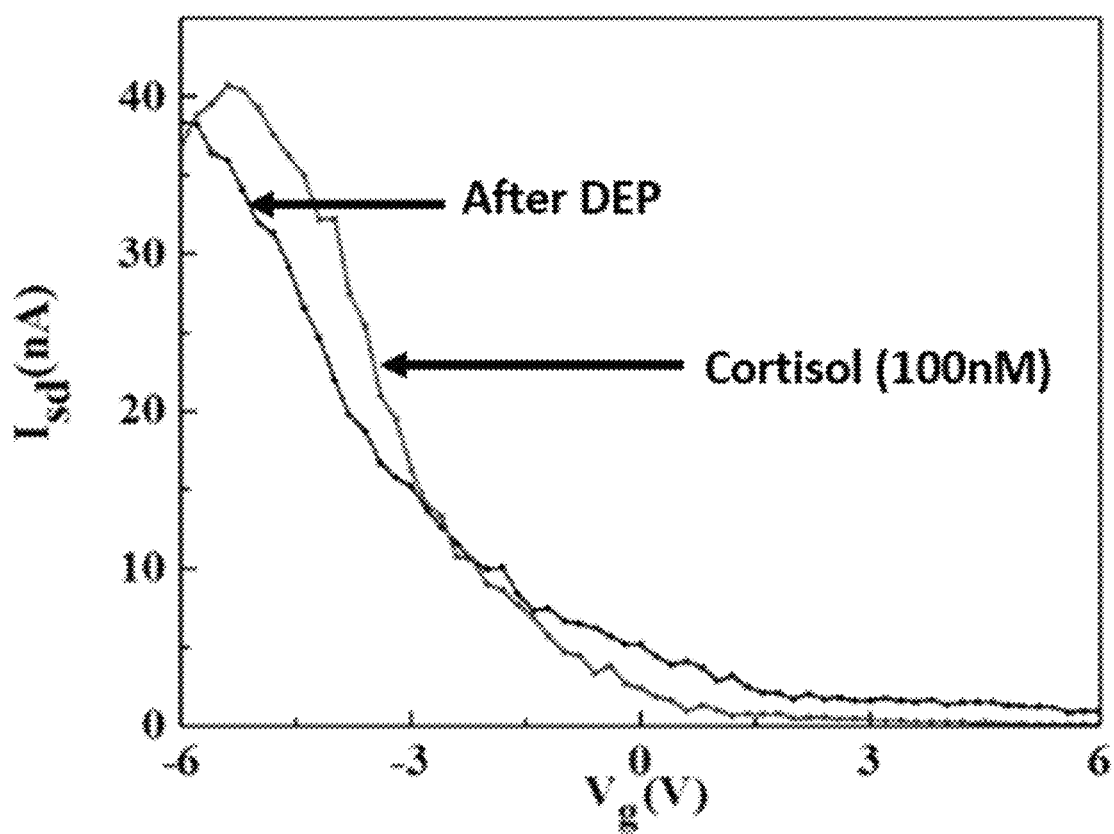
Figure 12D:
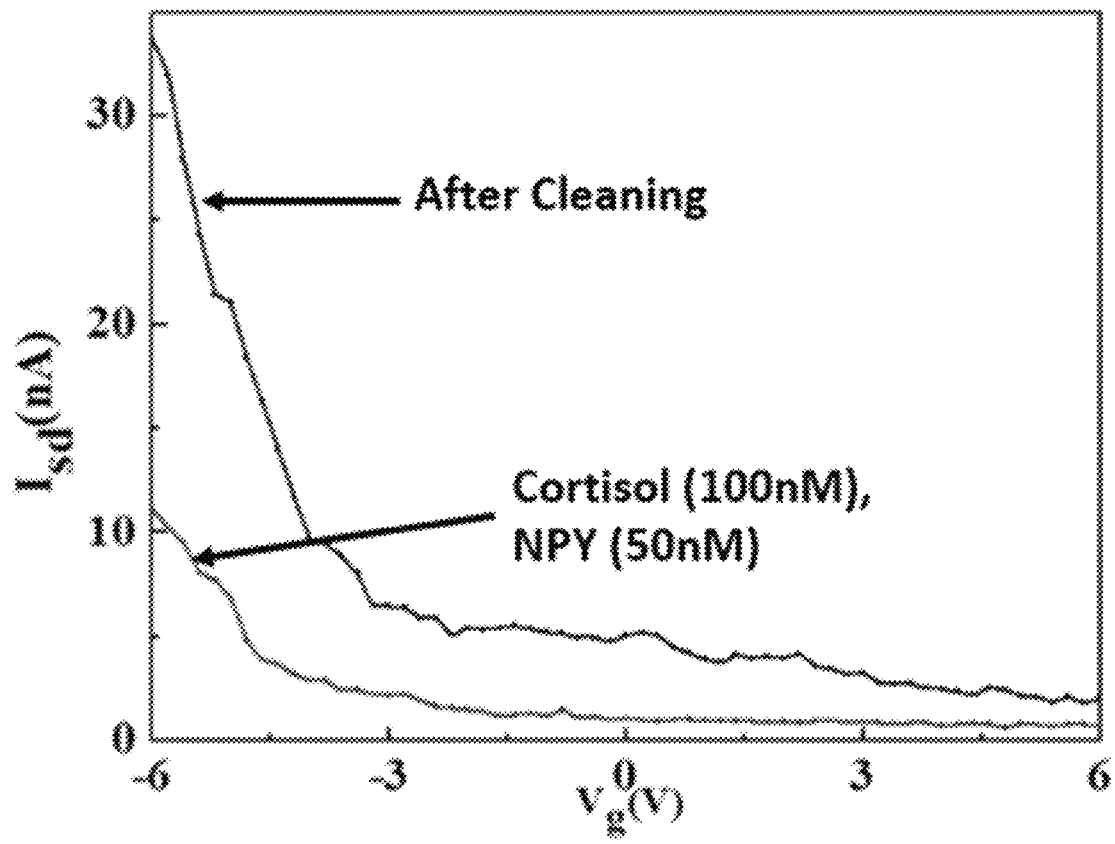
Figure 12E:
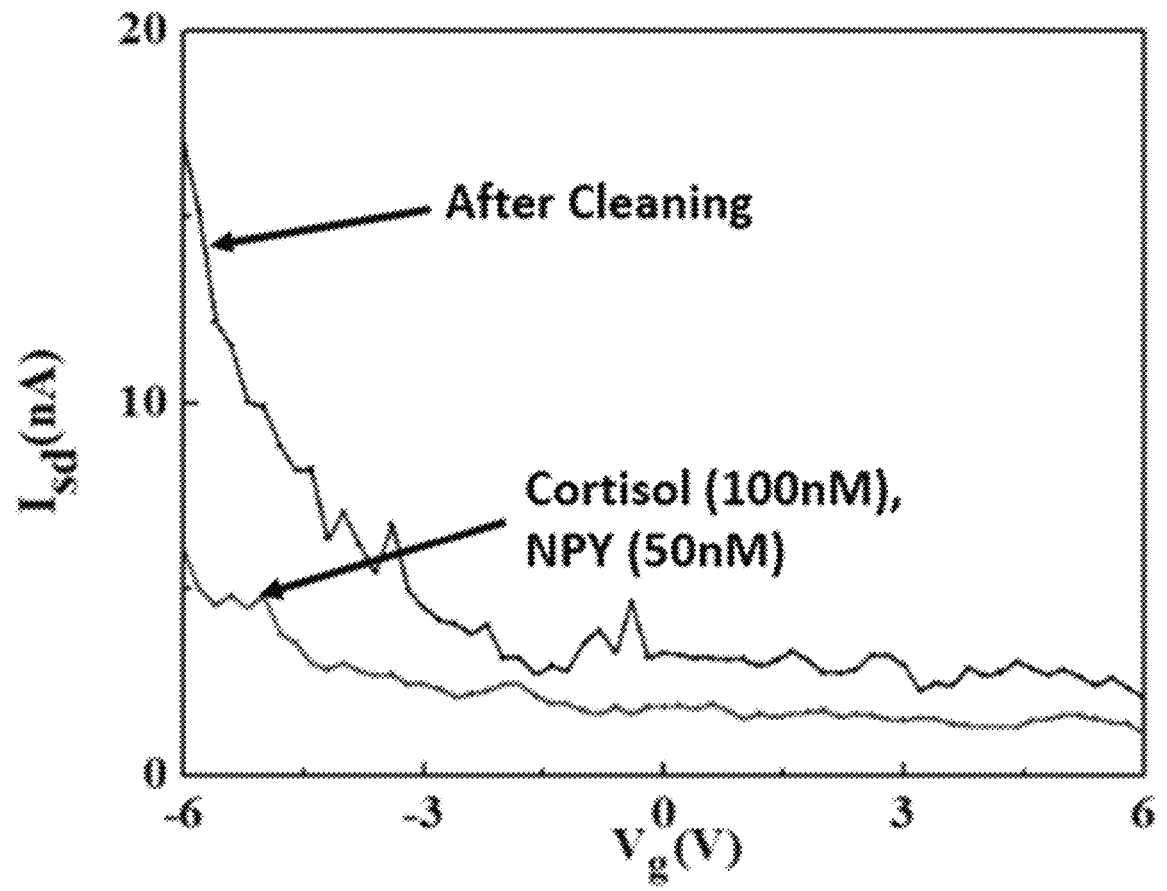
Figure 12F:
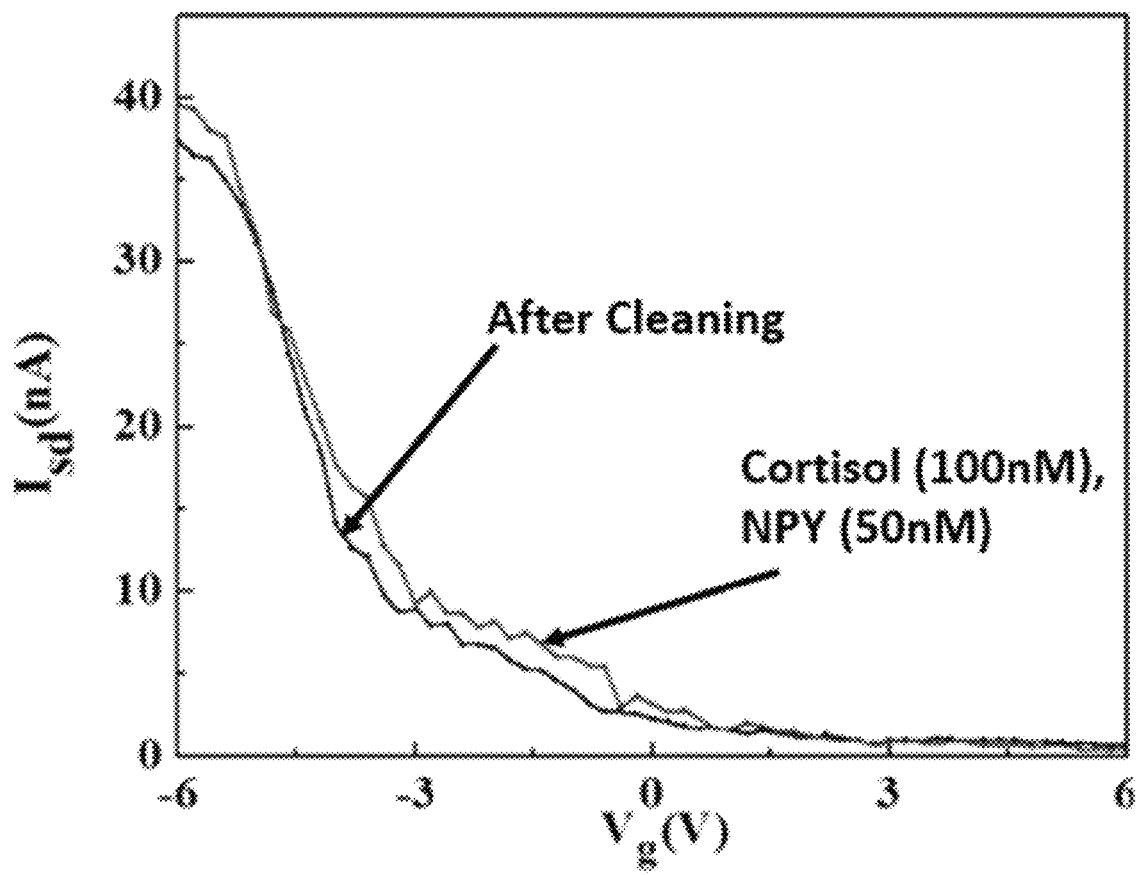

FIGS. 12D, E and F show that the application to the device of cortisol and NPY only leads to a change in the current response of only the cortisol and NPY biosensor units, and not the DHEAS biosensor unit, demonstrating specific and selective detection of two sensor molecules (cortisol and NPY) using a biosensor device having multi-sensing capability. FIGS. 12D and 12E show that the cortisol and NPY biosensor units respectively can be re-set/reversed to their initial states by removing the cortisol and NPY bound to the aptamers via the addition of 8M of urea solution.

Figure 12G:
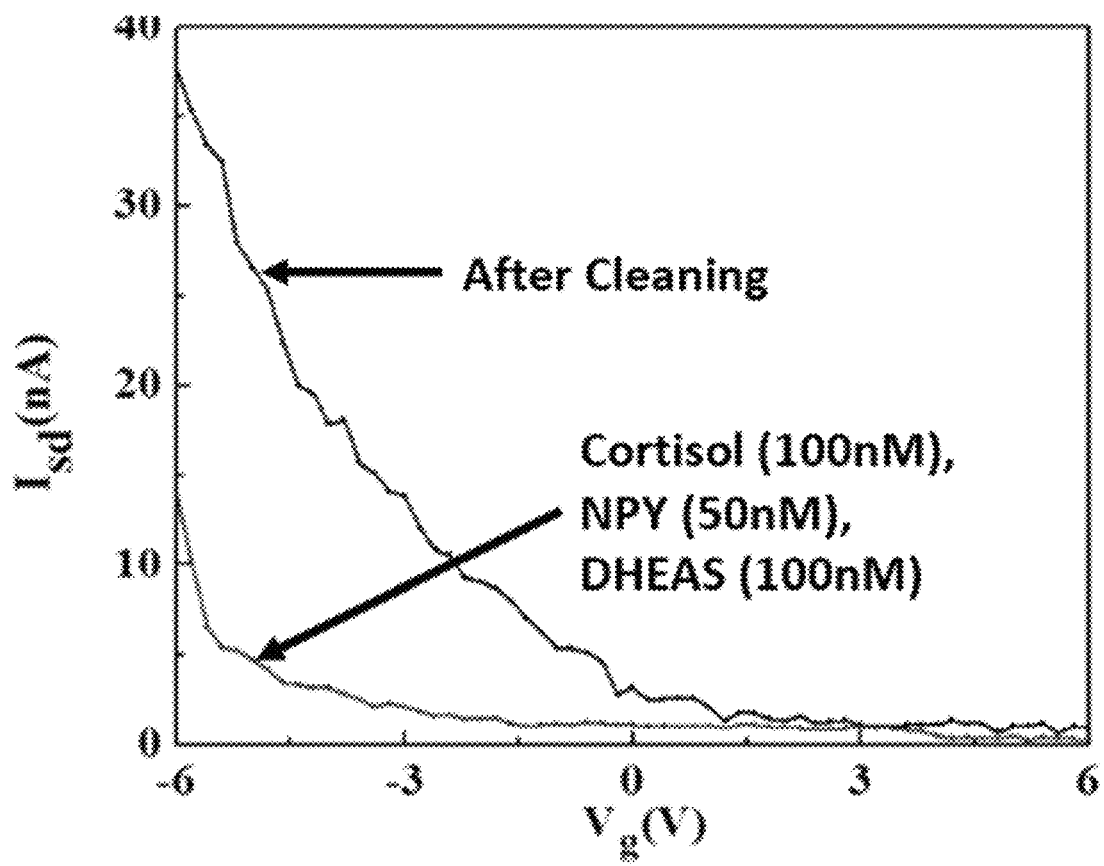
Figure 12H:
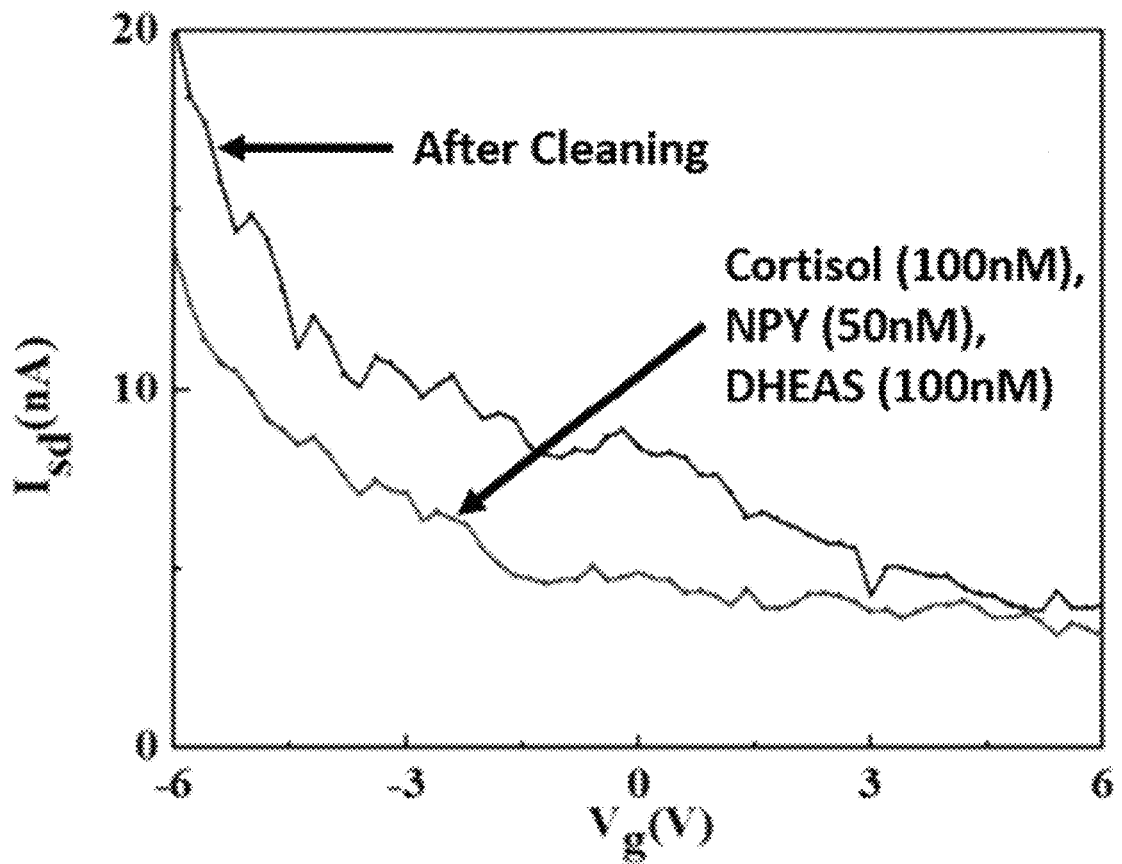
Figure 12I:
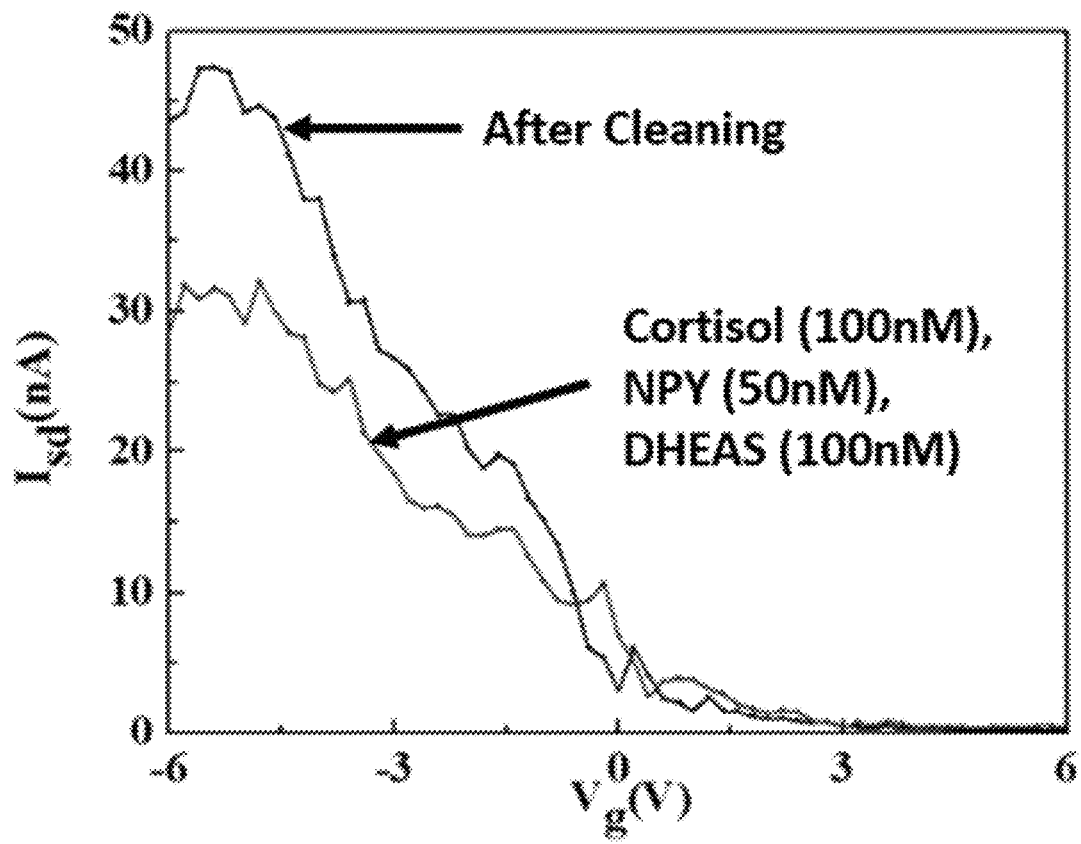

FIGS. 12G, H and I show that the application to the device of cortisol, NPY and DHEAS leads to a change in the current response of all three biosensor units, demonstrating the specific and selective detection of all three sensor molecules using a biosensor device having multisensing capability. FIGS. 12G, H and I show that each of the cortisol, NPY and DHEAS biosensor units can be re-set/reversed to their initial states by removing target molecules bound to the aptamers via the addition of 8M of urea solution.

Example 8: Materials and Methods

The materials and methods presented in this Example relate to the disclosures of Examples 9 to 19.

Figure 13:
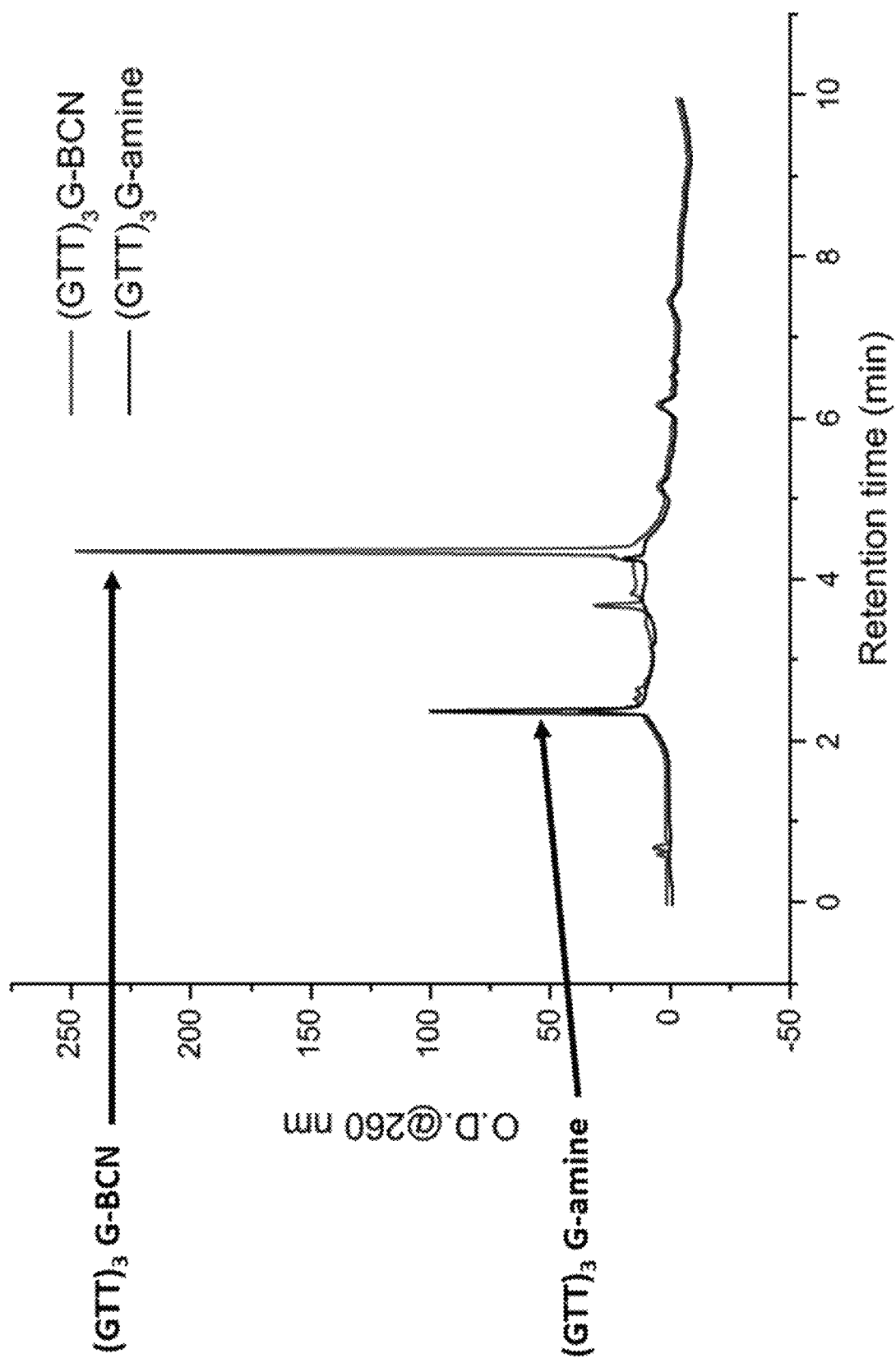
FIG. 13 shows the HPLC analysis of the chemical modification of (GTT)$_3$G-amine to (GTT)$_3$G-BCN 0.2 mg (7,6) enriched SWCNTs were dispersed into the as prepared (GTT)$_3$G-BCN solution (300 μL) by sonication (Sonics, VC130) for 30 mins. The mixture was centrifuged at 13K rpm for 30 mins to remove unwrapped CNTs.

Single-chirality enriched semiconducting SWCNTs were wrapped with single stranded DNA (ss-DNA) containing a bicyclononyne (BCN) functionality (see below and FIG. 13). This allowed tethering of azide-terminated aptamers to the DNA-wrapped CNTs, via a simple copper-free cycloaddition, directly in solution and without altering the electronic properties of the nanotubes by covalent attachment (Park et al. Nano Lett. 2006, 6, 916-919). Notably, the reaction of different azide-terminated aptamers to separate solutions of BCN-DNA-wrapped CNTs permits the preparation of distinct aptamer-functionalized SWCNTs solutions. This strategy was employed to produce three different solutions of SWCNTs each functionalized with a distinct aptamer selective to a specific biomarker namely, cortisol, NPY, and DHEAS: the schematic in FIG. 2 outlines a similar approach (see also below).

Reagents for wrapping of SWCNT with ss-DNA as outlined above are as follows. 2-[Methoxy(polyethyleneoxy)6-9propyl]trimethoxysilane (PEG-silane) was purchased from Fluorochem. Ltd. Steroid free serum was purchased from MP Biomedicals, Inc. Dulbecco's phosphate buffered saline (DPBS) was purchased from Thermo Scientific. Enriched SWCNTs were purchased from Sigma Aldrich. All other analytical grade chemicals were purchased from Sigma Aldrich.

All DNAs were obtained from IDT. Cortisol binding aptamer, Neuropeptide Y (NPY) binding aptamer and dehydroepiandrosterone sulfate (DHEAS) binding aptamer were already functionalized with an azide group on the 5' terminal position (via N-hydroxysuccinimide ester reaction). Sequences of the three aptamers used were: Cortisol aptamer: 5'-azide-GGA ATG GAT CCA CAT CCA TGG ATG GGC AAT GCG GGG TGG AGA ATG GTT GCC GCA CTT CGG CTT CAC TGC AGA CTT GAC GAA GCT T-3' NPY aptamer: 5'-azide-AGC AGC ACA GAG GTC AGA TGC AAA CCA CAG CCT GAG TGG TTA GCG TAT GTC ATT TAC GGA CCT ATG CGT GCT ACC GTG AA-3' DHEAS aptamer: 5'-azide-CTG CTC TCG GGA CGT GGA TTT TCC GCA TAC GAA GTT GTC CCG AG-3'

Single stranded DNA used to wrap enriched SWCNTs was modified with an amine group on the 3' terminal position. The sequence used was 5'-GTT GTT GTT G-amine-3' ((GTT)$_3$G-amine). This sequence was employed for the wrapping of the nanotubes as it was shown to be able to wrap different chiralities of SWCNTs and worked efficiently for the dispersion of the enriched chirality SWCNTs employed in this study.

The sequence of the DNA complementary to cortisol aptamer used were 5'-AAG CTT CGT CAA GTC TGC AGT GAA GCC GAA GTG CGG CAA CCA TTC TCC ACC CCG CAT TGC CCA TCC ATG GAT GTG GAT CCA TTC C-3'.

Figure 19:
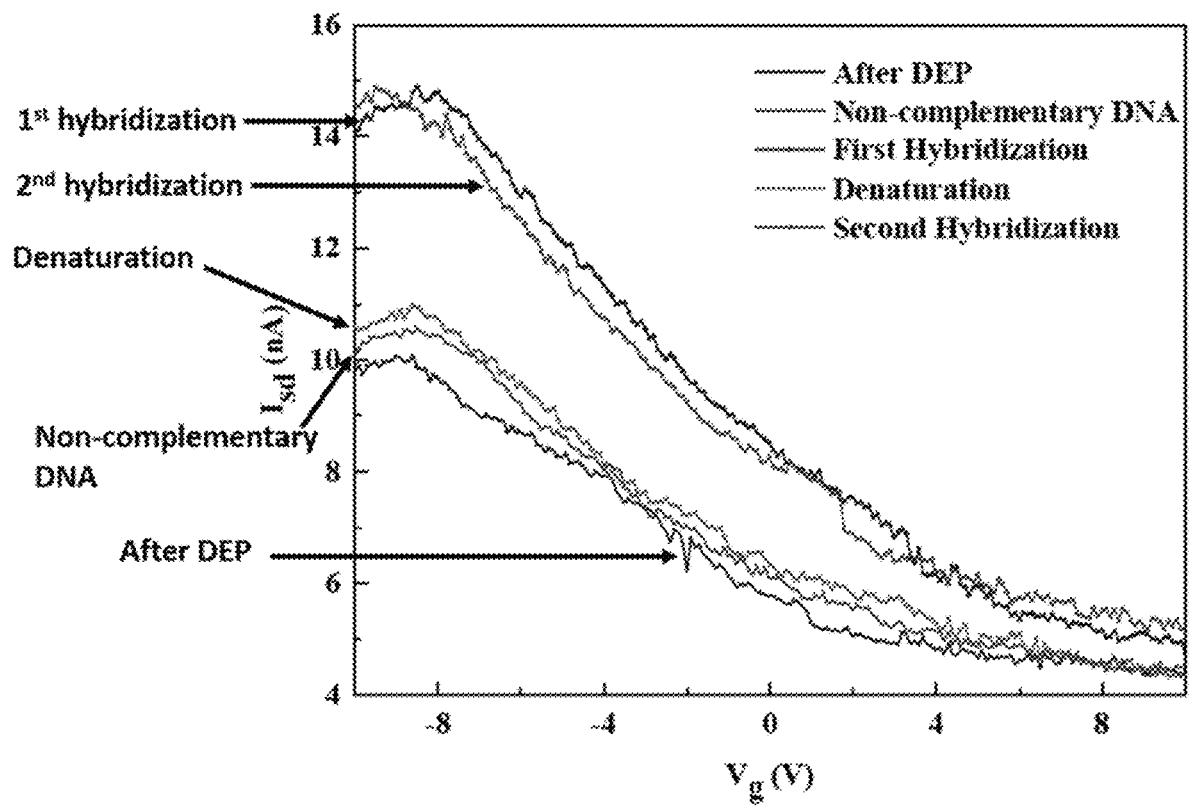
FIG. 19 shows the $I_{sd}$ vs $V_g$ characterization of the device functionalized with cortisol aptamer before (black) and after exposure to non-complementary DNA (red), after exposure to complementary DNA (blue), after DNA denaturation (green) and a second hybridization with the complementary DNA (purple); $V_{sd}$=100 mV.

For the non-complementary control experiment, the sequence of the non-complementary DNA shown in FIG. 19 is 5'-GAT TCA GCA ATT AAG CTC TAA GCG ATC CGC AAC ACT GAC CTC TTA TCA AAA GGA GCA ATT AAA GGT ACT CTC TAA TCC TGA CGG G-3'.

For analyte detection, the Tris-HCl buffer was composed of 50 mM Tris-HCl, 100 mM NaCl, 5 mM MgCl$_2$ and was adjusted to pH=7.4 at 25° C. 0.1 M phosphate buffer was prepared with 0.1 M Na2HPO4 solution and adjusted to pH=9 with 0.1 M NaH$_2$PO$_4$ solution at 25° C.

Example 9: Substrate Fabrication

The electron beam (e-beam) lift-off resist (MCC NANO Copolymer EL6) was bought from Microlithography Chemicals Corp. The top layer ebeam resist (ARP 6200.13: Anisol 1:2), was bought from Allresist GmBH. The photo lift-off resist (LOR3A) and the protective resist (MCC NANO Copolymer EL10) was bought from Microlithography Chemicals Corp and the photoresist (S1813) was bought from Microresist GmBH.

The nanosized features were fabricated using electron beam lithography (EBL). A 4 inch p-doped (10-20 mΩ cm) silicon wafer (100), with a 400 nm thick grown silicon dioxide was used as a substrate. This was spin-coated with a 100 nm thick lift-off resist at 6000 rpm for 60 s and baked at 160° C. Subsequently, a second ebeam resist was spin-coated at 600 rpm for 60 s and baked at 160° C. for 5 min. An e-beam writer (EBL-JEOL JBX 9300 FS) system set to use an accelerating voltage of 100 kV, a current of 2 nA and an electron dose of 160 μC/cm2 was used to expose the substrate according to a predesigned pattern. The pattern was developed for 20 s in o-xylene and rinsed in 2-propanol. This was followed by a second development in a mixture of 7 parts deionized water and 93 parts 2-propanol, rinsing in 2-propanol and dried in N2. Residues were removed in 02 plasma for 10 s (50 w, 250 mTorr, 15 sccm) using a Dry etch RIE-Plasma-Therm-Oxygen. The entire sample was coated with 5 nm of chromium using an electron beam evaporator (Lesker PVD 225). The sample was then covered with 40 nm of gold. A lift off in acetone was performed overnight, followed by rinsing in first acetone, then 2-propanol, finally deionized water and dried in N$_2$. 60 s O$_2$-plasma was used to clean the nano-features. The larger features on the wafer was fabricated using a laser writer (Heidelberg Instruments DWL 2000) equipped with a 405 nm diode laser. First a photo lift-off resist was spin-coated at 3000 rpm for 45 s and baked at 190° C. for 5 min. A photo resist was then spin-coated at 3000 rpm and baked at 100° C. for 2 min. The sample was then exposed according to a predesigned pattern. The wafer was then developed in MF319 for 45 s, followed by rinsing in a bath of deionized water and drying in N$_2$. Finally, 60 s of O$_2$-plasma was used to clean the sample. A protective resist was spin-coated at 1000 rpm for 60 s and baked at 160° C. for 5 min prior to dizing the sample in 10×10 mm chips using a dicing saw (Loadpoint Microace 3+). These chips in total were equipped with gold electrodes. Each chip contained 2 sets containing 10 electrode pairs each with a gap of 300 nm and 2 sets containing 10 electrode pairs with a gap of 400 nm. The electrode pairs in each set was separated with 50 μm. A distance of 800 μm between a set of gaps to any contact pad assured that any short circuit during deposition was evaded. After the fabrication of electrodes, a PEG-silane monolayer was formed on the surface of the as prepared substrate. The substrate was incubated overnight into a solution of 10 μL PEG-silane containing 20 mL of anhydrous toluene and 50 μL acetic acid (99%).

Example 10: Preparation of CNT-Aptamer Hybrids 1.0 mg (1R,8S,9s)-Bicyclo[6.1.0]non-4-yn-9-ylmethyl N-succinimidyl carbonate (BCN-NHS) was dissolved in 42 μL dimethyl sulfoxide (DMSO), then diluted with 225 μL phosphate buffer (0.1 M, pH 9). 12 μL of 25 mg/mL of (GTT)$_3$G-amine was added to the solution, and additional water (MilliQ) was added to get the total volume of 300 μL. After overnight incubation at room temperature, ethanol precipitation was used to remove free BCN-NHS. 30 μL NaCl (3 M) and 825 μL ethanol (95%) were added to the mixture, kept in the freezer for 2 h and then centrifuged at 13 Krpm (Eppendorf 5415C) for 30 mins. The precipitation was washed with 70% cold ethanol (−20° C.). After being dried, the modified DNA ((GTT)$_3$G-BCN) was re-dissolved in 0.1 M NaCl. Subsequently, 3 KDa Amicon filter (Millipore) was used to further remove free BCN-NHS by centrifugation at 13K rpm for 10 mins three times. The final solution was diluted with 0.1 M NaCl and the volume was kept to 300 μL.

To demonstrate the successful modification of (GTT)$_3$G-amine with BCN group, (GTT)$_3$G-BCN and (GTT)$_3$G-amine samples were analysed with HPLC (High Performance Liquid Chromatography, Agilent LC 1100,)(Bridge Column Reversed-Phase 2.5 μm, 4.6 mm×50 mm). As shown in FIG. 13, HPLC analysis of the BCN-ssDNA compared to the amine-ssDNA shows a shift in the retention time of the more hydrophobic BCN-ssDNA, suggesting the successful BCN functionalization of the DNA following the BCN-NHS chemistry on the amine-terminated DNA.

For the functionalization of CNT with aptamers, typically, 6 μL of as prepared CNT solution was mixed with 2 μL aptamer solution (100 μM) and 12 μL DPBS was added to the mixture. Then, the mixture was incubated at 37° C. overnight. After the reaction, the mixture was dialysed against water using Slide-A-Lyzer™ MINI Dialysis Devices with a 20 kDa cut-off (purchased from Thermo Scientific) overnight to remove free aptamers.

Example 11: AFM Images and their Corresponding Height Profiles

Figure 14A:
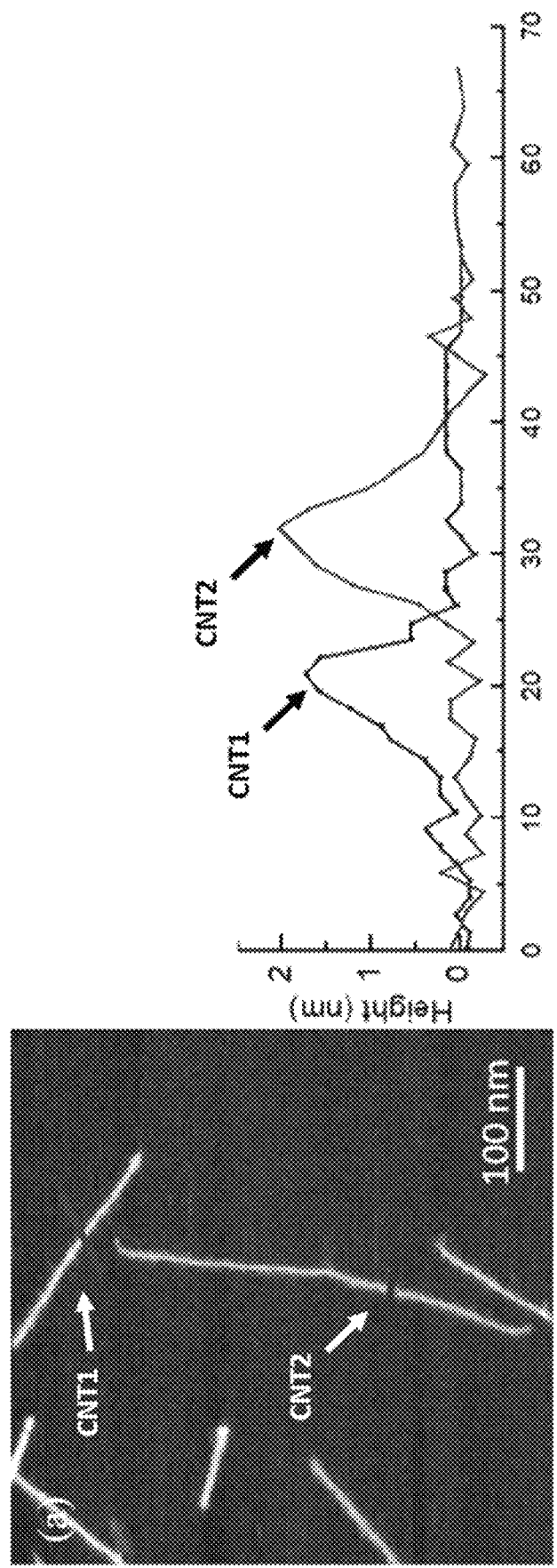
FIG. 14 shows AFM images and their corresponding height profiles of (A) CNT-aptamer hybrids, and (B) CNT-aptamer hybridized with complementary DNA. Free dsDNA not bound to the SWCNTs can also be found in the vicinity of the nanotubes; this can be differentiated from the dsDNA tethered to the SWCNTs because of both its distance from the nanotube and its conformation: the dsDNA linked to the tubes clearly protrudes at a 90° angle with respect to the nanotube (additionally, it is reasonable to expect only minimal non-specific adsorption of dsDNA on the SWCNTs, due to electrostatic repulsion with the DNA wrapping the nanotubes). AFM images and their corresponding height profiles of control experiment (C) with non-complementary DNA, and (D) of CNT-aptamer hybrids immobilized between electrodes: a height up to 15 nm, indicating the presence of up to 7 CNTs in the device.
Figure 14B:
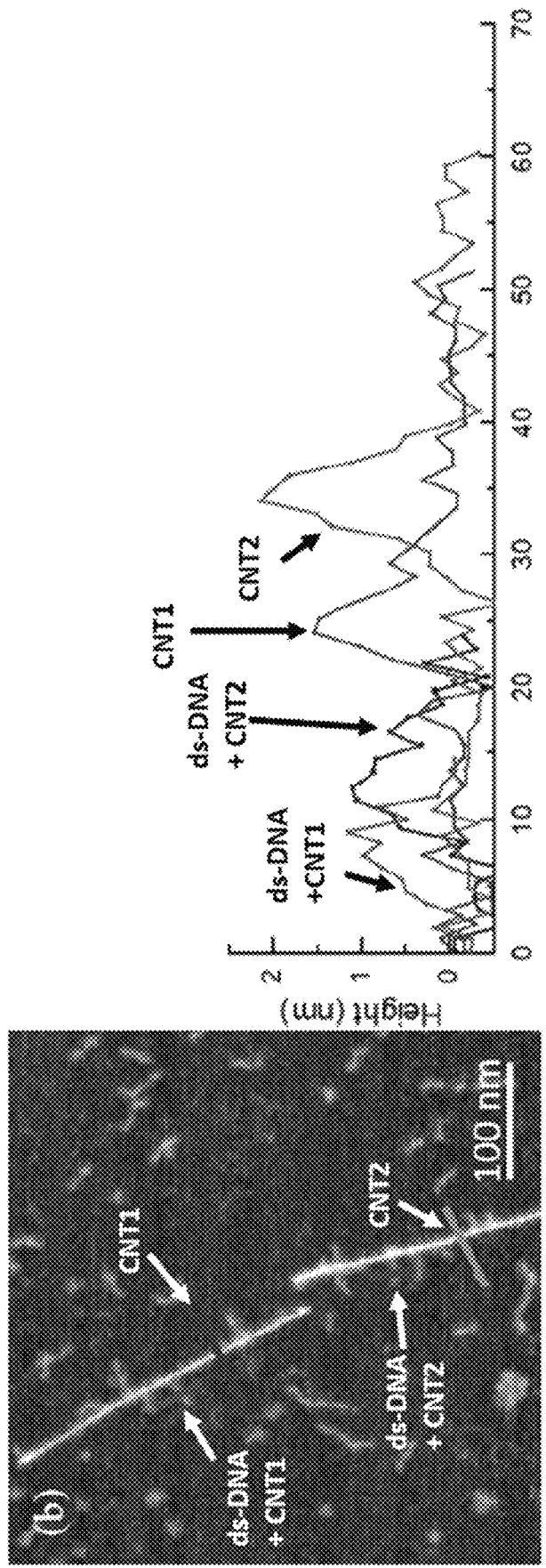
Figure 14C:
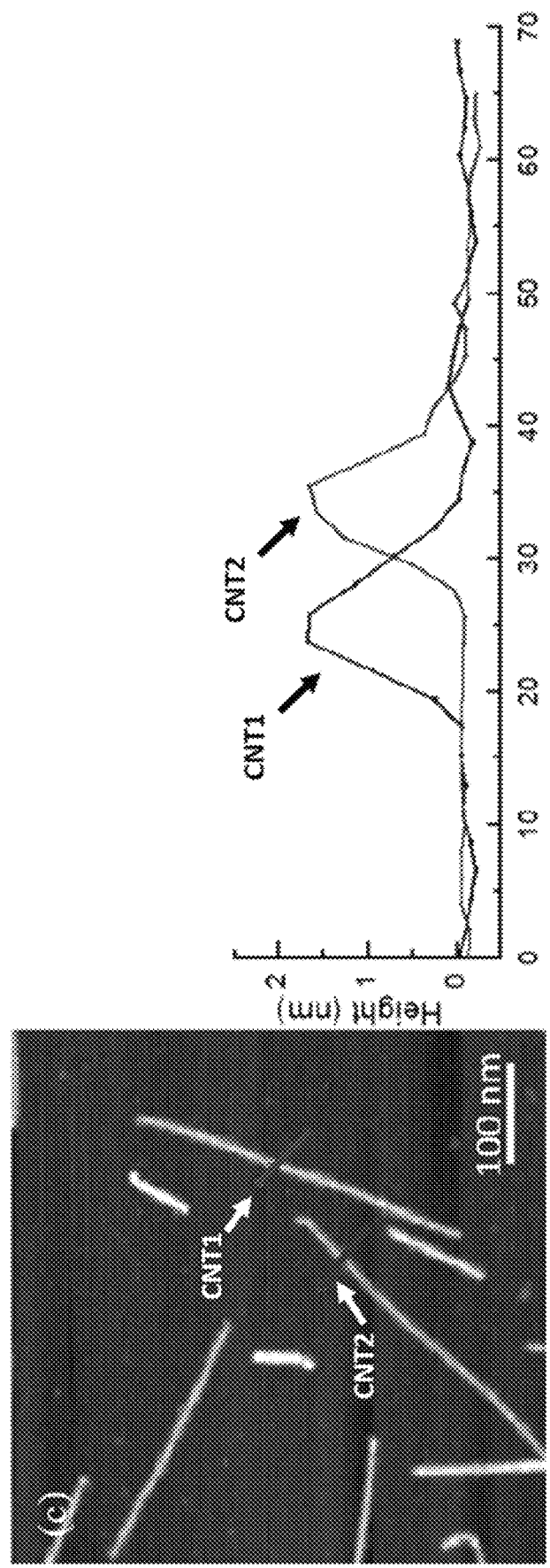

In order to verify the successful functionalization of DNA wrapped SWCNTs with the employed aptamers, the inventors hybridized cortisol aptamer-functionalized nanotubes with complementary ss-DNA directly in solution, then cast these on muscovite mica substrates and imaged the with atomic force microscopy (AFM). FIG. 1 shows representative AFM images of the aptamer-functionalized SWCNTs before and after hybridization with the complementary strands. The double-stranded (ds) DNA portion protruding out of the nanotubes is clearly visible in the samples that were exposed to the aptamer's complementary sequence (free ds-DNA not bound to the SWCNTs can also be found in the vicinity of the nanotubes: see also FIG. 14A-C). This demonstrates that the functionalization strategy was successful: the nucleic acid aptamers are present on the SWCNTs and are accessible to other biomolecules, ss-DNA in this case, an important feature for the subsequent use of these hybrids as selective recognition elements in a device. From the analysis of AFM images of multiple nanotubes in different samples it was determined that each SWCNT exhibited on average 4±2 aptamers per 100 nm, and that these are available for hybridization. Additionally, it is reasonable to assume that the tens of nanometers distance between the aptamers on each nanotube will prevent potential detrimental crowding effects on the biosensing properties of these hybrids once immobilized in a device.

Example 12: Dielectrophoresis

Figure 3:
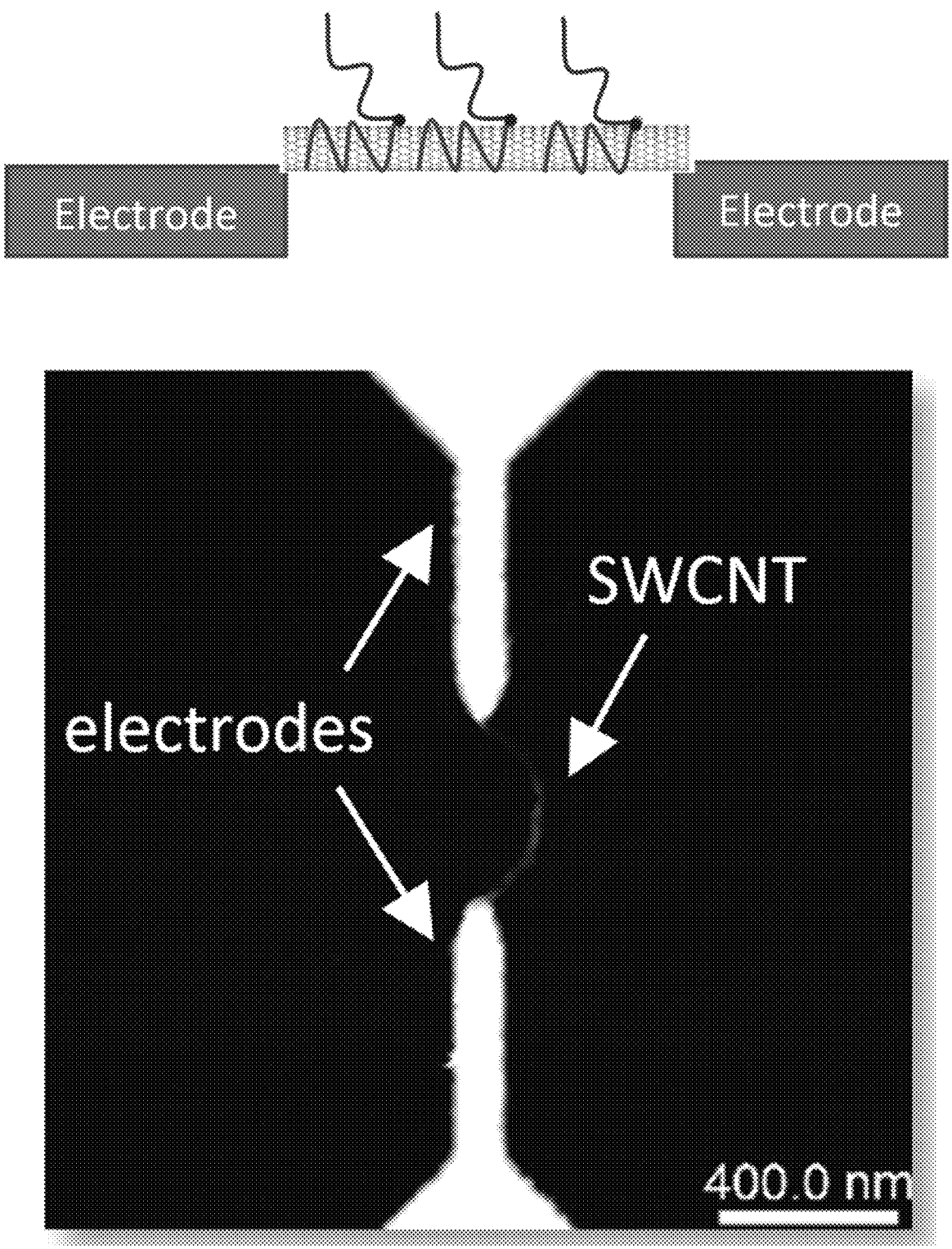
FIG. 3 shows an exemplary schematic (top) and AFM micrograph (bottom) of an immobilised SWCNT across electrode pairs to form an electrical connection.
Figure 4:
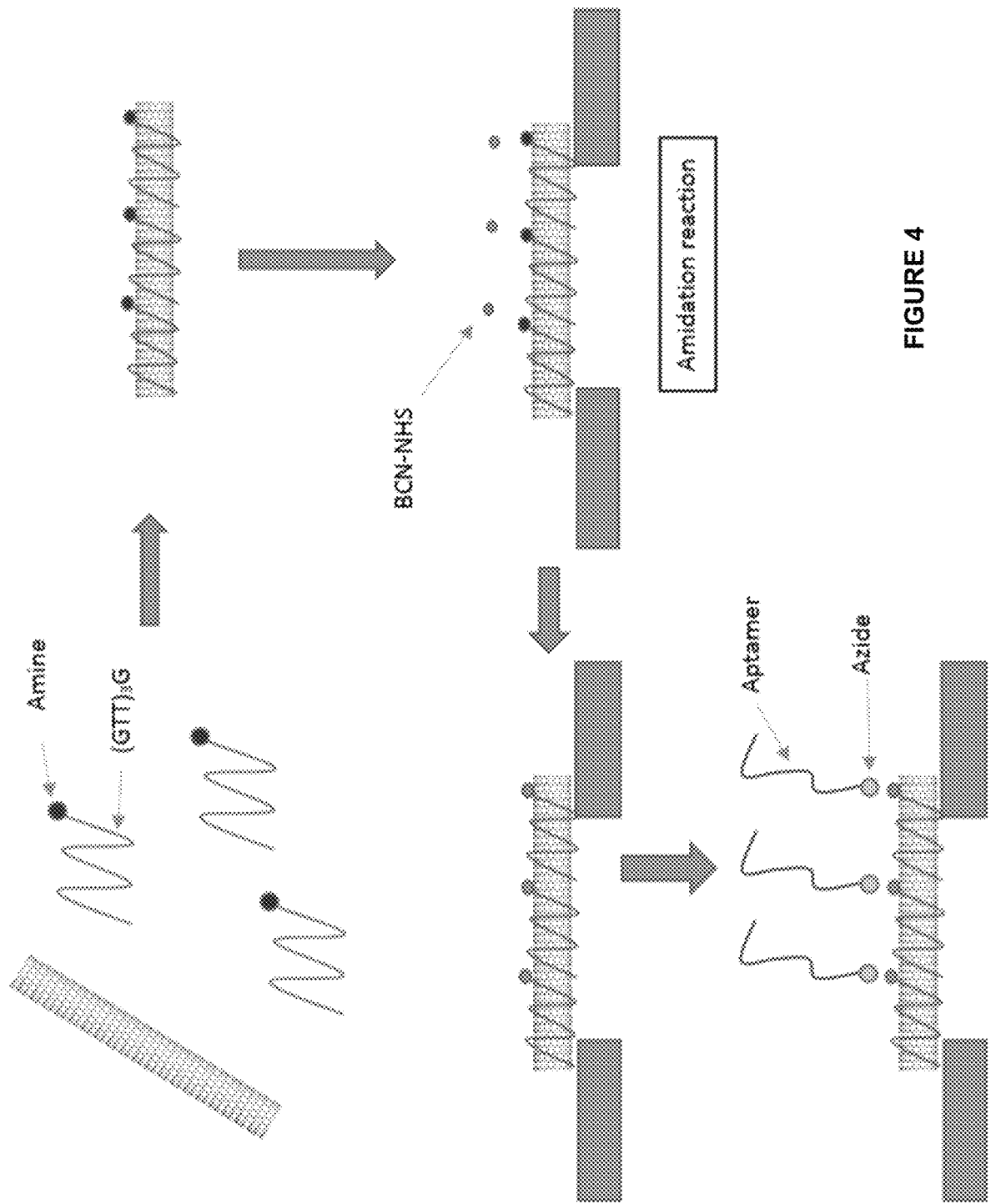
FIG. 4 shows an exemplary schematic of the formation of a single biosensor unit from starting components.
Figure 14D:
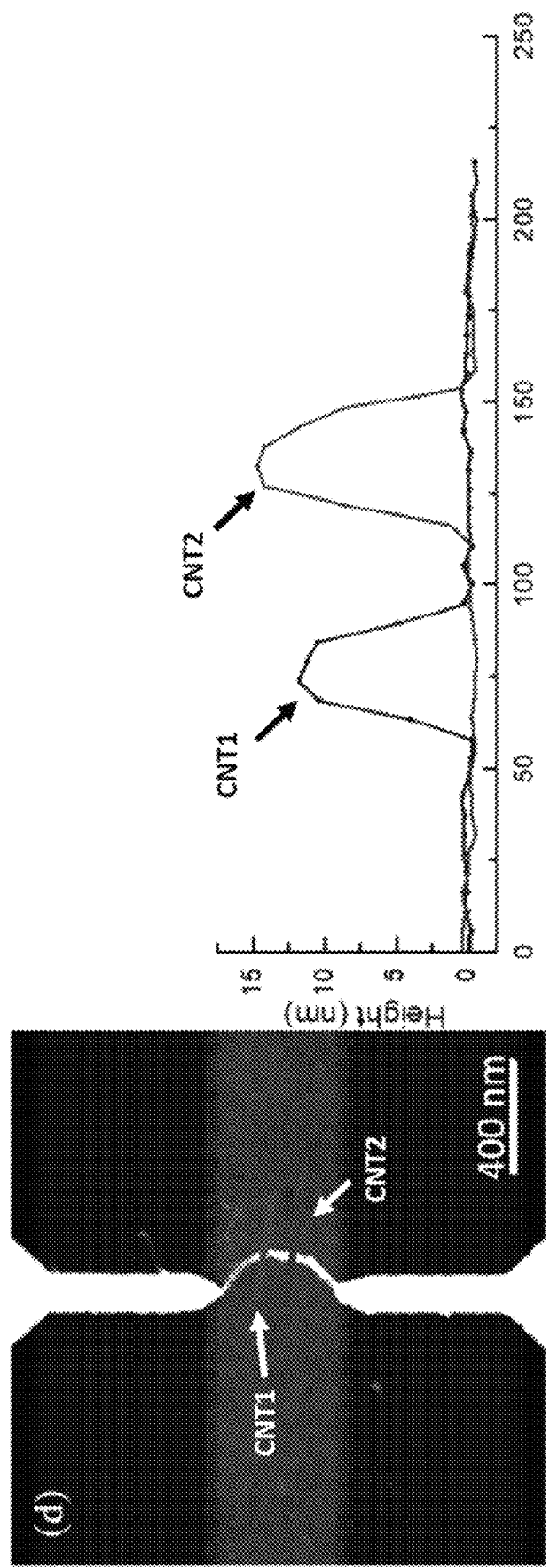
Figure 15:
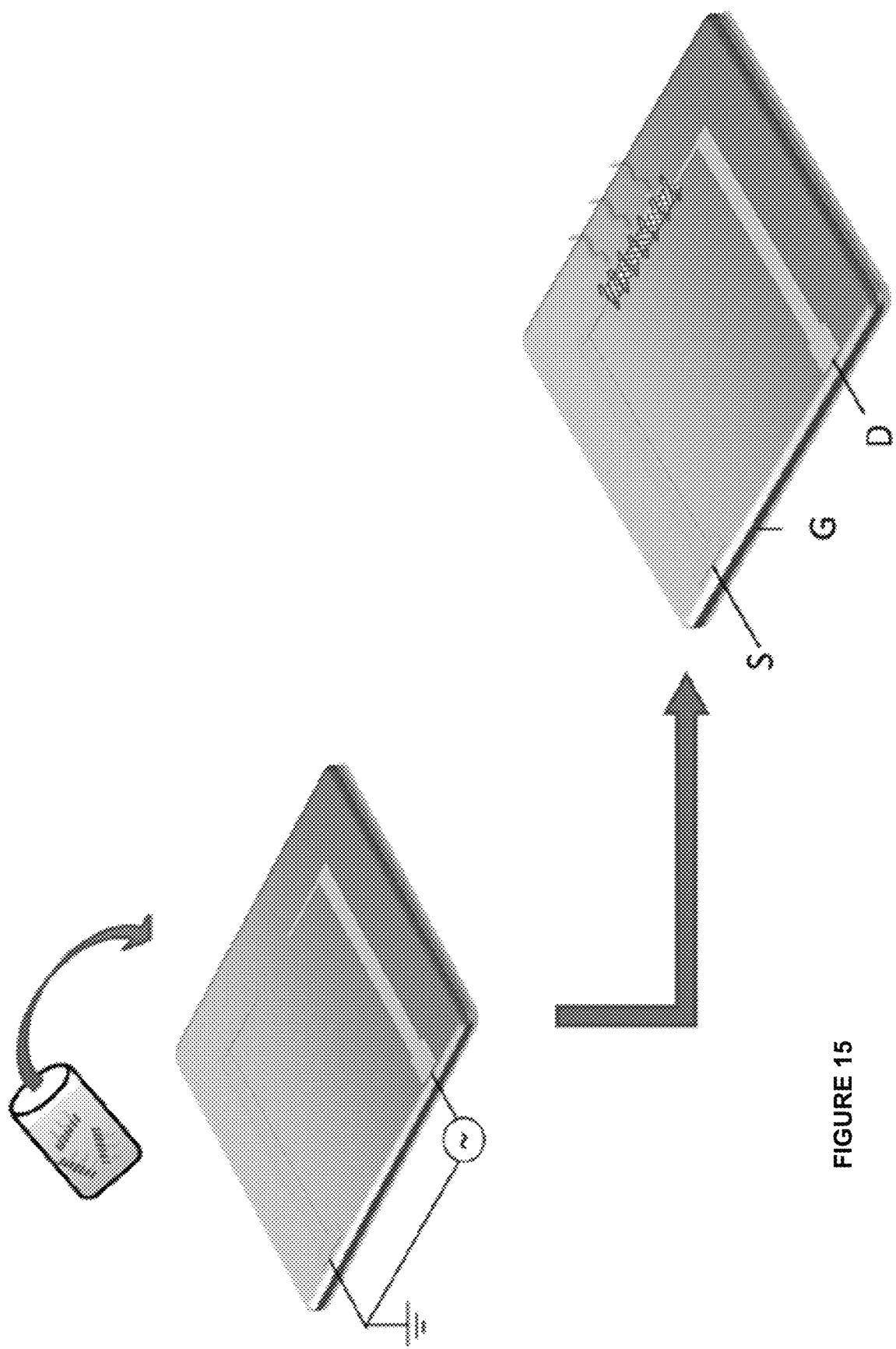
FIG. 15 shows the DEP of SWCNT-aptamer hybrids. S, D, and G respectively indicate the source, drain, and gate (electrodes); Z-scales=10 nm. The corresponding AFM micrograph is shown in FIG. 3.
Figure 16:
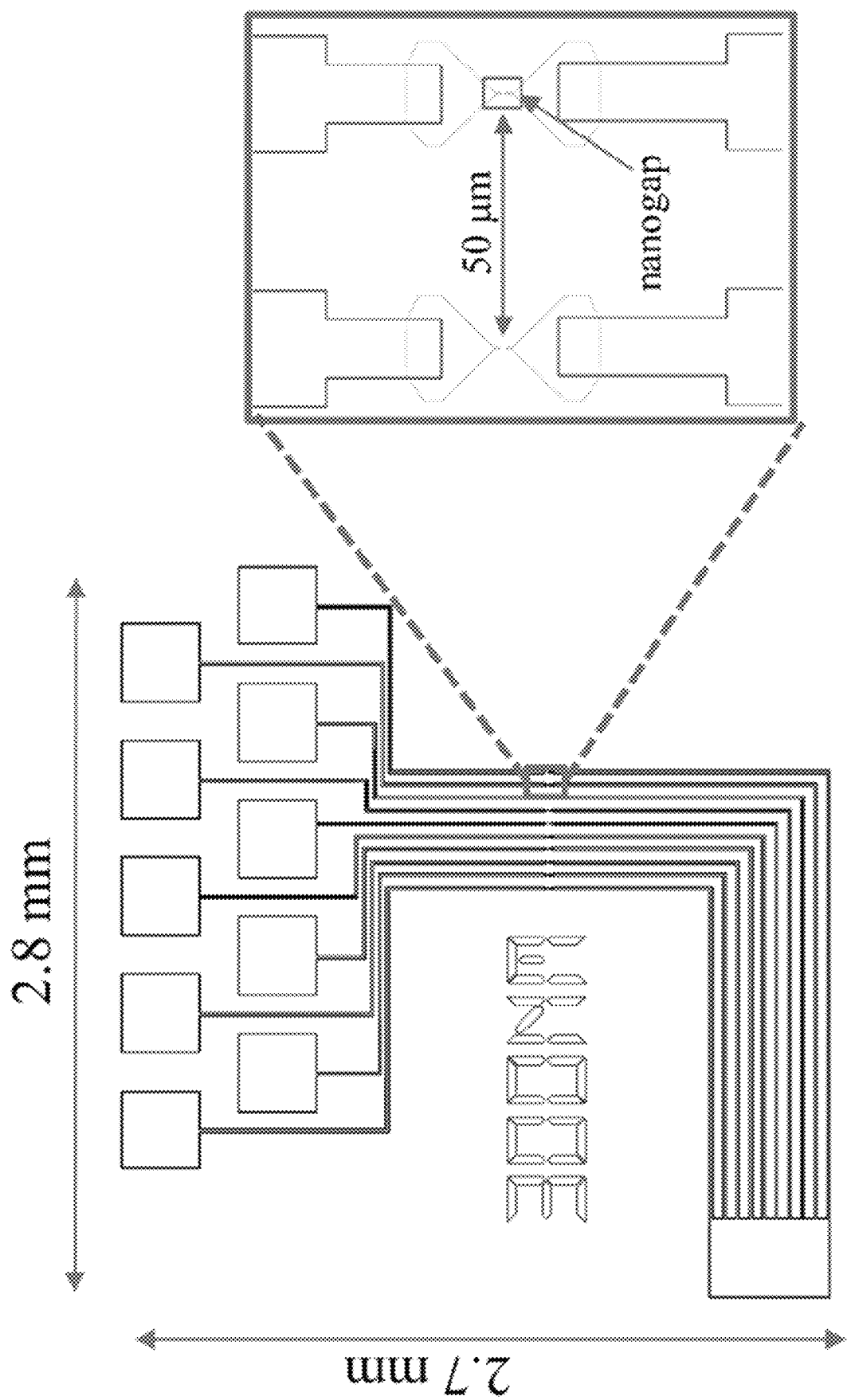
FIG. 16 shows an exemplary scheme of the electrodes pattern used to immobilize the aptamer-functionalized CNT.

To employ the so formed SWCNT-aptamer hybrids in electrical biosensing devices the inventors: (i) patterned metal electrode pairs on doped silicon wafers via electron beam lithography (see FIG. 16), (ii) cast the solutions on the so fabricated substrates, and (iii) immobilized the nanotubes between the electrodes via DEP. The assembly between electrodes is induced by an applied AC voltage bias: FIGS. 15 and 3 shows the schematic of the strategy utilized, as well as a representative AFM image of aptamer-functionalized SWCNTs aligned between two pre-patterned electrodes (see also Example 4 and FIG. 14D).

Dielectrophoresis (DEP) was performed by applying a voltage between a pair of electrodes after having cast the aptamer-functionalized CNT solution. By tuning the voltage applied, the time of application, and the concertation of the solution the inventors could control the immobilization between one to few tens of CNTs bridging the patterned electrodes. The inventors have optimized these parameters by checking via AFM the amount of CNTs immobilized; once the DEP parameters were optimized, we could assemble aptamer-functionalized CNTs on the electrode pairs with a bridging yield up to 95%. The frequency of the generator was switched onto typically Vp–p=3V at f=400 KHz; a drop of CNT-aptamer hybrids solution (5 μL, ~100 ng/mL) was cast to the chip with a pipette. After a delay of typically 30 seconds, the substrate was washed with water and blown gently with Nitrogen gas. The devises are usable with more than one CNT bridging the electrode. The immobilization of 1 CNT with this method is also possible, but at lower yield (ca. 20%).

Example 13: Characterization 13.1 AFM Measurement

Topography analysis of the electrodes were imaged with a Bruker Dimension Icon atomic force microscope (AFM) with ScanAsyst Air tips. The sample solution of CNT-aptamer hybrids was deposited onto a piece of freshly cleaved mica, which was pre-treated with 1 M $MgSO_4$ solution to enhance DNA adsorption, rinsed with water and dried before AFM measurement. These samples were imaged with a Bruker Dimension Icon atomic force microscope with ScanAsyst Air tips.

13.2 Electrical Measurement

Electrical measurements were performed using a probe station (PS-100, Lakeshore) equipped with a semiconducting parameter analyser (Keithley, 4200SCS) at room temperature. Gate bias sweeping mode (−6V to 6V) was used to record the source-drain current ($I_{sd}$) versus gate bias ($v_g$) data. For real time measurements, 100 mV source-drain bias and −2 V gate bias were applied across the devices whereas different solutions were cast on the substrate.

13.3 DNA Hybridization and Denaturation

Figure 17:
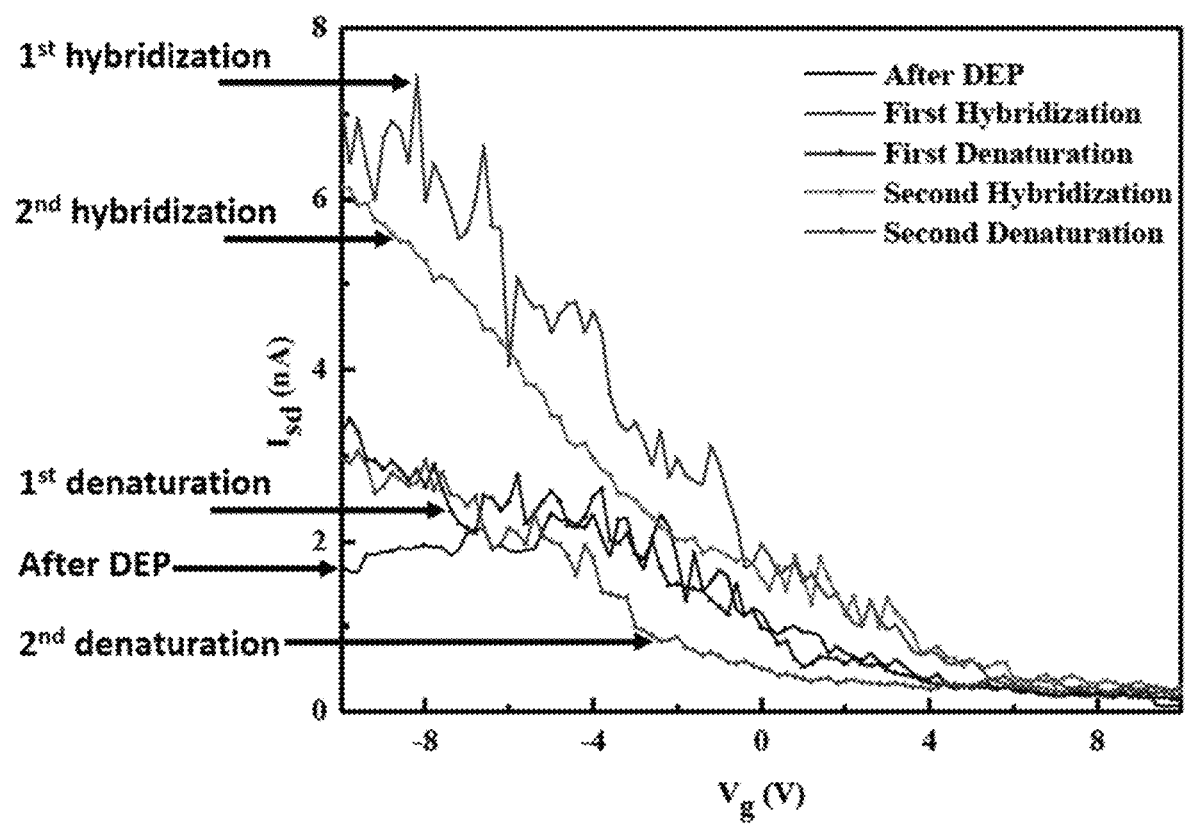
FIG. 17 shows the electrical response of the SWCNT-aptamer field effect transistor, before (black) and after DNA hybridization (red) and DNA denaturation (blue), and an additional cycle of DNA hybridization (green) and DNA denaturation (purple); $V_{sd}$=100 mV.

To confirm the accessibility of the nucleotide recognition element within the SWCNT-aptamer hybrids immobilized in the device configuration we performed in situ hybridization experiments exposing the chip to the cortisol aptamer's complementary ss-DNA, and recording the electrical response of the device when the ds-DNA (double-stranded) was formed. FIG. 17 shows a representative electrical response of the SWCNT-aptamer field effect transistor (FET), before and after DNA hybridization. The change in source-drain current indicates the occurred recognition of the complementary ss-DNA by the aptamer in the SWCNT-based devices. The observed shift of $V_{TH}$ (taken as the abscissa-intercept of the line tangent to the steepest part of the drain current versus gate voltage curve) points to a potential scattering mechanism occurring upon the rearrangement of the aptamer's conformation due to DNA hybridization.

Hybridisation and denaturation experiments were carried out using the following method: 40 μL complementary DNA (diluted in DPBS, 1 μM) was cast on the devices. Then the devices were incubated in water bath at 50° C. for 2 h and cooled down to room temperature. The devices were withdrawn from the solution, washed with water and dried with Nitrogen gas for electrical characterization. After hybridization, the devices were immersed in a 50% formamide/water solution at 30° C. for 4 h to denature the double stranded DNA. Then the devices were removed from the solution, washed with water and dried with Nitrogen gas for further electrical characterization.

13.4 Multiplexed Detection in Buffer

Cortisol and DHEAS were dissolved in methanol, and then diluted in the Tris-HCl buffer to prepare cortisol and DHEAS solutions with different concentrations from 10 nM to 1 μM. NPY was dissolved in water and diluted with the Tris-HCl buffer to prepare NPY solutions with different concentrations from 100 pM to 1 μM.

For multiplexed detection experiments, three different solutions were used, namely, 100 nM cortisol solution in the Tris-HCl buffer, 100 nM cortisol solution and 50 nM NPY in the Tris-HCl buffer, and 100 nM cortisol solution, 50 nM NPY and 100 nM DHEAS in the Tris-HCl buffer. For each detection, the devices were immersed in the solution, incubated for 0.5 h, and finally washed with water and dried with Nitrogen gas for electrical characterization. Subsequently, after each detection and in order to regenerate the biosensors, the substrates were immersed in a Tris-HCl buffer solution with 8 M of Urea. After 1 h, the devices were washed with water and dried with Nitrogen gas for characterization.

13.5 Analytes Detection in Serum

Steroid-free serum was diluted with the Tris-HCl buffer by 10-fold. Different analytes concentrations were diluted with serum (from 100 pM to 2 μM). A drop of 2 μL diluted serum was cast onto the substrate and then 100 mV source-drain bias and −2 V gate bias were applied for the baseline. For each analyte detection in serum, 50 seconds were recorded (as baseline) and then 2 μL of the analyte dissolved in serum was added to the previous drop.

Example 14: Control Experiment with Non-Functionalized Device

Figure 18:
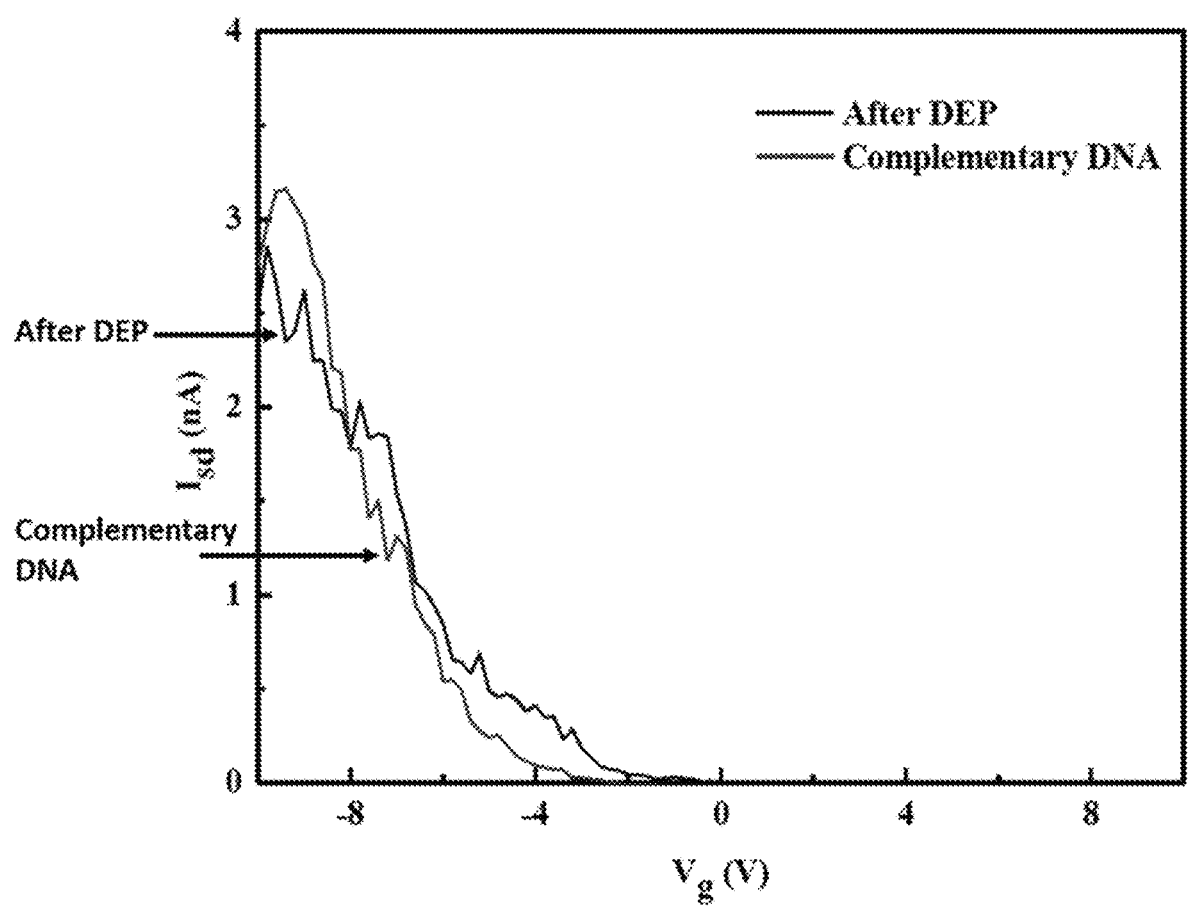
FIG. 18 shows the source-drain current ($I_{sd}$) vs gate bias ($V_g$) characterization of the non-functionalized device before and after exposure to the ss-DNA, $V_{sd}$=100 mV.

A device was prepared in which CNTs were not been functionalized with aptamers, i.e. (GTT)$_3$G-amine wrapped CNTs were directly immobilised between electrodes via DEP. The current showed no significant change after exposure of this device to complementary DNA (FIG. 18). That is, when the CNTs in the devices were not functionalized with the aptamer, the inventors did not record any change in current upon addition of the complementary ss-DNA.

Moreover, the exposure of the devices to noncomplementary DNA did not induce any significant electrical response of the devices (see FIG. 19), demonstrating the selectivity of the DNA hybridization detection. By exposing the chip to formamide, we were able to denature the ds-DNA, without affecting the electrical properties of the SWCNT-aptamer hybrids, that indeed showed comparable current responses to the initial stage: this further proves the reconfigurable nature of the platform via a simple cleaning procedure (see FIG. 17 and FIG. 19 and Examples 13.3 and 15 respectively).

Example 15: Control Experiments with Non-Complementary and Complementary DNAs

To confirm that the change in current comes from DNA hybridization with the complementary DNA, the inventors exposed devices functionalized with cortisol aptamers to non-complementary DNA (5'-GAT TCA GCA ATT AAG CTC TAA GCG ATC CGC AAC ACT GAC CTC TTA TCA AAA GGA GCA ATT AAA GGT ACT CTC TAA TCC TGA CGG G-3'): no obvious change in current was observed. However, subsequent exposure to the complementary DNA induced an increase in current. After denaturation, the current decreased to the initial stage (FIG. 19).

Example 16: Control Experiment of Multi-Sensing Capability of the Devices with Cortisol and NPY In order to use the devices for multipurpose analysis, the inventors assembled SWCNT-aptamer hybrids exhibiting distinct biorecognition elements at different locations on the same chip. By separately addressing distinct electrodes pairs, it is possible to immobilize, via DEP, n aptamer-functionalized SWCNTs on n different electrode pairs. The organization of distinct SWCNT-aptamer hybrids from solution to surfaces in parallel 2D device configurations on the same chip can then allow for the fabrication of multifunctional, high-throughput bioelectronic devices with parallel multipurpose sensing capability (see FIG. 5). The electronic devices prepared in this way withstand and respond to various environmental changes on the same substrates, depending on the different aptamers employed: upon recognition of an analyte, the specific aptamer will undergo a structural rearrangement and induce a change in the electrical response (resistance) of the CNT embedded in the device.

To demonstrate the multisensing capability of the devices, three distinct SWCNT-aptamer hybrids were immobilized on separate electrode pairs, on the same chip: this step is marked as "after DEP" in the curves shown in FIGS. 12A-C.

In particular, we used aptamers targeting the aforementioned biomarkers indicative of stress and neuro-trauma conditions, i.e., cortisol, NPY and DHEAS. We performed subsequent detection experiments on the same chip, employing different solutions containing either one, two, or all three biomarkers. Upon selective binding of a metabolite to the specific aptamer tethered to the SWCNTs we observed a reduction in the current response only for the corresponding device on the chip, without any crosstalk between the different devices selective to the other analytes nor any false-positive signals (see FIGS. 8 to 10 and 12; also see below regarding the relationship between FIGS. 8 to 10). Notably, each distinct nanoscale device on the chip could be reversed to its initial state by removing the metabolite bound to the aptamer via the addition of a urea solution ("cleaning" in FIGS. 12D-I): this allowed the inventors to perform multiple detection tests on the same chip, and successfully demonstrate the multiplexed electrical detection of the three biomarkers of interest.

The above demonstrated the multi-sensing capability of the device with cortisol and NPY sensor on the same chip. Furthermore, it demonstrated that each distinct nanoscale device on the chip could be reversed to its initial state by removing the metabolite bound to the aptamer via the addition of a urea solution. This is demonstrated by FIGS. 8 to 10. Firstly, the data shown in FIGS. 8A and 9B were obtained. A cleaning step to regenerate the biosensor was subsequently performed (involving the addition of 8M urea), and then the data for FIGS. 8B and 9A were obtained. The traces labelled "before NPY detection" were obtained just after the cleaning step. A further cleaning step was subsequently performed and then the data for FIGS. 10A and 10B were then obtained. The traces labelled "before mixture detection" were obtained just after the cleaning step.

Example 17: Calibration Curves of the Real-Time Detection of Three Analytes

Figure 20A:
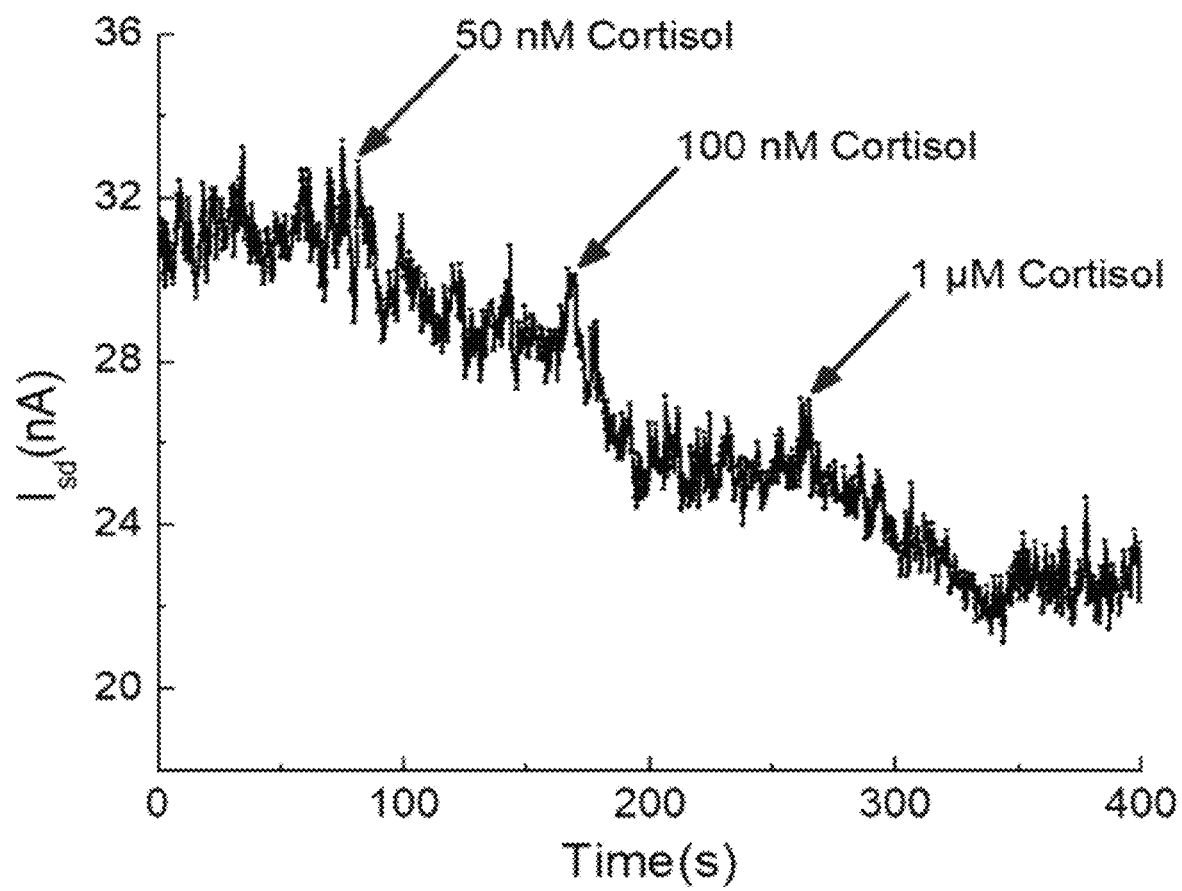
FIG. 20 shows the real time detection of (A) cortisol (from 50 nM to 1 μM), (B) DHEAS (from 10 nM to 1 μM), and (C) NPY (from 500 pM to 1 μM) at various concentrations, in serum ($V_{sd}$=100 mV, $V_g$=−2 V).
Figure 20B:
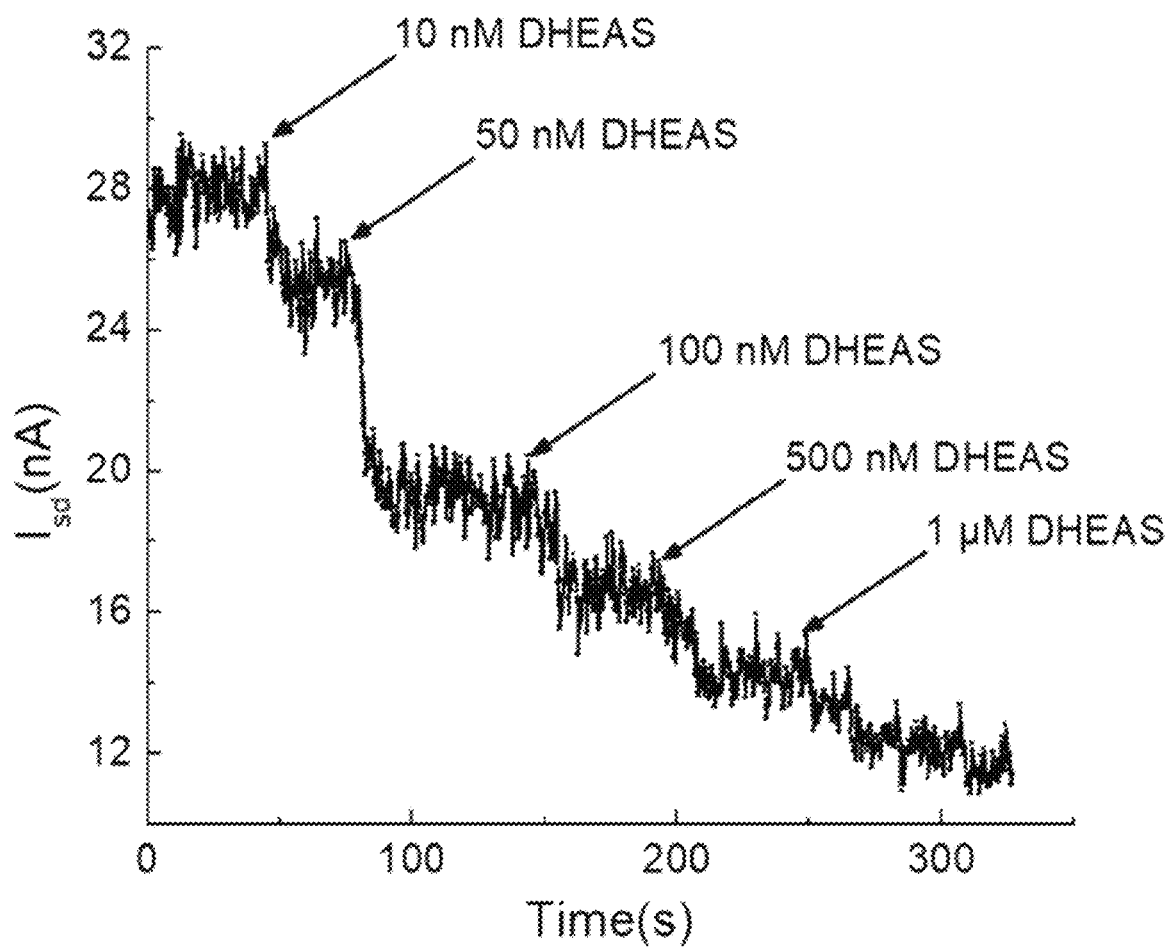
Figure 20C:
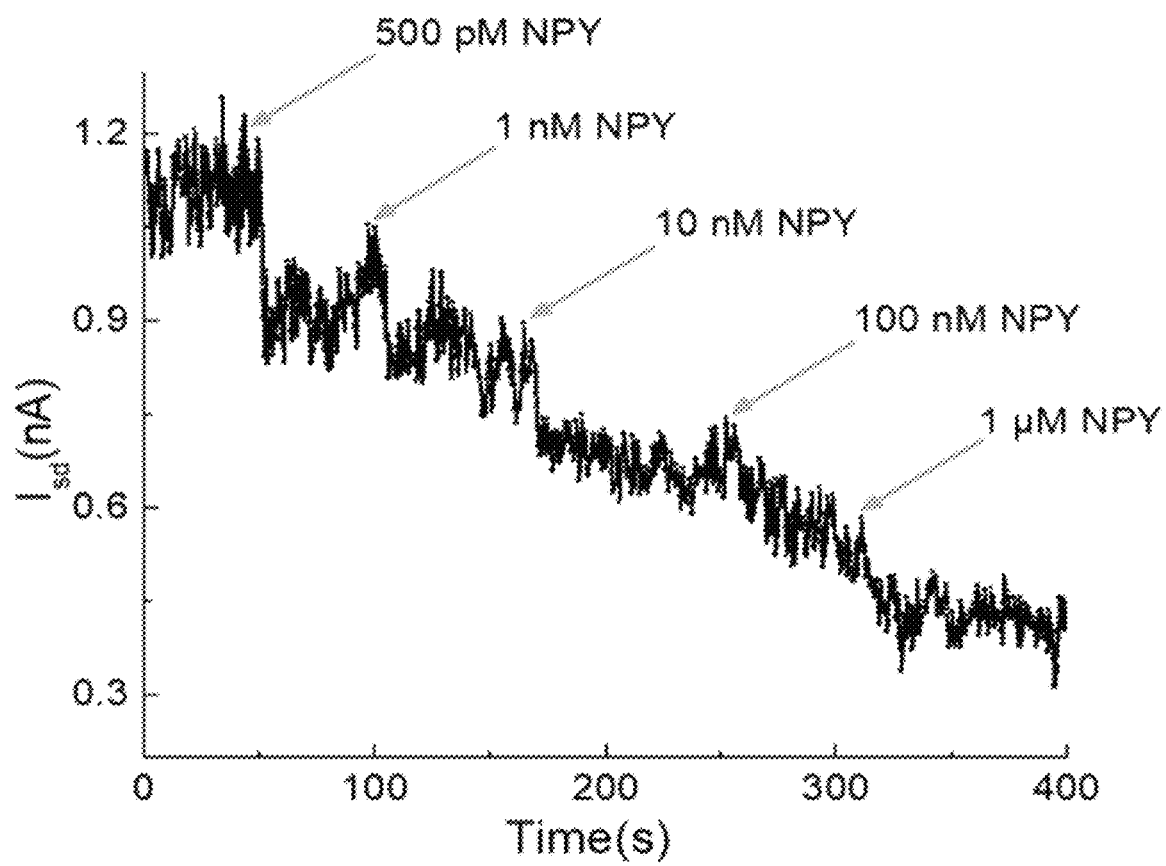

The inventors further investigated the real-time detection of cortisol, DHEAS, and NPY, at their relevant physiological concentrations in serum, i.e., from 1 μM to 100 pM. The devices were first immersed in serum subsequently, different concentrations of each biomarker were added to the devices at different time intervals. The electrical response increased with the change in concentration; we detected in real-time concentrations of cortisol, DHEAS, and NPY down to ca. 50 nM, 10 nM, and 500 pM, respectively: see FIG. 20 and the calibration curves shown in FIG. 21. The drop in $I_{sd}$–$V_g$ is likely due to a screening charge in the CNTs induced by the change in conformation of the aptamer upon analyte binding, as previously observed for ss-DNA folding in CNT-DNA devices. Control samples, where the nanotubes in the devices were not functionalized with any aptamer, did not exhibit any change in their electrical response upon the addition of the aforementioned biomarkers (see FIG. 22 and Example 18). This further confirmed the selectivity and biosensing nature of the devices presented here.

Figure 21A:
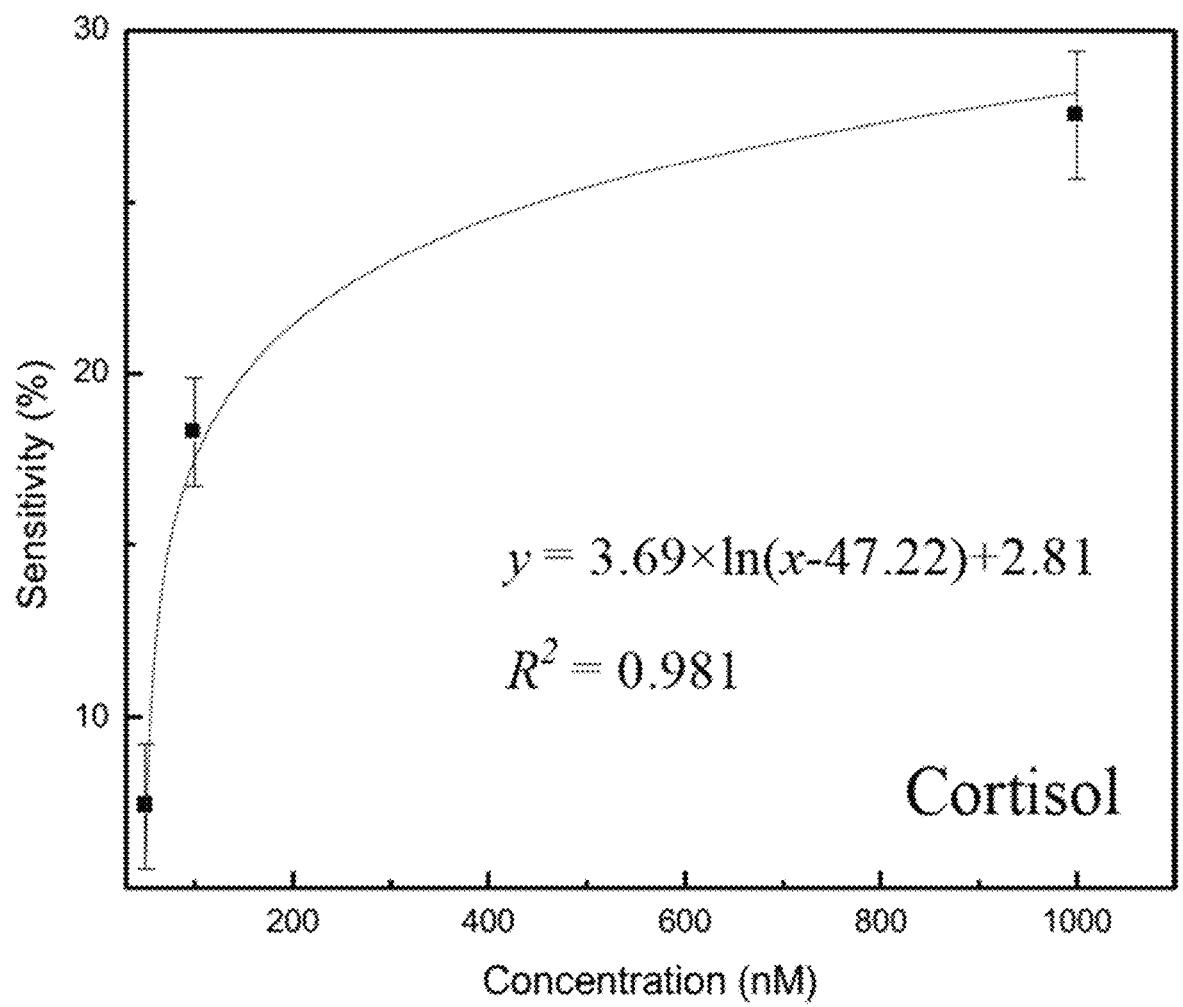
FIG. 21 shows the calibration curves of the real-time detection of three analytes (A) Cortisol (B) NPY (C) DHEAS.
Figure 21B:
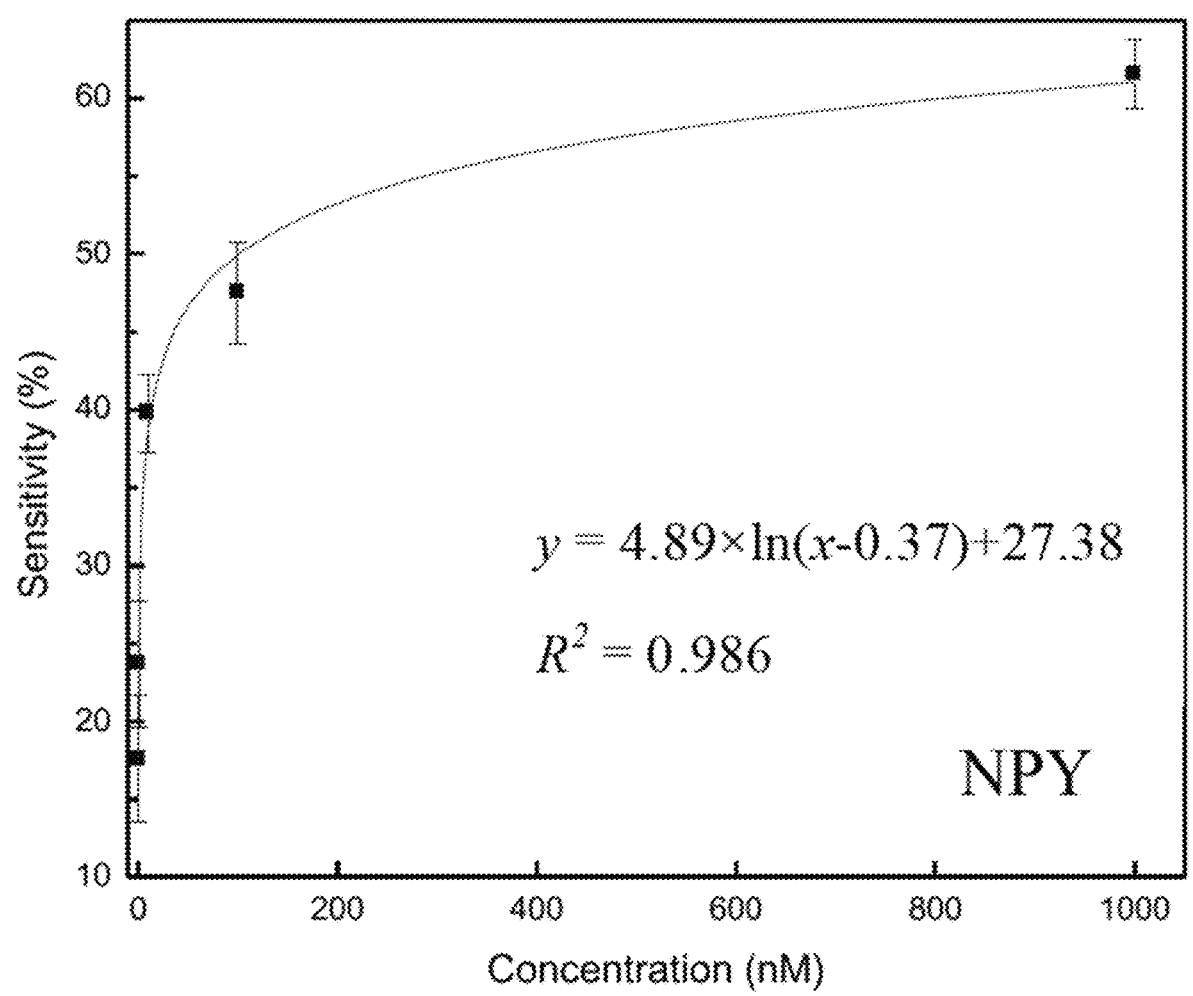
Figure 21C:
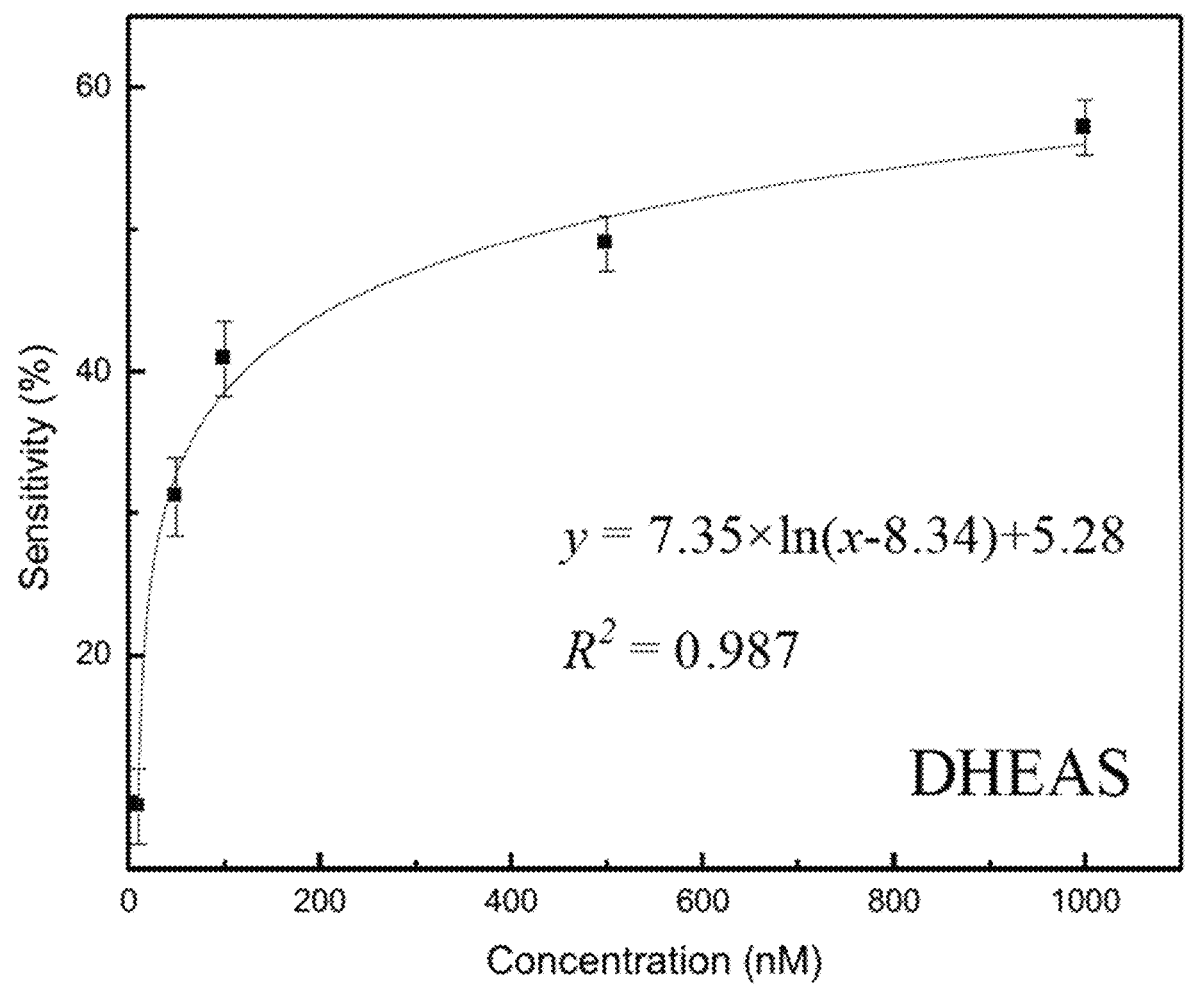

In more detail, based on the data of the real-time detection the calibration curves for three analytes were calculated (see FIG. 21). In the real time detection experiment (shown in FIG. 20 of the manuscript), different concentrations of analytes were added, which induced significant decreases in current, reaching plateaus for each addition of analyte. The initial current is recorded, and the average value of the data is taken as the baseline value ($I_0$). Similarly, the average current of each plateau (I) can be calculated and this is done for each detection/concentration. Thus, the sensitivity (S) of the sensor (to each concentration of analytes) can be calculated, according to Equation (1):

$$S = \frac{|I - I_0|}{I_0} \times 100\% \quad (1)$$

The data was plotted and fitted by using equation (2):

$$y = a \times \ln(x-b) + c \quad (2)$$

Figure 22:
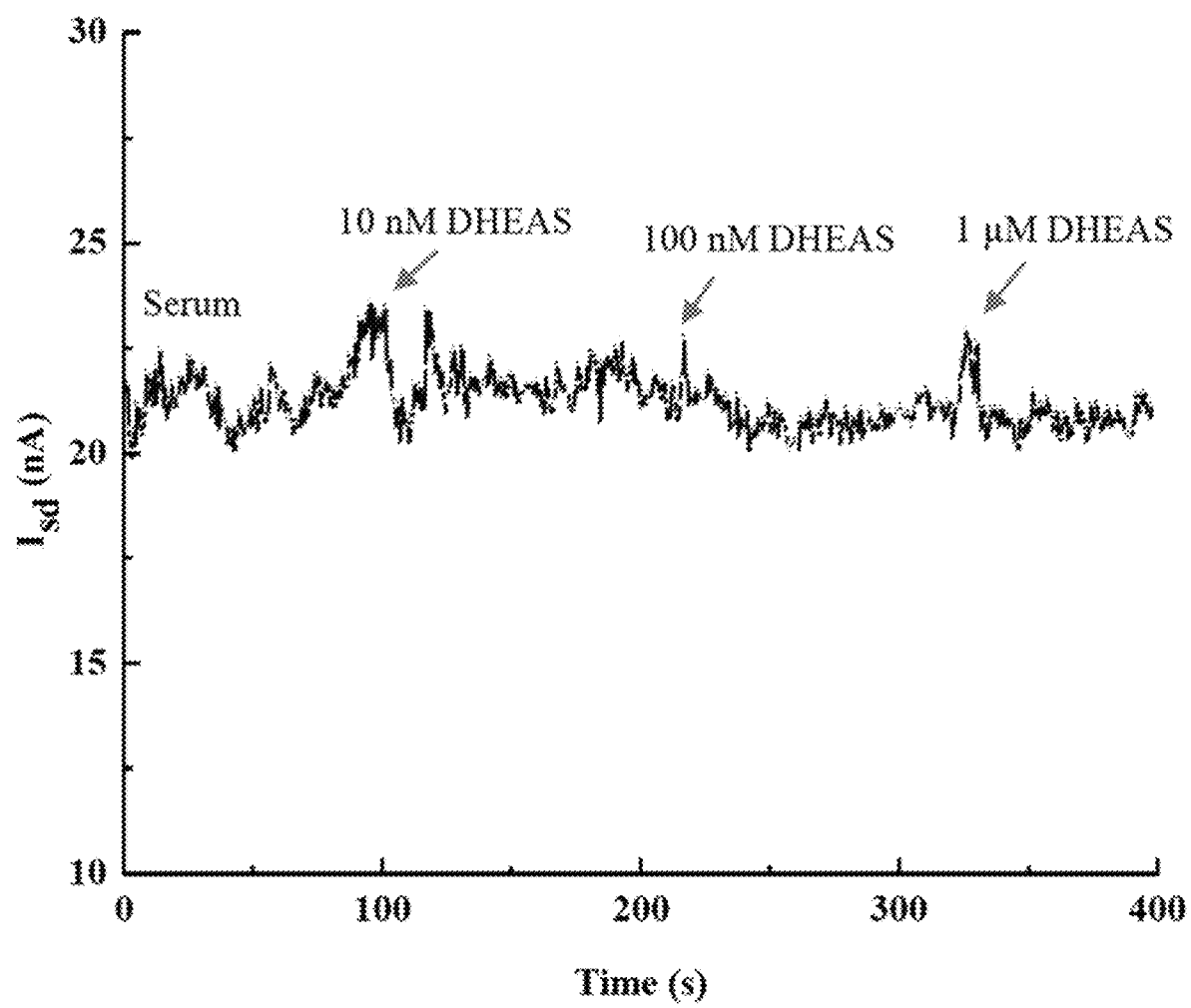
FIG. 22 shows the real time response of a non-functionalized CNT-device upon addition of DHEAS at different concentrations (from 10 nM to 1 μM).

Example 18: Control Experiments of Detection of DHEAS with Non-Functionalized Device in Serum To confirm that the change in current originates from the aptamers binding to the analytes, real time detection of DHEAS was performed on a non-functionalized CNT device. Initially, the device was covered with a drop of serum solution, then DHEAS solutions with different concentrations were added. The inventors noticed that there was no significant change in current after adding different concentrations of DHEAS (FIG. 22).

Example 19: Control Experiments with Sodium Deoxycholate (SDC) and DHEAS

Figure 23A:
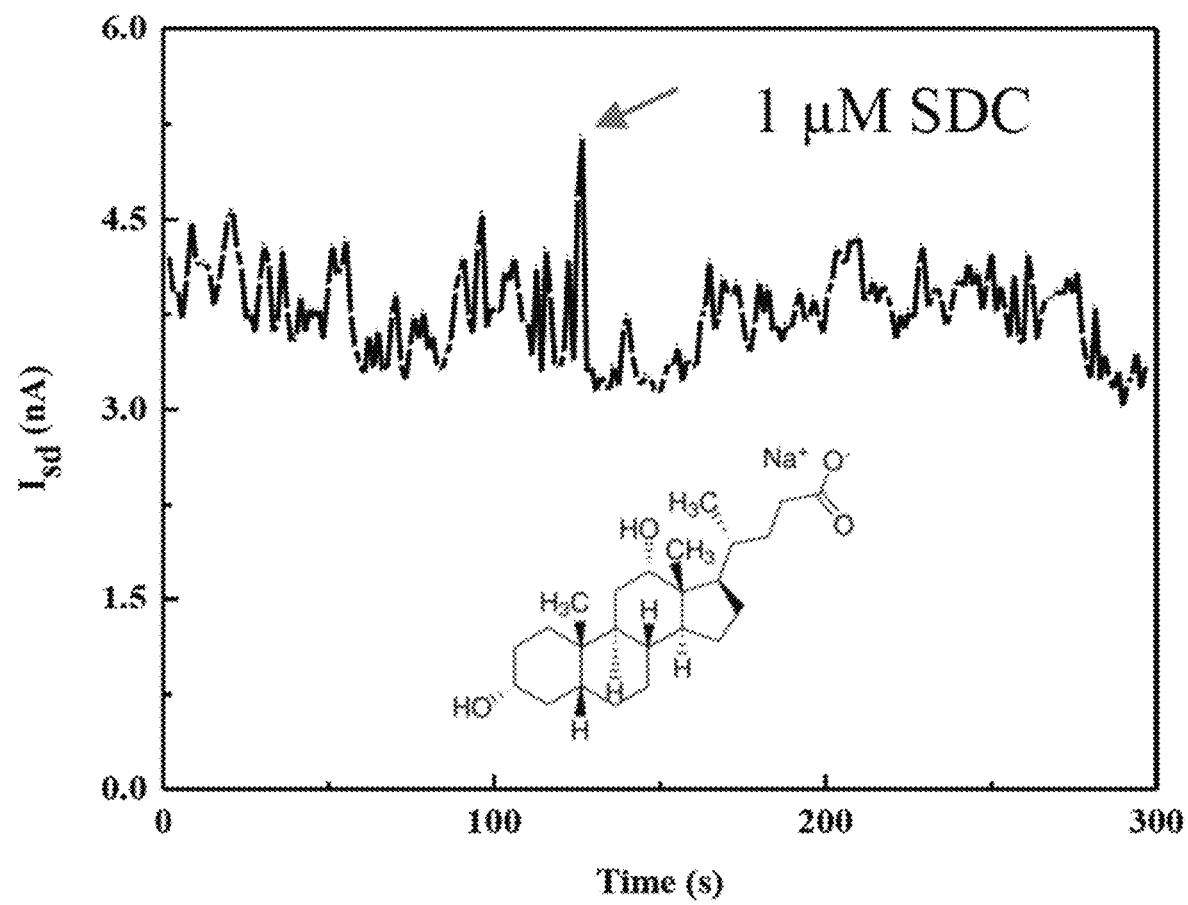
FIG. 23 shows the real time detection of (A) 1 μM SDC and (B) 1 μM DHEAS on the same device and (C) $I_{sd}$ vs $V_g$ characterization of the device before detection and after SDC and DHEAS.

To further demonstrate the selectivity of the fabricated multiplexed platform also for real-time measurements, we tested the DHEAS-sensitive sensor with a molecule possessing similar molar mass and chemical structure to DHEAS (sodium deoxycholate, SDC). As shown in FIG. 23A, SDC was added at a concentration of 1 µM, and no changes were observed in the current of the DHEAS-sensitive sensor. The sample was then cleaned with DI water and exposed to a 1 µM DHEAS solution. A sharp decrease in the conductance was at this point observed as expected (FIG. 23B), in line with the results shown in FIG. 20B. Additionally, the source-drain versus gate voltage measurements further confirmed the high selectivity of the platform (see FIG. 23C).

Figure 23B:
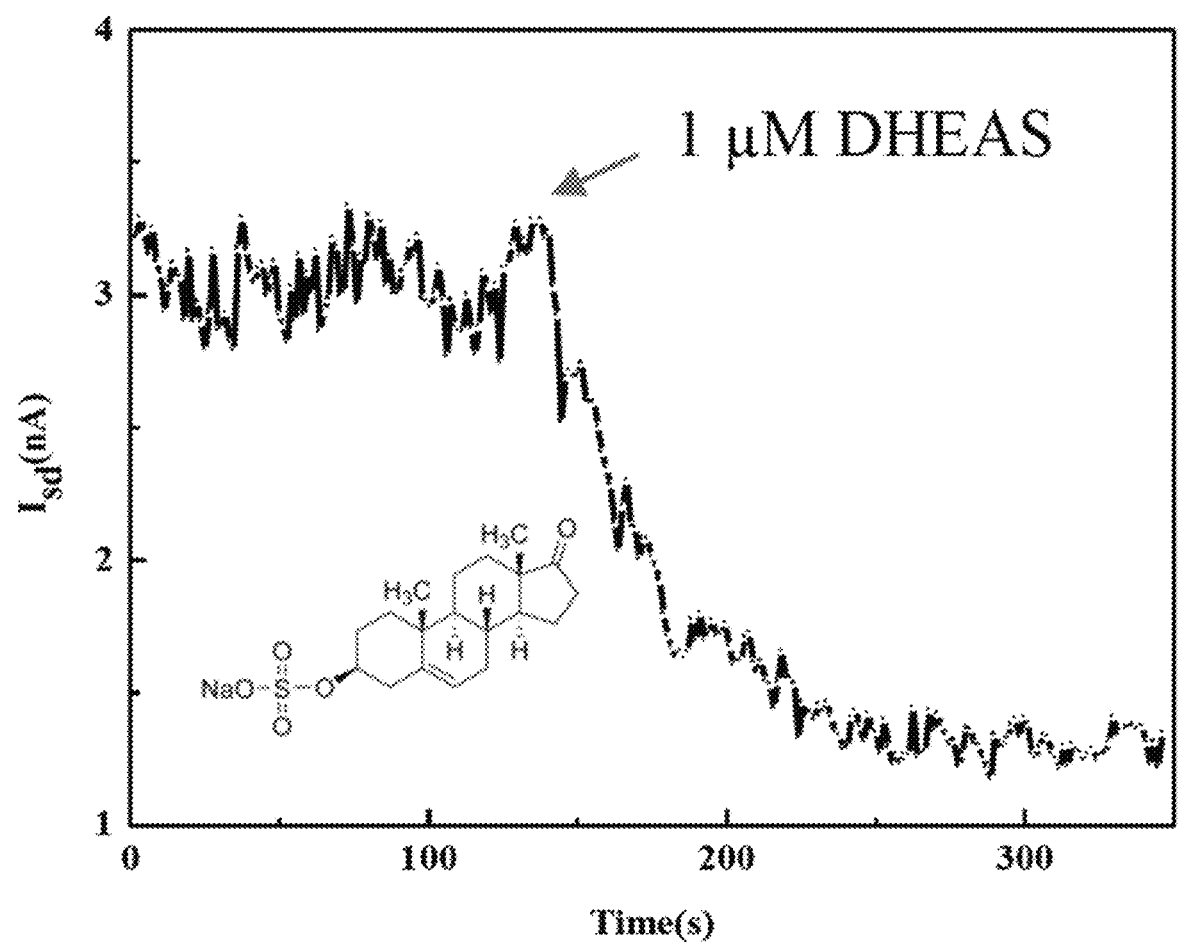
Figure 23C:
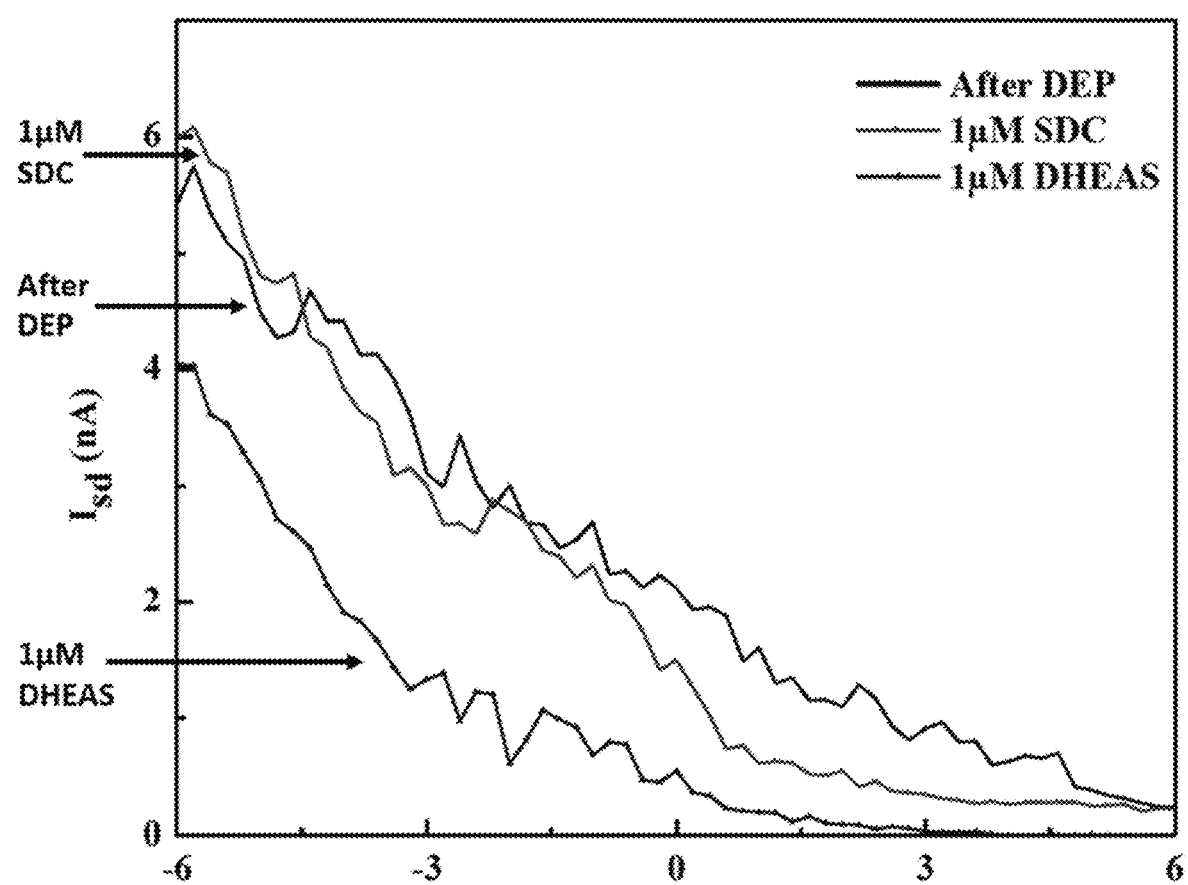

To demonstrate the selectivity of the devices, real time detection of SDC and DHEAS were performed on the same device, a DHEAS-sensitive CNT-aptamer sensor. As shown in FIG. 23A, there was no obvious change in current after adding 1 µM SDC to the device. Subsequently, adding 1 µM DHEAS to the device induced a sharp decrease in current (FIG. 23B). $I_{sd}$ vs $V_g$ characterization showed a similar result (FIG. 23C).

The inventors have presented a novel solution-processable method of general applicability for the fabrication of label-free nanoscale biosensing devices that permits the real-time and simultaneous detection of multiple analytes on the same chip.

The inventors have assembled hybrids of SWCNTs and aptamers from solution to surfaces in nanoscale device configurations where the nanotubes could act as the transducer elements, and the aptamers as the recognition components, of an electrical biosensing platform. As proof of concept, the inventors demonstrated the selective recognition of different biomarkers indicative of stress and neurotrauma conditions, at various physiologically relevant concentrations, from pM to µM. The devices exhibited high selectivity and sensitivity, as well as multiplexing ability due to the immobilization of CNT-aptamer hybrids with distinct biorecognition elements on the same nanoscale chip via a DEP-based strategy; this grants low cost processability and low power consumption. Additionally, the devices are reconfigurable and reusable via a cleaning procedure. These results represent the first example of solution-processable and reconfigurable nanoscale multiplexing sensing devices based on the use of carbon nanostructures. By and large, the general applicability of the strategy developed, and the solution processability of the nanoscale multiplexing biosensing devices fabricated, hold great potential for the development of the next generation of portable, point of care and home diagnostic assays for the continuous and simultaneous monitoring of different health parameters.

It is to be understood that different applications of the disclosed methods and devices may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a sensor molecule" includes "sensor molecules", reference to "a nucleic acid" includes two or more nucleic acid molecules, and the like.

All publications, patents and patent applications cited herein, whether supra or infra, are hereby incorporated by reference in their entirety.

REFERENCES

Andrews et al. (J. Neurochem. 2012, 120, 26-36).

Ao et al. (J. Am. Chem. Soc. 2014, 136, 10383-10392).

Ao et al. (J. Am. Chem. Soc. 2016, 138, 16677-16685).

Gatti et al. (Clin. Biochem. 2009, 42, 1205-1217).

Guo et al. (Adv. Mater. 2013, 25, 3397-408).

Hamaguchi et al. (M. Anal. Biochem. 2001, 294, 126-131).

Landry et al., (Nat Nano 2017, 12, 368-377).

Lapchak et al. (Stroke 2000, 31, 1953-1957).

Li et al., (Nanoscale Res. Lett., 2010, 5, 1072).

Liu et al., (Angew. Chem. Int. Ed. Engl., 2011, 50 (11), 2496-502).

Martin et al. (N. Anal. Bioanal. Chem. 2014, 406, 4637-464)

Mendonsa et al. (J. Am. Chem. Soc. 2005, 127, 9382-9383).

Ordinario et al., (Anal. Chem., 2014, 86 17, 8628-8633).

Palma et al., (J. Am. Chem. Soc. 2013, 135, 8440-8443).

Pan et al. (Polymer. 2006, 47, 4300).

Park et al. (Nano Lett. 2006, 6, 916-919).

Pugliese et al., (J. Am. Chem. Soc. 2015, 137, 9587-9594).

S. Sorgenfrei et al., (Nat Nano 2011, 6, 126).

Schnorr et al. (J. Mater. Chem. 2010, 21, 4768).

Sims et al. (J. Am. Chem. Soc. 2013, 135, 7861-7868).

So et al., (JACS, 2005, 127 (34), 11906-11907).

Vijayaraghavan (Phys. Status Solidi B, 2013, 250, 2505).

Weizmann et al. (J. Am. Chem Soc. 2011, 133, 3238).

Yang et al. (J. Am. Chem. Soc. 2012, 134, 1642-1647).

Zheng et al. (Nat. Mater. 2003, 2, 338-342).

Zhu et al., (J. Am. Chem. Soc. 2016, 138, 2905-2908).

The invention claimed is:

1. A method of assembling a biosensor device comprising two or more biosensor units, wherein each unit is capable of detecting a different target molecule in a sample, and wherein each unit comprises one or more biosensors each capable of detecting the same target molecule, the method comprising:
  (i) performing a first cycle to assemble a first biosensor unit comprising:
    A. providing a first solution comprising a population of first carbon nanotubes (CNTs) coated with nucleic acid molecules, wherein nucleic acid molecules are functionalised with functional groups suitable for coupling first sensor molecules to nucleic acid molecules, wherein each first sensor molecule is capable of binding to a first target molecule;
    B. providing a substrate comprising a plurality of electrode pairs;
    C. introducing the first solution to the substrate and immobilising one or more first coated CNTs across a junction separating a first electrode pair, wherein each first coated CNT forms an electrical connection between electrodes of the first electrode pair;
    D. coupling one or more first sensor molecules to the nucleic acid of each first coated CNT, wherein each first sensor molecule is capable of binding to a first target molecule;
    E. washing the entire substrate to remove non-immobilised first coated CNTs; and
  (ii) performing a second cycle to assemble a second biosensor unit comprising repeating steps (A) to (E), wherein in repeat step (A) the first solution is replaced with a second solution, the population of first coated CNTs is replaced with a population of second coated CNTs, and wherein functional groups are suitable for coupling second sensor molecules to nucleic acid molecules; wherein in repeat step (C) the first solution is replaced with a second solution, the one or more first coated CNTs are replaced with one or more second coated CNTs, and the first electrode pair is replaced with a second electrode pair; and wherein in repeat step (D) the one or more first sensor molecules are replaced with one or more second sensor molecules, wherein each second sensor molecule is capable of binding to a second target molecule.

2. A method according to claim 1, further comprising performing one or more further assembly cycles to assemble a biosensor device comprising three or more biosensor units; wherein each further assembly cycle comprises repeating steps (A) to (E), wherein in each repeat step (A) the first solution is replaced with a further solution, the population of first or second CNTs is replaced with a further population of CNTs, and wherein functional groups are suitable for coupling further sensor molecules to nucleic acid molecules;

wherein in repeat step (C) the first solution is replaced with a further solution, the one or more first or second coated CNTs are replaced with one or more further population of coated CNTs and the first or second electrode pair is replaced with a further electrode pair;

and wherein in each repeat step (D) the first or second sensor molecules are replaced with further sensor molecules, wherein in each further assembly cycle each one of the further sensor molecules is capable of binding to a further and different target molecule.

3. A method according to claim 1, wherein in any step (A) the nucleic acid molecules have been functionalised with functional groups before or after the population of first, second or further CNTs have been coated with nucleic acid molecules.

4. A method according to claim 3, wherein in any step (A) nucleic acid molecules are provided with functional groups before first, second or further CNTs are coated with nucleic acid molecules.

5. A method according to claim 1, wherein in any assembly cycle, step (D) of coupling one or more sensor molecules to each coated CNT is performed after step (A) and before step (C).

6. A method according to claim 5, wherein for each assembly cycle, steps (A) and (D) are separately performed, and wherein each population of coated CNTs coupled with target molecules is then sequentially immobilised by performing steps (B), (C) and (E).

7. A method according to claim 1, wherein in any assembly cycle, step (C) comprises immobilising more than one CNT between any one or more pair of electrodes, optionally wherein 5 or more CNTs are immobilised between any one or more pair of electrodes.

8. A method according to claim 1, wherein in any assembly cycle, step (C) is performed by dielectrophoresis (DEP) by electrically addressing individual electrodes of a pair.

9. A method according to claim 1, wherein in one, more or all assembly cycles the nucleic acid is functionalised by providing a free amino group on the nucleic acid.

10. A method according to claim 9, wherein sensor molecules are coupled to nucleic acid via an amidation reaction between an azide group provided on the sensor molecule and a free amino group provided on the nucleic acid.

11. A method according to claim 1, wherein sensor molecules are coupled to nucleic acid via linker molecules.

12. A method according to claim 1, wherein sensor molecules capable of binding target molecules are: (a) small molecules, oligonucleotides, oligonucleotide aptamers, peptides, peptide aptamers polypeptides, antibodies, enzymes and/or peptide nucleic acids (PNA); and/or (b) complexes comprising any combination of sensor molecules defined in (a).

13. A method according to claim 1, wherein sensor molecules are: oligonucleotide aptamers capable of binding (i) cortisol; (ii) neuropeptide Y (NPY); or (iii) dehydroepiandrosterone sulfate (DHEAS).

14. A method according to claim 1, wherein the sensor molecule is capable of binding a target molecule which is a protein, a cytotoxin, a peptide, an amino acid, a nucleotide, a chemical, a drug, a vitamin, an organic compound, an inorganic compound or an antibody.

15. A method according to claim 1, wherein the device is configured as a field effect transistor (FET) and provided with source (S), drain (D) and gate (G) terminals.

16. A method according to claim 1, wherein in any or all biosensors of the device the presence of a target molecule is detected by a change in an electrical response of a CNT/CNTs of a biosensor compared to the electrical response of the CNT/CNTs in the absence of the target molecule.

17. A method according to claim 1, wherein CNTs are single walled CNTs (SWCNTs), wherein nucleic acid is ssDNA, wherein sensor molecules comprise nucleic acid aptamers, and wherein step (C) is performed by dielectrophoresis (DEP).

18. A method according to claim 17, wherein step (D) of coupling one or more sensor molecules to each coated CNT is performed after step (A) and before step (C).

19. A method according to claim 1, wherein any one or more biosensor unit is capable of detecting a target molecule at a concentration of 100pM, or less than 100pM.

20. A method according to claim 1, wherein the sample is a sample of a biological fluid including but not limited to blood, serum, plasma, saliva, urine, mucous, vomit, faeces, and/or sweat.

21. The method of claim 14, wherein the protein is a hormone, an enzyme, a cytokine, a neuropeptide, a cancer antigen, or an antigen derived from a microorganism.

22. The method of claim 21, wherein the antigen is derived from a bacterium, a virus or a fungus.

23. The method of claim 7, wherein between about 5 to about 10 CNTs are immobilised between any one or more pair of electrodes.

24. The method of claim 14, wherein the cytotoxin is a lipopolysaccharide.

25. The method of claim 16, wherein the change in the electrical response which is measured is the current (I).

26. The method of claim 17, wherein each biosensor of a unit comprises between about 5 and about 10 CNTs immobilised between electrodes of a pair.

27. The method of claim 1, wherein the substrate comprises $SiO_2$ and the method further comprises functionalizing the $SiO_2$ substrate comprising the plurality of electrode pairs with a coating comprising polyethylene glycol (PEG) silane prior to immobilising one or more coated CNTs between separate electrode pairs.

28. The method of claim 1, wherein the one or more first coated CNTs are aligned across the junction separating a first electrode pair and the one or more second coated CNTs are aligned across the junction separating a second electrode pair.

29. The method of claim 28, wherein the alignment is effectuated by dielectrophoresis (DEP).

* * * * *